United States Patent
Uchiyama et al.

(10) Patent No.: US 8,038,600 B2
(45) Date of Patent: Oct. 18, 2011

(54) MEDICAL SYSTEM

(75) Inventors: Akio Uchiyama, Yokohama (JP); Isao Aoki, Sagamihara (JP); Shinsuke Tanaka, Hachioji (JP); Hironobu Takizawa, Hachioji (JP); Hironao Kawano, Hino (JP)

(73) Assignee: Olympus Corporation, Tokyo (JP)

( * ) Notice: Subject to any disclaimer, the term of this patent is extended or adjusted under 35 U.S.C. 154(b) by 1189 days.

(21) Appl. No.: 11/663,124

(22) PCT Filed: Nov. 25, 2005

(86) PCT No.: PCT/JP2005/022126
§ 371 (c)(1),
(2), (4) Date: Mar. 16, 2007

(87) PCT Pub. No.: WO2006/057443
PCT Pub. Date: Jun. 1, 2006

(65) Prior Publication Data
US 2007/0299301 A1   Dec. 27, 2007

(30) Foreign Application Priority Data

Nov. 26, 2004  (JP) ................................ 2004-343138
Nov. 29, 2004  (JP) ................................ 2004-344650

(51) Int. Cl.
*A61B 1/04* (2006.01)
*A61B 1/00* (2006.01)
*A61B 1/06* (2006.01)

(52) U.S. Cl. .................. 600/118; 600/109; 600/160
(58) Field of Classification Search .............. 600/109, 600/117, 118, 160
See application file for complete search history.

(56) References Cited

U.S. PATENT DOCUMENTS

| | | | | |
|---|---|---|---|---|
| 5,681,260 | A * | 10/1997 | Ueda et al. | 600/114 |
| 6,240,312 | B1 | 5/2001 | Alfano et al. | |
| 2003/0181788 | A1 | 9/2003 | Yokoi et al. | |
| 2004/0111011 | A1 | 6/2004 | Uchiyama et al. | |
| 2004/0236180 | A1 | 11/2004 | Uchiyama et al. | |
| 2005/0085696 | A1 * | 4/2005 | Uchiyama et al. | 600/160 |
| 2005/0110881 | A1 * | 5/2005 | Glukhovsky et al. | 348/231.99 |
| 2005/0187433 | A1 * | 8/2005 | Horn et al. | 600/160 |
| 2005/0216231 | A1 * | 9/2005 | Aoki et al. | 702/183 |
| 2006/0063974 | A1 * | 3/2006 | Uchiyama et al. | 600/114 |
| 2006/0169293 | A1 * | 8/2006 | Yokoi et al. | 128/899 |
| 2008/0300458 | A1 * | 12/2008 | Kim et al. | 600/118 |

FOREIGN PATENT DOCUMENTS

EP   1 591 057   11/2005

(Continued)

*Primary Examiner* — Philip Smith
(74) *Attorney, Agent, or Firm* — Scully, Scott, Murphy & Presser, P.C.

(57) ABSTRACT

A medical system includes: a medical device to be inserted into the body cavity; a rotating device for the medical device for rotating the medical device around the insertion axis; an image pickup device provided to the medical device; and an image capturing timing detection device for detecting a signal regarding image capturing timing performed by the image pickup device. Furthermore, the medical system includes: a rotating angle acquisition device for acquiring the rotating angle of the rotating device for the medical device regarding the image capturing timing in response to the output of the image capturing timing detection device; and an image acquisition device for performing rotation processing for the image captured by the image pickup device based upon the information regarding the rotating angle acquired by the rotating angle acquisition device, thereby acquiring the image subjected to a rotation processing.

30 Claims, 52 Drawing Sheets

FOREIGN PATENT DOCUMENTS

| | | |
|---|---|---|
| JP | 60-56489 | 12/1985 |
| JP | 06-000190 | 1/1994 |
| JP | 2003-299612 | 10/2003 |
| JP | 2004-255174 | 9/2004 |
| WO | WO 2004/066830 | 8/2004 |

* cited by examiner

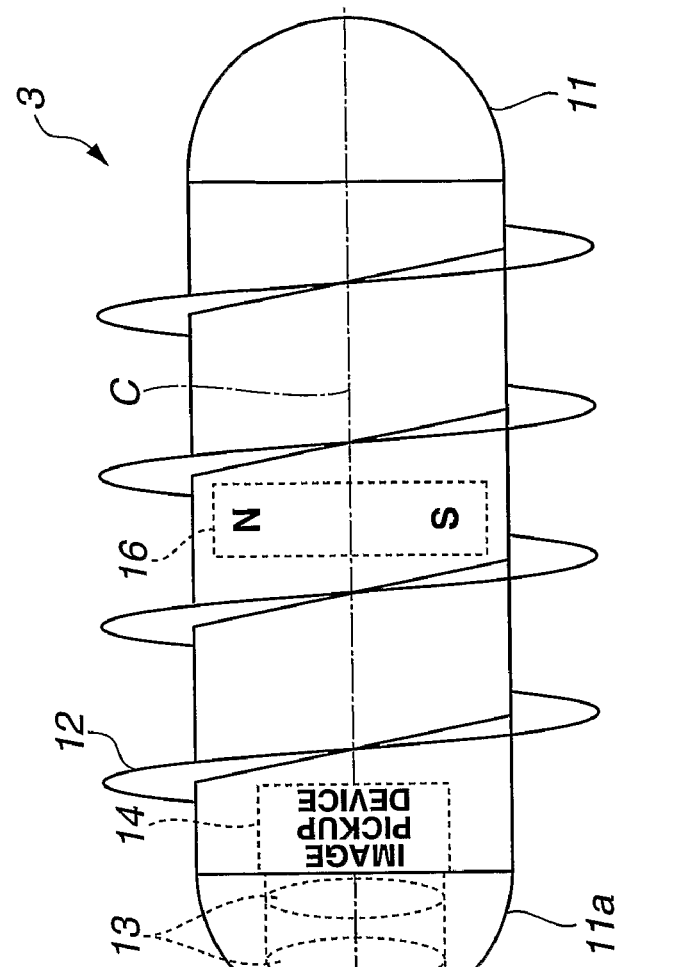
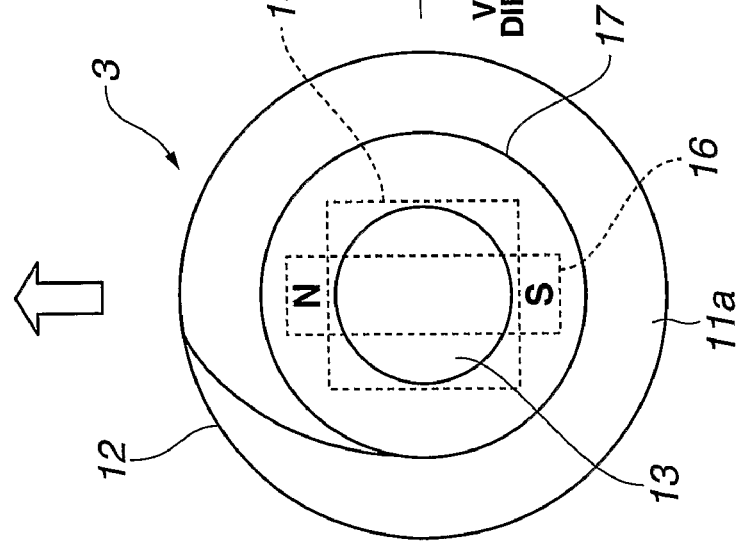

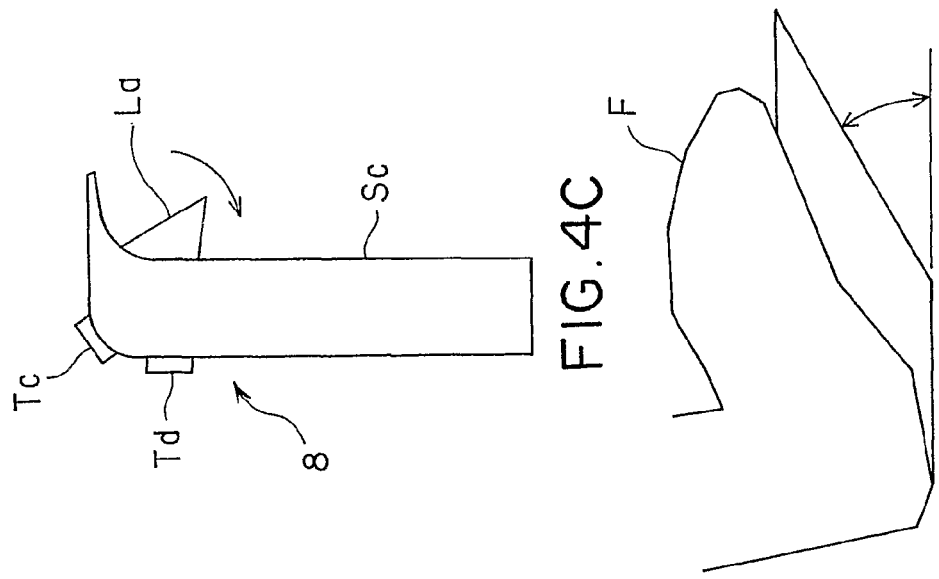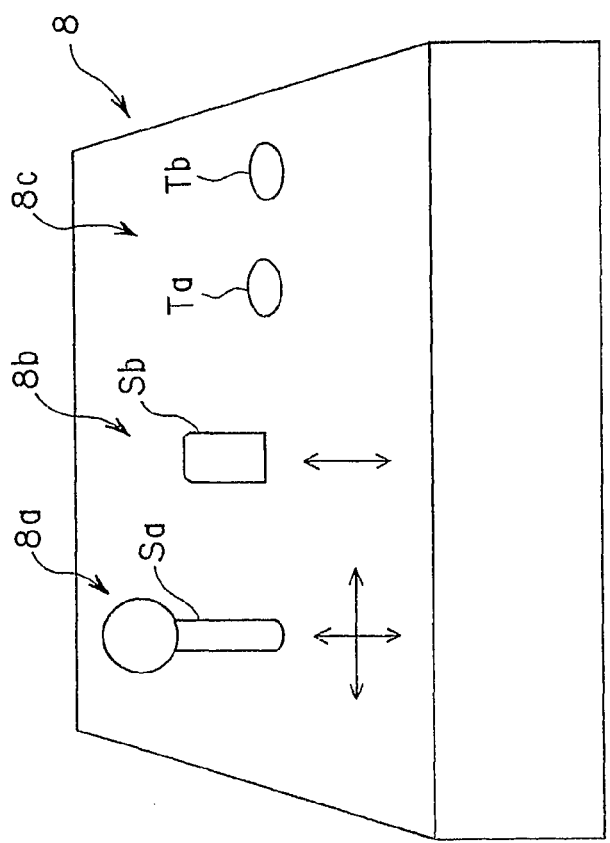

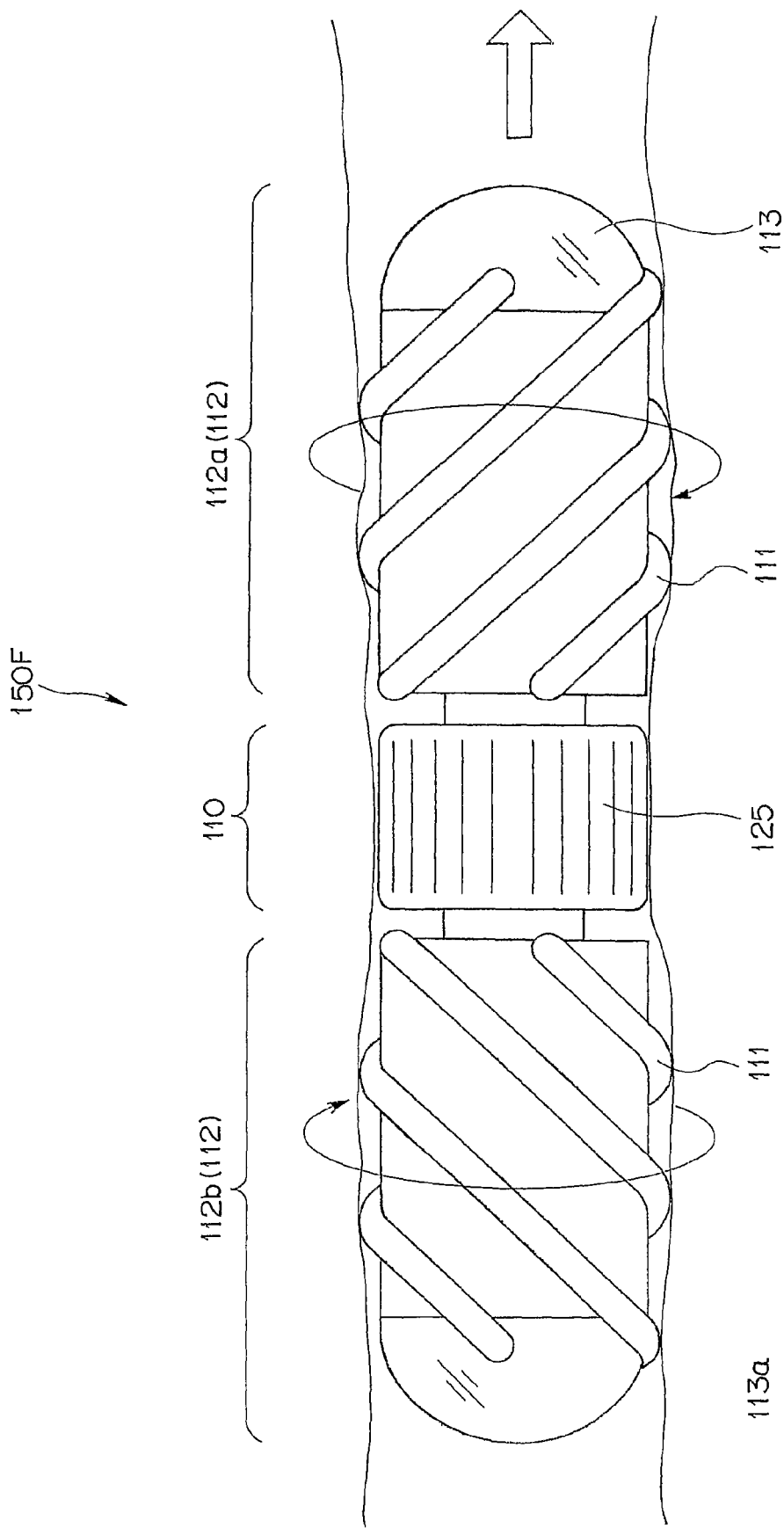

MEDICAL SYSTEM

TECHNICAL FIELD

The present invention relates to a medical system including a medical device having a function of generating propelling force within the body cavity by rotation thereof.

BACKGROUND ART

Various types of medical devices have been proposed, each of which is inserted into the body cavity, and has a function for generating propelling force and so forth by rotation thereof, thereby allowing examination of the body cavity.

For example, Japanese Unexamined Patent Application Publication No. 2003-299612 discloses a capsule endoscope system having a function for guiding a capsule endoscope within the lumen by applying a rotational magnetic field so as to rotate the capsule endoscope.

In the prior art disclosed in the above Patent document, the image data acquired by the capsule endoscope is transmitted to an image processing device outside of the body. The image processing device stores the received image data and the data of the rotational magnetic field in memory or the like in a correlated form.

Furthermore, in the prior art disclosed in the above Patent document, the image processing device performs image processing to correct for the rotation of the image using the data of the rotational magnetic field, thereby displaying an image which does not rotate.

However, the aforementioned prior art has a configuration in which the image data is stored by the image processing device outside of the body in a form correlated with the information regarding the rotational magnetic field at the time of the image data acquisition, thereby leaving a problem from the perspective of higher-precision rotation correction.

That is to say, although an arrangement in which the rotational state is detected at the time of image capturing would provide higher-precision rotation correction, such an arrangement is not disclosed in conventional techniques.

The present invention has been made in view of the aforementioned problems, and accordingly, it is an object thereof to provide a medical system for capturing an image using a rotating medical device with higher-precision rotation correction, thereby providing an image which allows more effective observation.

DISCLOSURE OF INVENTION

A medical system according to the present invention comprises: a medical device to be inserted into the body cavity; a rotating device for the medical device for rotating the medical device around the insertion axis; an image pickup device provided to the medical device; an image capturing timing detection device for detecting a signal with respect to the timing of image capturing performed by the image pickup device; a rotating angle acquisition device for acquiring the rotating angle of the rotating device for the medical device with respect to the image capturing timing in response to the output of the image capturing timing detection device; and an image acquisition device for performing rotation processing so as to rotate an image captured by the image pickup device based upon the information regarding the rotating angle acquired by the rotating angle acquisition device, thereby obtaining the image subjected to the rotation processing.

With the aforementioned arrangement, the information regarding the rotating angle of the rotating device of medical device is acquired at the image capturing timing performed by the image pickup device provided to the rotating medical device. This allows acquisition of the information regarding the rotating angle with respect to the actual image capturing timing performed by the image pickup device. Rotation correction is performed based upon the rotating-angle information, thereby enabling high-precision rotation processing.

BRIEF DESCRIPTION OF THE DRAWINGS

FIG. 3A is a side view of the capsule.

FIG. 3B is a front view of the capsule.

FIG. 4A is a diagram showing a schematic configuration of an operation input device.

FIG. 4B is a diagram showing a schematic configuration of an operation input device according to a modification.

FIG. 4C is a diagram showing a foot switch.

FIG. 65 is an external view of the capsule shown in FIG. 64.

BEST MODE FOR CARRYING OUT THE INVENTION

Description will be made regarding embodiments according to the present invention with reference to the drawings.

Embodiment 1

Description will be made regarding an embodiment 1 with reference to FIGS. 1 through 9.

Figure 1:
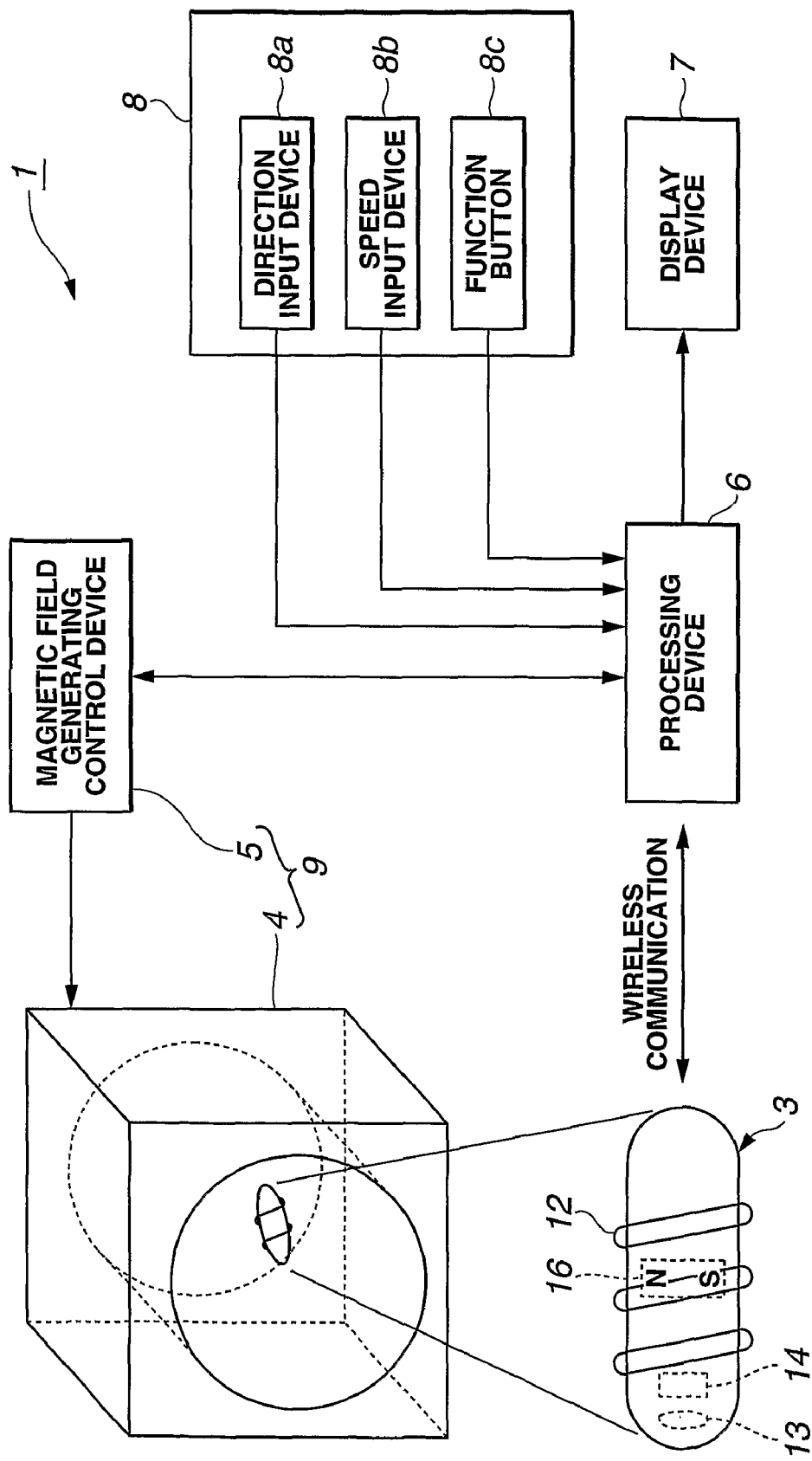
FIG. 1 is an overall configuration diagram showing a capsule medical system according to an embodiment 1 of the present invention.
Figure 2:
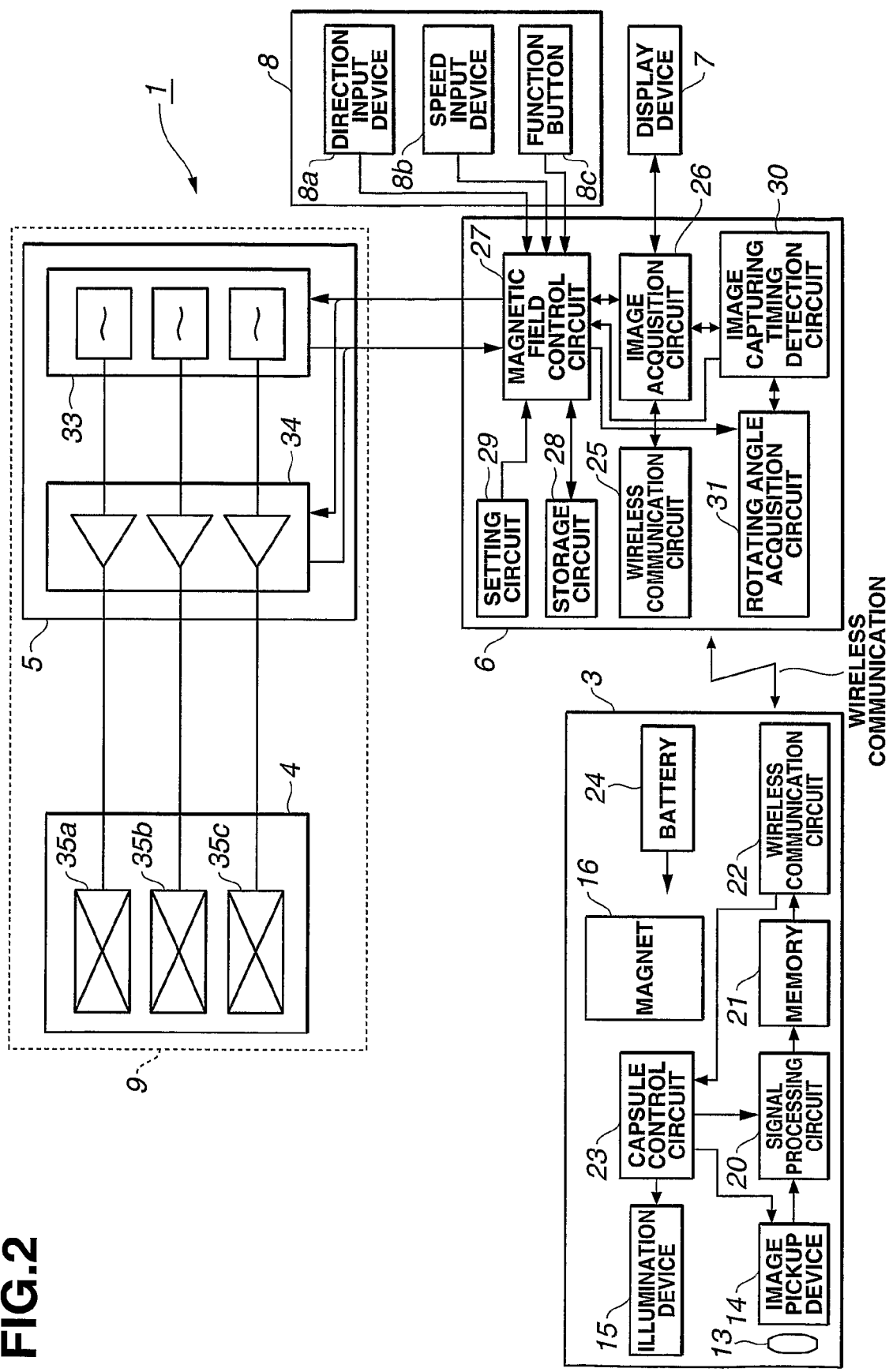
FIG. 2 is a block diagram showing an internal configuration of the components of the capsule medical system according to the embodiment 1 of the present invention.

As shown in FIGS. 1 and 2, a capsule medical system 1 according to the embodiment 1 of the present invention includes: a capsule medical device (a capsule endoscope) 3 (which will be simply referred to as "capsule" hereafter) serving as a capsule endoscope, which is inserted to the body cavity of an unshown subject from the mouth or anus, and which allows image capturing, diagnosis, and treatment and the like within the body cavity; and a magnetic field generating apparatus 9 which is positioned so as to surround the subject, i.e., is positioned outside of the subject. The magnetic field generating apparatus 9 comprises: a rotational magnetic field generating device 4 for applying a rotational magnetic field to the capsule 3, and a magnetic field generating control device (or power supply control device) 5 for controlling supply of the driving current for generating the rotational magnetic field at the rotational magnetic field generating device 4.

Furthermore, the capsule medical system 1 includes a processing device 6 which is positioned outside of the subject, and which has a function of wireless communication with the capsule 3 as well as a function for controlling the magnetic field generating control device 5 for controlling the direction, magnitude, and so forth of the rotational magnetic field applied to the capsule 3; a display device 7, which is connected to the processing device 6, for displaying an image captured by the capsule 3 and so forth; and an operation input device 8 which is connected to the processing device 6 and which allows the operator such as a surgeon to input instruction signals corresponding to the operation. Here, the operation input device 8 comprises: a direction input device 8a for generating an instruction signal for controlling the magnetic field direction; a speed input device 8b for generating an instruction signal for controlling the rotational frequency of the rotational magnetic field corresponding to the operation; and a function button 8c for generating an instruction signal corresponding to a predetermined function such as a function for generating an eccentric rotational magnetic field corresponding to the operation, for example.

As shown in FIGS. 3A and 3B, the capsule 3 includes a helical protrusion (or screw portion) 12 serving as a propelling force generating structure for generating the propelling force on the outer face of an exterior container 11 which is formed in the shape of a capsule, and which serves as an insertion portion to be inserted to the body cavity. The helical protrusion 12 allows the capsule 3 to generate the propelling force thereof by rotating the capsule 3 with the outer face thereof being in contact with the inner wall of the body cavity (inner wall of the lumen). Furthermore, the capsule 3 includes a magnet 16 within a space sealed with the exterior container 11, which allows rotation of the capsule 3 with a magnetic method using a rotational magnetic field generated by the rotational magnetic field generating device 4, as well as including: an objective optical system 13 and an image pickup device 14 positioned at an image-forming position thereof, forming image capturing means; an illumination device 15 for providing illumination for image capturing; and so forth (see FIG. 2).

As shown in FIG. 3A and so forth, the objective optical system 13 is disposed inside of a transparent distal end cover 11a formed in the shape of a hemisphere as a part of the exterior container 11, for example, with the optical axis thereof matching the center axis C of the cylindrical capsule 3. Thus, the center portion of the distal end cover 11a serves as an observation window 17 as shown in FIG. 3B. Note that the illumination device 15 is disposed around the objective optical system 13, which is not shown in FIG. 3A and so forth.

Accordingly, with such an arrangement, the objective optical system 13 has the viewing direction matching the direction of the optical axis thereof, i.e., the direction of the center axis C of the cylindrical capsule 3.

On the other hand, the magnet 16 is disposed within the capsule 3 around the center of the longitudinal direction thereof with the magnetic axis (direction of the line drawn from S-pole to N-pole) orthogonal to the center axis C as shown in FIG. 3 and so forth. With the present embodiment, the magnet 16 is disposed with the center thereof matching the center of gravity of the capsule 3. Accordingly, the magnetic field applied to the magnet 16 generates magnetic force or torque with the center matching the center of gravity of the capsule 3. This facilitates smooth propelling of the capsule 3 using a magnetic method.

Furthermore, the magnet 16 is disposed with the magnetic axis matching a predetermined direction of the image pickup device 14 as shown in FIG. 3B.

That is to say, the magnet 16 is disposed with the direction of the line drawn from S-pole to N-pole, matching the upper direction of the image captured by the image pickup device 14.

With the present embodiment, a rotational magnetic field is applied to the capsule 3 by the rotational magnetic field generating device 4. This rotates the magnet 16 using a magnetic method, thereby rotating the capsule 3 including the magnet 16 fixed therewithin. In this case, the helical protrusion 12 provided on the outer face of the capsule 3 is also rotated while being contact with the inner wall of the body cavity, thereby propelling the capsule 3.

Also, such an arrangement, in which the capsule 3 including the magnet 16 therein is controlled by the external magnetic field, has the advantage that the upper direction of the image is in what direction can be determined in an external coordinate system based upon the direction of the external magnetic field.

Furthermore, the capsule 3 includes: a signal processing circuit 20 for performing digital conversion of the signal captured by the image pickup device 14, and image compression of the digital signal thus converted; memory 21 for temporarily storing the image data in a form of digital data created and compressed by the signal processing circuit 20; a wireless communication circuit (an internal wireless communication device) 22 for high-frequency modulation of the image data read out from the memory 21 for wireless communication, demodulation of a control signal transmitted from the processing device 6, and so forth; a capsule control circuit 23 for controlling the illumination device 15 and the image pickup device 14, and control of each component within the capsule 3 such as the signal processing circuit 20 and so forth; a battery 24 for supplying electric power for actions of the electric system within the capsule 3 such as the signal processing circuit 20, as well as the objective optical system 13, the image pickup device 14, and the magnet 16, as described above. Wherein, the capsule control circuit 23 includes an image capturing timing controller.

On the other hand, the processing device 6, which performs wireless communication with the capsule 3, includes: a wireless communication circuit (an external wireless communication device) 25 for performing two-way wireless communication with the aforementioned wireless communication circuit 22; an image acquisition circuit 26, which is connected to the wireless communication circuit 25, for performing image rotation processing and so forth, as well as performing processing for transmitting a control signal to the capsule 3 for image capturing, and signal processing for image data transmitted from the capsule 3; and a magnetic field control circuit 27 for controlling the magnetic field generating control device 5 and so forth according to instructions input from the operation input device 8.

Furthermore, the processing device 6 includes: a storage circuit 28 for storing the state of the rotational magnetic field generated by the rotational magnetic field generating device 4 controlled by the aforementioned magnetic field generating control device 5, and more specifically, the direction of the normal vector of the rotational magnetic field (which will be simply referred to as "direction of magnetic field" hereafter) and the direction of the magnetic field forming the rotational magnetic field; and a setting circuit 29 which allows function setting and so forth through the function button 8c and so forth.

Furthermore, the processing device 6 includes: an image capturing timing detection circuit 30, which is connected to the image acquisition circuit 26, for detecting the timing of image capturing performed by the image pickup device 14 of the capsule 3; and a rotating angle acquisition circuit 31 for acquiring information regarding the rotating angle of the magnetic field controlled by the magnetic field control circuit 27 at the time of image capturing detected by the image capturing timing detection circuit 30. The rotating angle acquisition circuit 31 outputs the information regarding the rotating angle of the magnetic field thus acquired, to the image acquisition circuit 26 through the image capturing timing detection circuit 30, for example.

Then, the image acquisition circuit 26 performs rotation correction for the image data, which is captured by the rotating image pickup device 14 of the capsule 3, and which is acquired through the wireless communication circuit 25, based upon the information regarding the rotating angle of the magnetic field obtained from the rotating angle acquisition circuit 31, as well as image decompression processing.

The image acquisition circuit 26 performs image rotation processing for the images, which are captured by the image pickup device 14 and which are acquired through the wireless communication circuits 22 and 25, so as to form rotation-corrected images with a uniform predetermined rotating angle. That is to say, the images captured by the image pickup device 14 included within the capsule 3, which is rotated in image capturing, are subjected to the image rotation processing so as to obtain rotation-corrected images approximating those captured without rotation. The rotation-corrected images corresponding to a predetermined rotating angle are output and displayed on a display device 7.

On the other hand, the magnetic field control circuit 27 receives instruction signals corresponding to the operation through the direction input device 8a, the speed input device 8b, the function button 8c forming the operation input device 8. The magnetic field control circuit 27 performs control operation corresponding to instruction signals.

Furthermore, the magnetic field control circuit 27 is connected to the storage circuit 28. The storage circuit 28 stores the information regarding the directions of the rotational magnetic field and the magnetic field generated by the rotational magnetic field generating device 4 controlled by the magnetic field generating control device 5, at all times. Furthermore, the magnetic field control circuit 27 has a function for continuously changing the direction of the rotational magnetic field and the direction of the magnetic field according to the instruction operation for changing the direction of the rotational magnetic field or the direction of the magnetic field, thereby providing smooth change thereof. Note that the storage circuit 28 may be included within the magnetic field control circuit 27.

On the other hand, the magnetic field generating control device 5 connected to the magnetic field control circuit 27 includes an AC-current generating/control unit 33 formed of three AC-current generating/control circuits for controlling the frequency and the phase as well as generating AC current, and a driver unit 34 formed of three drivers for amplifying each AC current. The three driver output currents are supplied to three electromagnets 35a, 35b, and 35c which are components of the rotational magnetic field generating device 4, respectively.

With the present embodiment, the electromagnets 35a, 35b, and 35c are disposed so as to serve as magnets with three respective axes orthogonal one to another, as shown in FIG. 1. Here, each electromagnet generates a magnetic field along the axis thereof.

The present embodiment allows the operator to operate the direction input device 8a which is a component of the operation input device 8 shown in FIG. 4A for generating an instruction signal for controlling the direction of the magnetic field. Also, the present embodiment allows the operator to operate the speed input device 8b for generating an instruction signal for controlling the rotational frequency of the rotational magnetic field. Also, the present embodiment allows the operator to operate the function button 8c for generating eccentric rotational magnetic field.

Specifically, the operation input device 8 comprises: the direction input device 8a formed of a joystick Sa protruding upward from the upper face of an operation box, the speed input device 8b formed of a stick Sb; and the function button 8c formed of two buttons Ta and Tb, for example.

Figure 5A:
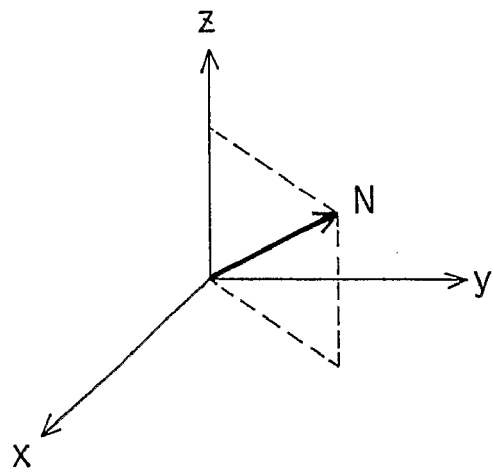
FIG. 5A is a diagram of a coordinate system showing the normal vector of the rotational magnetic field.

Now, let us consider the normal vector N of the rotation plane of the rotational magnetic field in a certain orthogonal coordinate system as shown in FIG. 5A. In this case, the direction of the normal vector N matches the propelling direction of the capsule 3. The propelling direction can be controlled by tilting operation of the joystick Sa.

Figure 5B:
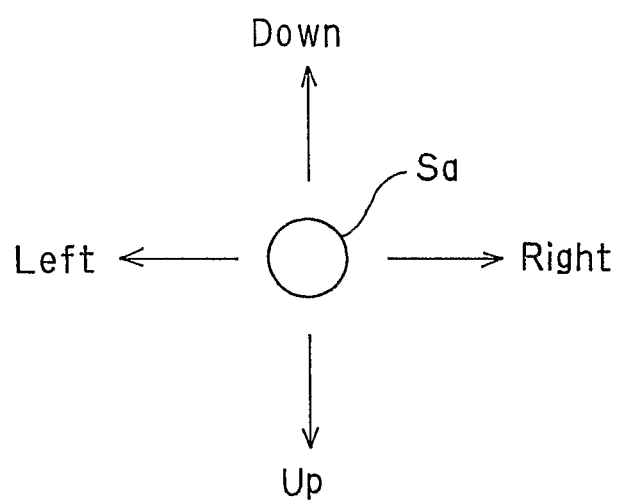
FIG. 5B is an explanatory diagram showing the propelling direction of the capsule in a case of tilting operation of a joystick.

Specifically, as shown in FIG. 5B, the present embodiment allows the operator to tilt the joystick Sa forward, backward, leftward, or rightward, so as to change the propelling direction to the front, back, left, or right. In this case, the degree of tilt of the joystick Sa corresponds to the rate of change in the turning angle. Note that it is needless to say that the present embodiment allows the operator to tilt the joystick to an intermediate direction (e.g., lower-left direction or upper-right direction) so as to change the propelling direction to the corresponding intermediate direction.

Figure 5C:
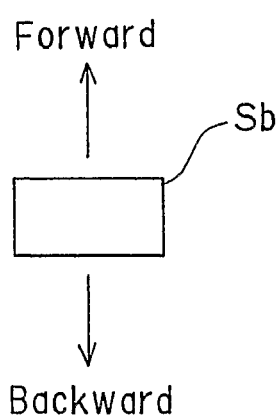
FIG. 5C is an explanatory diagram for describing the operation using the joystick, which allows switching of the rotating direction between the forward direction and the backward direction.

Furthermore, the present embodiment allows the operator to tilt the stick Sb forward/backward so as to set the rotation direction to the forward direction/backward direction, as shown in FIG. 5C. In this case, the rotational frequency is controlled by adjusting the tilt angle.

Furthermore, the present embodiment allows the operator to operate the button Ta for generating an instruction signal which requests initiation of generating an eccentric magnetic field, thereby generating a rotational magnetic field with an eccentric path (i.e., generating a rotational magnetic field with an eccentric axis displaced from a given direction by an eccentric angle, whereby the direction of the rotational magnetic field changes along the corresponding conical face). The eccentric rotational magnetic field starts so-called jiggling or precession of the magnet 16 included within the capsule 3 (i.e., the magnet 16 is rotated with the jiggling axis, like a rotating top).

That is to say, the button Ta has a function for generating an instruction signal to initiate the jiggling. On the other hand, the button Tb has a function for generating an instruction signal to stop the jiggling. Note that the setting circuit 29 has a function which allows the operator to set the magnitude of the magnetic field, and the jiggling angle (angle "Φ" which will be described later) and the jiggling frequency, beforehand.

Also a modification of the operation input device 8 shown in FIG. 4A may be made as shown in FIG. 4B, which includes: a lever La which is tiltably provided on the top of the joystick Sc and which allows the operator to change the rotational frequency of the rotational magnetic field by adjusting the tilt amount, thereby enabling the operator to change the rotational speed of the capsule 3; a button Tc which allows the operator to select the rotating direction of the rotational magnetic field by ON/OFF actions; and a function button Td which allows the operator to switch to the eccentric rotational magnetic field (with an arrangement including the single function button Td, the single function button Td has a switching function for both switching actions "OFF" to "ON" and "ON" to "OFF").

Such an arrangement allows one-handed operation, thereby improving ease of use as compared with the arrangement shown in FIG. 4A which requires two-handed operation.

Also, a modification of the operation input device 8 shown in FIG. 4A may be made further including a foot switch F shown in FIG. 4C instead of the stick Sb, which allows the operator to control the rotational frequency by adjusting the amount of pressure applied to the foot switch F.

Figure 6A:
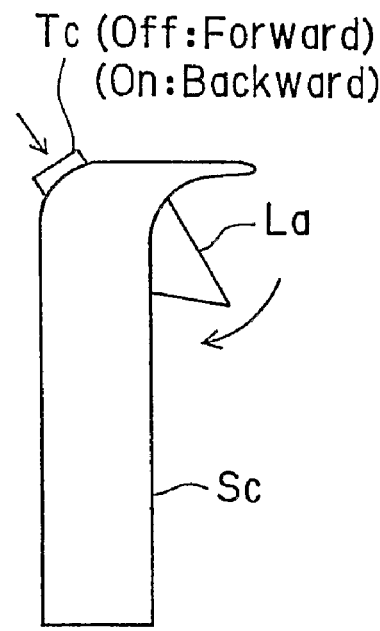
FIG. 6A is a diagram showing a joystick according to a modification.
Figure 6B:
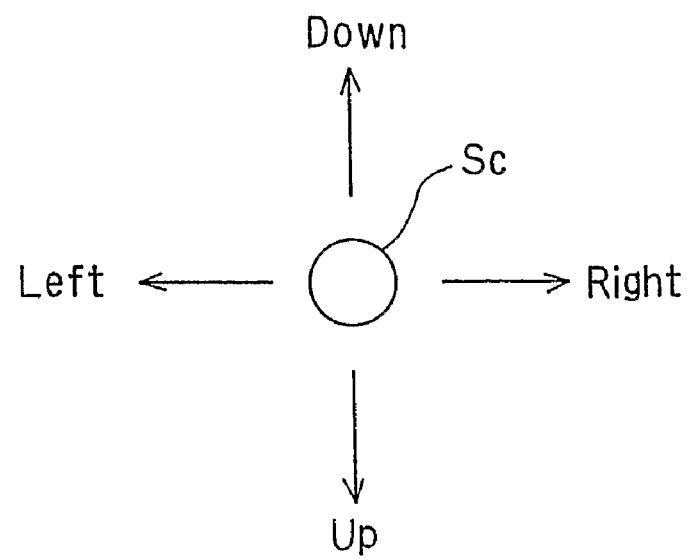
FIG. 6B is an explanatory diagram showing the propelling direction of the capsule in a case of tilting operation of the joystick shown in FIG. 6A.

FIGS. 6A through 6C are diagrams for describing the operation and functions of an arrangement employing the joystick Sc shown in FIG. 4B. FIG. 6A shows a configuration example having the same configuration as that shown in FIG. 4B, except for including no function button Td. FIG. 6B shows a function for controlling the propelling direction by tilting operation of the joystick Sc. FIG. 6C is a diagram for describing the actual operation for controlling the propelling direction of the capsule 3 and so forth.

The present embodiment allows the operator to perform tilting operation of the joystick Sc shown in FIG. 6A for controlling the direction of the generated rotational magnetic field. Thus, the present embodiment has a function for controlling the propelling direction of the capsule 3 as shown in FIG. 6B. That is to say, the present embodiment has a function for controlling the direction of the generated rotational magnetic field so as to propel the capsule 3 in a direction determined by tilting operation of the joystick Sc as shown in FIG. 6B (or FIG. 5B).

Furthermore, the present embodiment allows the operator to control the rotational frequency by adjusting the tilt amount of the lever La. Furthermore, the present embodiment allows the operator to switch the propelling direction. Specifically, upon pressing the button Tc in the OFF state, the direction of the rotational magnetic field is switched so as to propel the capsule 3 in the forward direction. On the other hand, upon pressing the button Tc in the ON state, the direction of the rotational magnetic field is switched (to the reverse direction) so as to propel the capsule 3 in the backward direction.

In order to realize smooth control of the propelling direction as shown in FIG. 6B, there is the need to detect the state of the capsule 3 or the state of the rotational magnetic field at all times. With the present embodiment, the storage circuit 28 stores the state of the rotational magnetic field (specifically, the direction of the rotational magnetic field and the direction of the magnetic field) at all times.

Specifically, the operation instruction signal output from the operation input device 8 serving as first operation input means shown in FIG. 2 is input to the magnetic field control circuit 27. The magnetic field control circuit 27 outputs an instruction signal to the magnetic field generating control device 5 for generating a rotational magnetic field according to the instruction signal, as well as storing the information regarding the direction of the rotational magnetic field and the direction of the magnetic field in the storage circuit 28.

Thus, the storage circuit 28 stores the information regarding the direction of the rotational magnetic field and the direction of the magnetic field, which are generated by the rotational magnetic field generating device 4, at all times. Here, the rotational magnetic field is formed by generating a magnetic field which changes in a cyclic manner.

Note that the present invention is not restricted to such an arrangement in which the storage circuit 28 stores the information corresponding to the control signal for controlling the direction of the rotational magnetic field and the direction of the magnetic field received from the magnetic field control circuit 27. Also, an arrangement may be made in which the magnetic field generating control circuit 5 transmits the information, which determines the actual direction of the rotational magnetic field and the actual direction of the magnetic field output from the rotational magnetic field generating device 4 through the AC-current generating/control unit 33 and the driver unit 34 according to a control signal output from the magnetic field control circuit 27 to the magnetic field generating control device 5, to the magnetic field control circuit 27, and the storage circuit 28 stores the information thus received.

Furthermore, the present embodiment has a function for continuously controlling changes in the rotational magnetic field, in a case of starting application of the rotational magnetic field, stopping application of the rotational magnetic field, and changing the direction of the rotational magnetic field (i.e., the change in the propelling direction of the capsule). This enables smooth application of force to the capsule 3 without rapid application thereof.

Such control ensures smooth movement of the capsule 3 even at the time of starting application of the rotational magnetic field, and stopping application of the rotational magnetic field.

With the present embodiment, when the capsule 3. serving as a medical device main unit is guided using the rotational magnetic field, the information regarding the state of the rotational magnetic field which determines the current propelling direction of the capsule 3 is stored in the storage circuit 28. Furthermore, in a case of changing the propelling direction, the rotational magnetic field is controlled so as to continuously change with reference to the current information stored in the storage circuit 28, thereby propelling the capsule 3 in the next direction. Such control enables guiding operation for the medical device main unit while maintaining smooth movement thereof.

Furthermore, the storage circuit 28 may store the information regarding the rotational magnetic field in a form correlated with the time. Such an arrangement can provide high-precision information regarding the rotational magnetic field according to the need for the information regarding the previous (past) rotational magnetic field prior to the point in time of detection of image capturing, as described in the following embodiments.

With the present embodiment, the capsule 3 is propelled within the body cavity by rotational driving thereof. Accordingly, the raw images captured by the capsule 3 are rotating images. With the present embodiment, the rotating images are subjected to image rotation processing, i.e., the images are corrected so as to correspond to predetermined rotating angle so as to create images of a uniform orientation which correspond to those that would be captured without rotation, i.e., captured with a uniform rotating angle at all times. Then, the corrected images are displayed on the display device 7.

With the present embodiment, the image acquisition circuit 26, which is a component of the apparatus outside of the subject's body, transmits an image-capturing request signal for instructing the capsule 3 to capture an image. The capsule 3 captures an image according to the image-capturing request signal.

Furthermore, at the time of transmission of the image-capturing request signal, the image acquisition circuit 26 transmits an image-capturing (request) transmission timing signal to the image capturing timing detection circuit 30. The image capturing timing detection circuit 30 detects the timing signal as image-capturing timing.

Immediately upon receiving the timing signal, the image capturing timing detection circuit 30 transmits rotating angle information output request signal to the magnetic field control circuit 27 for outputting the rotating angle information which determines the rotation of the capsule 3 due to the rotational magnetic field at this point in time. The magnetic field control circuit 27 outputs the rotating angle information according to the rotating angle information output request signal.

As described above, the capsule 3 includes the magnet 16 with the direction of the magnetic axis matching a predetermined direction of the image-capturing device 14. With such an arrangement, the direction of the magnetic axis of the magnet 16 follows the direction of the magnetic field. This enables the image-capturing direction of the image-capturing device 14 of the capsule 3, i.e., the direction of the captured image, to be determined. Furthermore, this enables the rotating angle of the captured image, which represents the degree of rotation of the image with respect to a predetermined reference angle, to be determined.

The rotating angle acquisition circuit 31 acquires the information regarding the rotating angle (the capsule 3 is rotated by the rotational magnetic field generated by the rotational magnetic field generating device 4) output from the magnetic field control device 27, i.e., the rotating angle information. The rotating angle acquisition circuit 31 holds the rotating angle information thus acquired. Upon the image acquisition circuit 26 receiving the image data, the rotating angle acquisition circuit 31 transmits the rotating angle information to the image acquisition circuit 26 (through the image capturing timing detection circuit 30 or directly).

Then, the image acquisition circuit 26 performs image rotation processing for the received image data by a rotating angle determined based upon the rotating angle information, thereby acquiring (creating) a rotation-corrected image. The rotation-corrected image is displayed on the display device 7. Thus, the display device 7 displays an image without rotation (with the same predetermined rotating angle) at all times. This allows the user to observe the images without concern for rotation of the images, like those would be captured by the capsule 3 without rotation (which facilitates observation).

Description will be made regarding the operation of the present embodiment having such a configuration.

First, description will be made regarding schematic operation according to the present embodiment. The subject swallows the capsule 3 for examination of the body cavity. While the capsule 3 inserted into the body cavity passes through the body cavity such as the esophagus and so forth, image capturing is performed by the image-capturing device 14, and illumination is performed by the illumination device 15, synchronously with the image capturing request signal transmitted from the processing device 6. The image captured by the image-capturing device 14 is subjected to image compression by the signal processing circuit 20, following which the compressed image data is transmitted to the processing device 6 outside of the subject's body wirelessly through the wireless communication circuit 22.

The processing device 6 receives the image data with the wireless communication circuit 25, and demodulated image data is transmitted to the image acquisition circuit 26. The image acquisition circuit 26 performs decompression processing, image rotation processing, and interpolation processing for the image data, as well as storing the image data in an image storage device (such as memory or a hard disk) included therewithin, thereby creating an image which has been subjected to such processing.

The display device 7 receives the images thus processed, thereby displaying the images sequentially captured by the capsule 3 with a stationary rotating angle (reference rotating angle).

Next, detailed description will be made regarding the operation from the stage where the image is captured by the capsule 3 up to the stage where the captured image subjected to rotation correction is displayed, with reference to FIG. 7. Note that in FIG. 7, the downward direction represents the elapsed time. The same can be said of other timing charts such as FIGS. 9, 11, 13, 15, and so forth.

Figure 7:
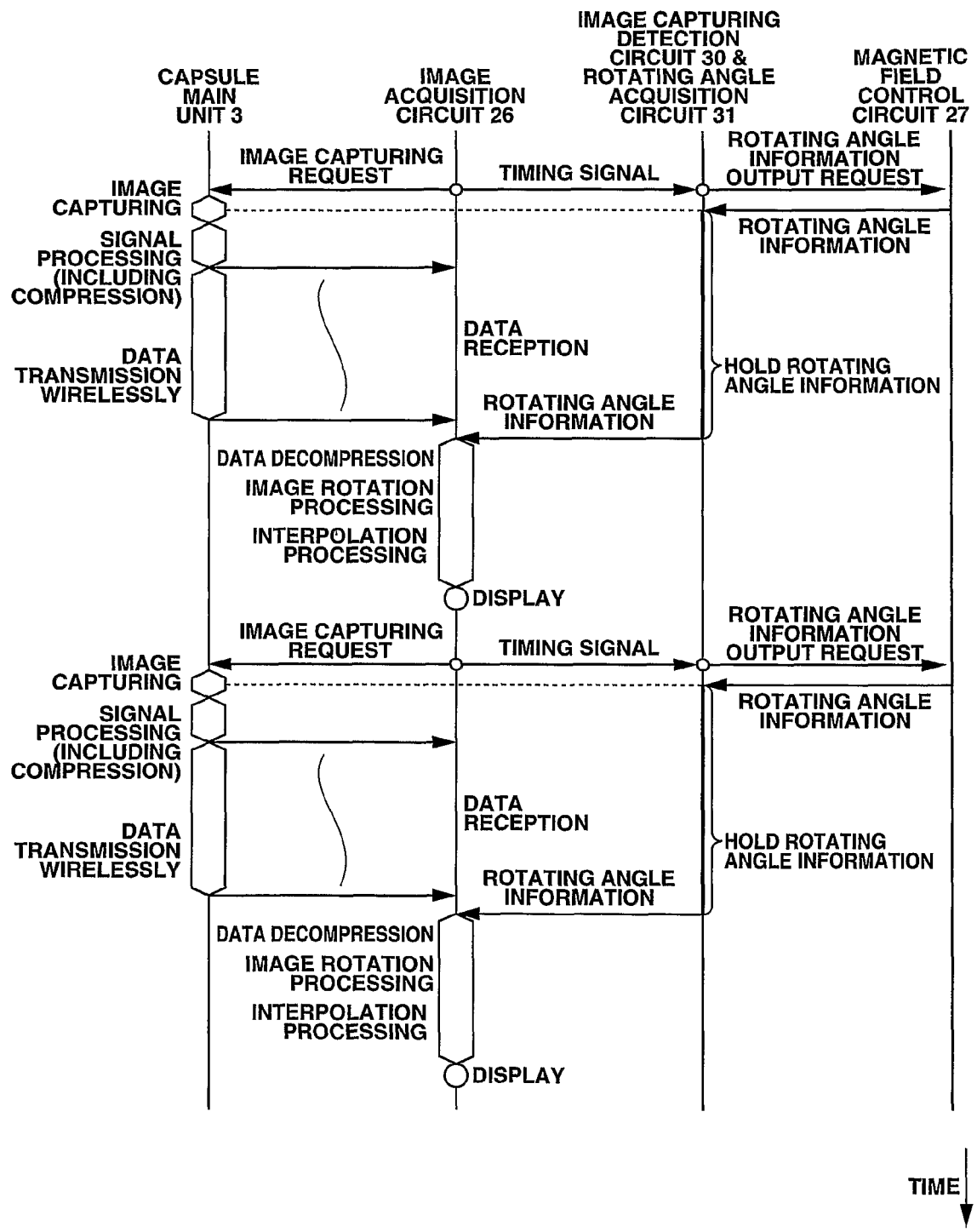
FIG. 7 is a timing chart showing the operation of the present embodiment.

As shown in FIG. 7, the image acquisition circuit 26 of the processing device 6 transmits the image capturing request signal to the capsule 3 through the wireless communication circuit 25 as well as transmitting the timing signal to the image capturing timing detection circuit 30 at the same time, synchronously with a predetermined image-capturing cycle.

In the capsule 3, the capsule control circuit 23 acquires the image capturing request signal through the wireless communication circuit 22. Then, the image capturing timing controller of the capsule control circuit 23 instructs the illumination device 15 to perform illumination as well as applying a driving signal to the image pickup device 14, according to the image capturing request signal, thereby outputting the captured image signal representing the portion illuminated by the illumination device 15.

The captured image signal is subjected to signal processing by the signal processing circuit 20. Furthermore, the image signal is subjected to A/D conversion, following which the image data is subjected to image compression. Then, the compressed image data is stored in the memory 21. The compressed image data stored in the memory 21 is modulated by the wireless communication circuit 22, and the modulated image data is transmitted wirelessly. The transmitted image data is demodulated and acquired (received) by the image acquisition circuit 26 through the wireless communication circuit 25 of the processing device 6 outside of the subject's body.

On the other hand, the image capturing timing detection circuit 30 detects the timing signal as image-capturing timing. Immediately upon receiving the timing signal, the image capturing timing detection circuit 30 transmits a rotating angle information output request signal to the magnetic field control circuit 27 for acquiring the information regarding the rotational magnetic field at that point in time. The magnetic field control circuit 27 outputs the information regarding the rotating angle of the rotational magnetic field with respect to the time of input of the aforementioned signal to the rotating angle acquisition circuit 31.

Note that FIG. 7 shows an arrangement giving consideration to a delay time elapsed from transmission of the image capturing request signal up to actual image capturing performed by the image pickup device 14. That is to say, FIG. 7 shows an arrangement in which the magnetic field control circuit 27 outputs the information regarding the rotating angle acquired after a period of time corresponding to the delay time elapsed from the input of the rotating angle output request signal. Thus, the rotating angle information is output from the magnetic field control circuit 27 with respect to the time of the middle of the image-capturing period as indicated by the dashed line in FIG. 7.

Note that the present invention is not restricted to such an arrangement in which the magnetic field control circuit 27 compensates for such delay time elapsed from transmission of the image-capturing request signal up to the actual image capturing. Also, an arrangement may be made in which the image capturing timing detection circuit 30 transmits the rotating angle information output request signal to the magnetic field control circuit 27 after the aforementioned delay time elapsed from the transmission of the image capturing request.

Also, in a case that the period of time from the image-capturing request up to the actual image capturing is short, an arrangement may be made in which the rotating angle information is output without giving consideration to the aforementioned delay time.

The rotating angle acquisition circuit 31 holds the rotating angle information output from the magnetic field control circuit 27, and outputs the rotating angle information to the image acquisition circuit 26 at the time of completion of acquisition of image data transmitted from the capsule 3 by the image acquisition circuit 26, for example.

The aforementioned image acquisition circuit 26 performs decompression processing for the compressed image data thus acquired. Subsequently, the image acquisition circuit 26 performs image rotation processing in which the image acquired by the rotating image-capturing device is corrected into an image oriented according to a reference rotating angle, as well as interpolation processing involved for the rotation-corrected image as appropriate, thereby creating an image to be displayed on the display device 7. Then, the image acquisition circuit 26 outputs the image thus created, to the display device 7.

The display device 7 displays the image output from the image acquisition circuit 26, i.e., the image captured by the image-capturing device 14 in the form of a rotation-corrected image in which adverse effects due to rotation have been corrected. For example, the display device 7 displays the image with the upper direction of the image-capturing device 14 as the upper direction of the image thus displayed, thereby facilitating observation.

After a predetermined period of time, the image acquisition circuit 26 transmits the image capturing request signal to the capsule 3 as well as transmitting the timing signal to the image capturing timing detection circuit 30 at the same time, again. The aforementioned processing is repeated.

Figure 8:
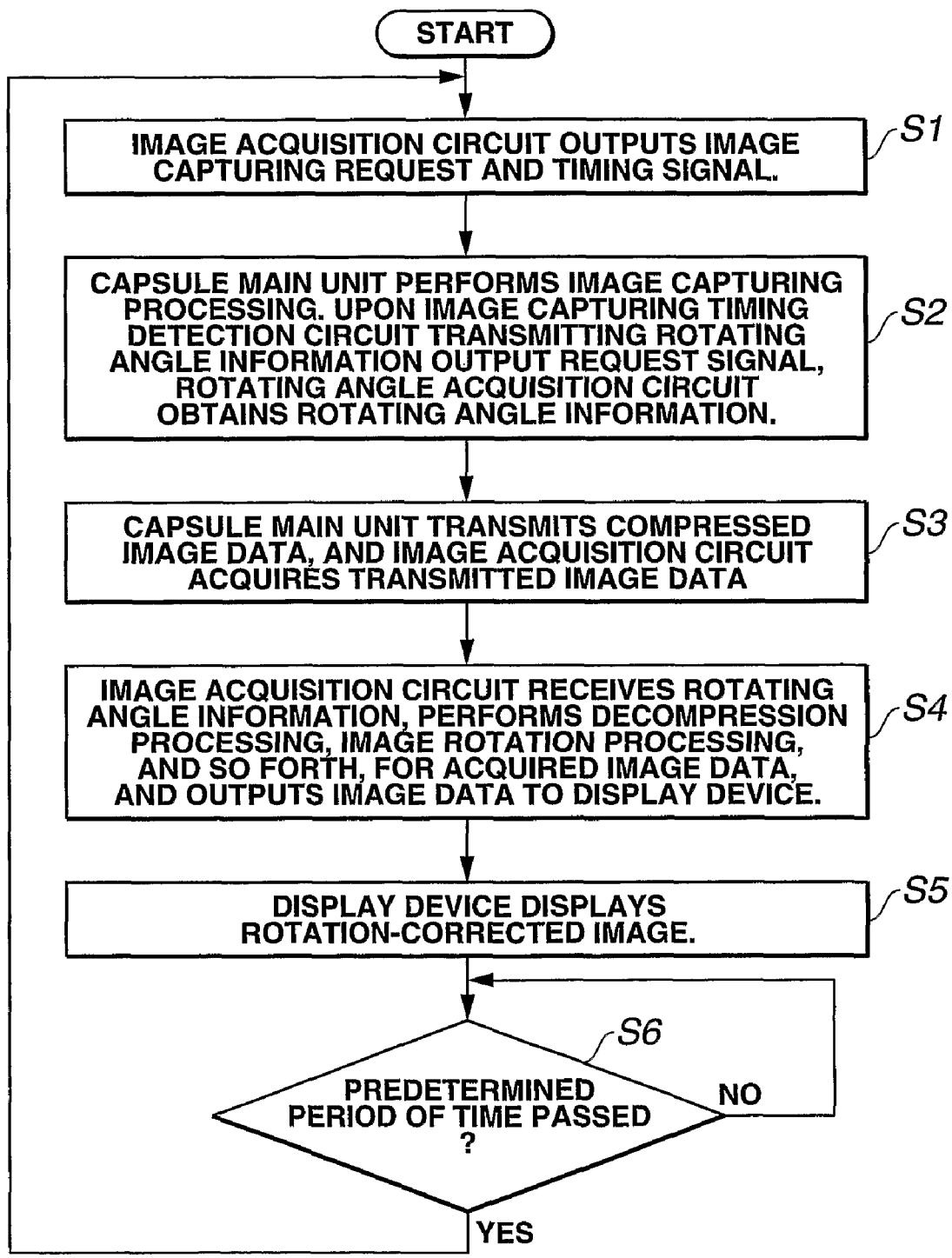
FIG. 8 is a flowchart showing the operation of the present embodiment.

FIG. 8 is a flowchart which shows the processing shown in FIG. 7.

In Step S1, the image acquisition circuit 26 transmits the image capturing request signal to the capsule 3 through the wireless communication circuit 25 as well as outputting the timing signal to the image capturing timing detection circuit 30. The image capturing timing detection circuit 30 detects the timing signal as image-capturing timing.

As shown in Step S2, upon receiving the image capturing request signal, the capsule 3 instructs the illumination device 15 to perform illumination, and performs image capturing processing using the image pickup device 14. Furthermore, upon detection of the timing signal, the image capturing timing detection circuit 30 transmits a rotating angle information output request signal to the magnetic field control circuit 27. The rotating angle acquisition circuit 31 acquires the rotating angle information at the time of transmission of the signal (or at the time after a period of time corresponding to the delay time elapsed from image-capturing request up to actual image capturing).

As shown in Step S3, the capsule 3 transmits the image data captured in the image-capturing processing. The image acquisition circuit 26 acquires the image data thus transmitted.

Then, as shown in Step S4, the image acquisition circuit 26 receives the rotating angle information transmitted from the rotating angle acquisition circuit 31, and performs decompression processing for compressed image data, image rotation processing, and interpolation processing, for the acquired image data. The image data thus processed is output to the display device 7.

As shown in Step S5, the display device 7 displays the image input from the image acquisition circuit 26, thereby displaying the rotation-corrected image without rotation thereof.

Then, as shown in Step S6, the image acquisition circuit 26 determines whether or not a predetermined period of time has passed (with reference to output of a timer of the image capturing timing detection circuit 30). After the predetermined time of period, the flow returns to Step S1 where the image capturing request signal is transmitted to the capsule 3 as well as transmitting the timing signal to the image capturing timing detection circuit 30 at the same time. The aforementioned processing is repeated.

Thus, the image acquisition circuit 26 performs image rotation processing for the image captured by the image pickup device 14 in the actual image capturing, i.e., the image is rotated by appropriate rotating angle, using the high-precision rotating angle information with respect to the point in time of image capturing or the image capturing timing. Then, the display device 7 displays each image with a uniform predetermined rotating angle.

Thus, with the present embodiment, while image is captured by the rotating image pickup device 14, the point in time at which the actual image capturing is performed by the image pickup device 14 is detected, and the rotating angle information regarding the rotational magnetic field is detected with respect to the time thus detected. This enables the display device 7 to display a high-precision rotation-corrected image without rotation with a simple configuration.

This allows the observer to observe the image orientated according to a uniform predetermined rotating angle without the concern for rotation. This facilitates observation as well as facilitating the operation such as change of the propelling direction and so forth since the image is displayed with a uniform rotating angle.

Furthermore, the present embodiment has a function of detecting the point in time of image capturing without being affected by the time required for image compression, even in a case of involving image compression performed by the capsule 3. This enables higher-precision rotation correction based upon the point of time of image capturing than conventional arrangements in which rotation-correction is performed for the image based upon the information with respect to the point of time of receiving the image.

Furthermore, with the present embodiment, the image-capturing timing is controlled by transmitting a signal from the processing device 6 positioned outside of the subject's body wirelessly, thereby allowing control such as capturing of a desired number of images of a desired portion and so forth.

Figure 9:
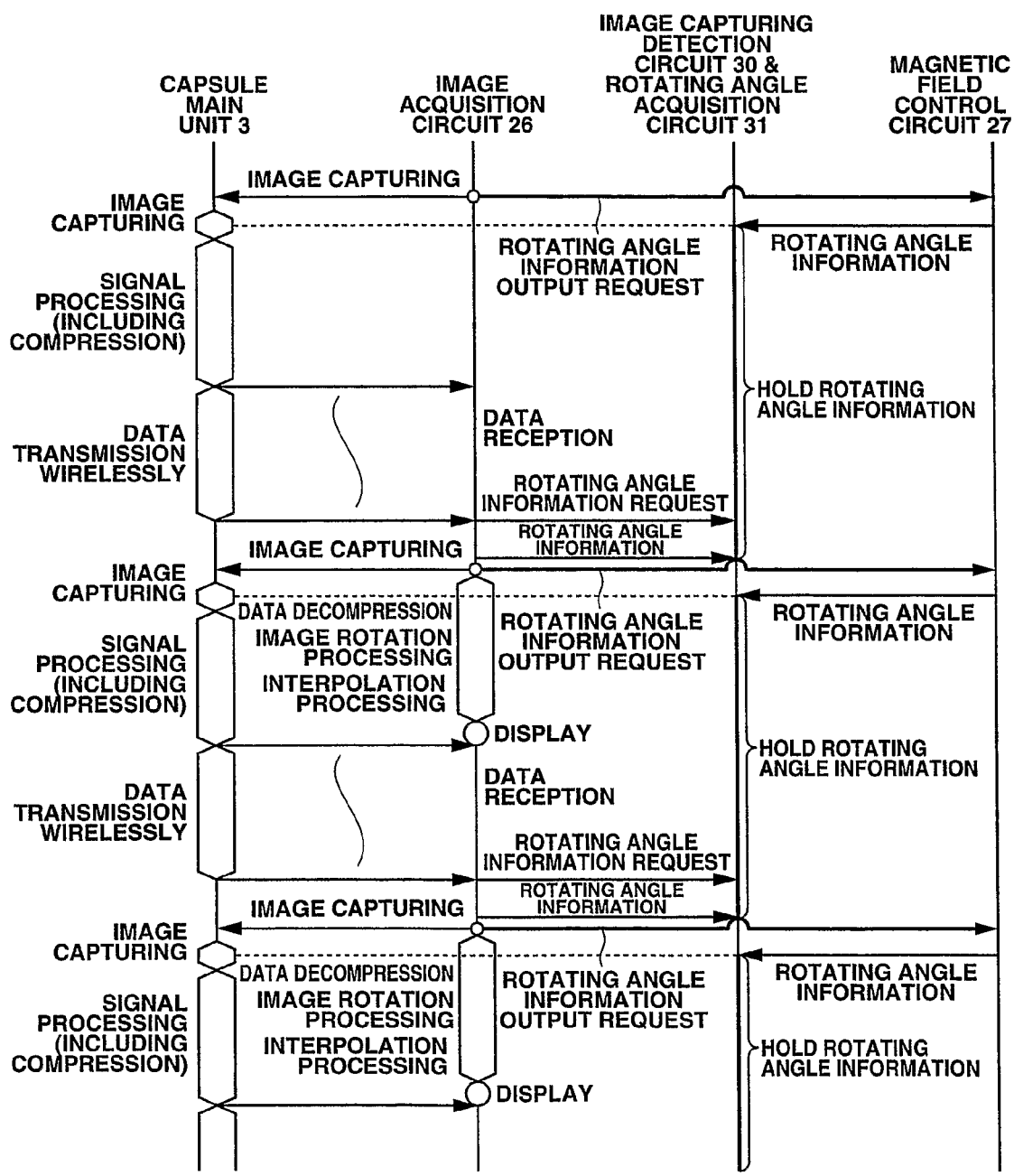
FIG. 9 is a timing chart showing the operation of the modification.

Next, description will be made regarding a modification of the present embodiment with reference to a timing chart shown in FIG. 9. The present modification has generally the same hardware configuration as that shown in FIGS. 1 and 2. The difference is that at the time of transmission of the image capturing request to the capsule 3, the image acquisition circuit 26 directly transmits the rotating angle information request signal to the magnetic field control circuit 27, and the rotating angle information output from the magnetic field control circuit 27 at that time (or at the time after the delay time elapsed from the image capturing request up to actual image capturing) is held by the rotating angle acquisition circuit 31.

Furthermore, with the present modification, the image acquisition circuit 26 transmits the rotating angle information request signal to the rotating angle acquisition circuit 31 for requesting the rotating angle information at the time of completion of reception of the image data transmitted from the capsule 3, and receives the rotating angle information held by the rotating angle acquisition circuit 31.

Then, the image acquisition circuit 26 transmits the image capturing request to the capsule 3 immediately prior to the start of the decompression processing and so forth for the compressed image data, as well as transmitting the rotating angle information output request signal to the magnetic field control circuit 27.

That is to say, with the embodiment 1, the image acquisition circuit 26 transmits the image capturing request to the capsule 3 after completion of the decompression processing and so forth for the compressed image data. On the other hand, with the present modification, the image acquisition circuit 26 transmits the image capturing request to the capsule 3 immediately prior to the decompression processing and so forth for the compressed image data.

This enables the capsule 3 to perform image capturing and signal processing in parallel with the image acquisition circuit 26 performing the decompression processing and so forth for the compressed image data. This reduces the cycle time of image capturing as compared with the embodiment 1.

The present modification allows image capturing with a shorter cycle time. In other words, the present modification improves the frame rate of image capturing as well as reducing the cycle time of display of the rotation-corrected images thus captured, thereby displaying images approximating the effect of moving images. Note that the present modification has the same advantages as with the embodiment 1, in addition to the aforementioned advantages.

Note that with the present embodiment (including the modification) and the following embodiments, the image capturing timing detection circuit 30 and the rotating angle acquisition circuit 31 within the processing device 6 may be replaced by a single unit having the same functions.

Embodiment 2

Figure 10:
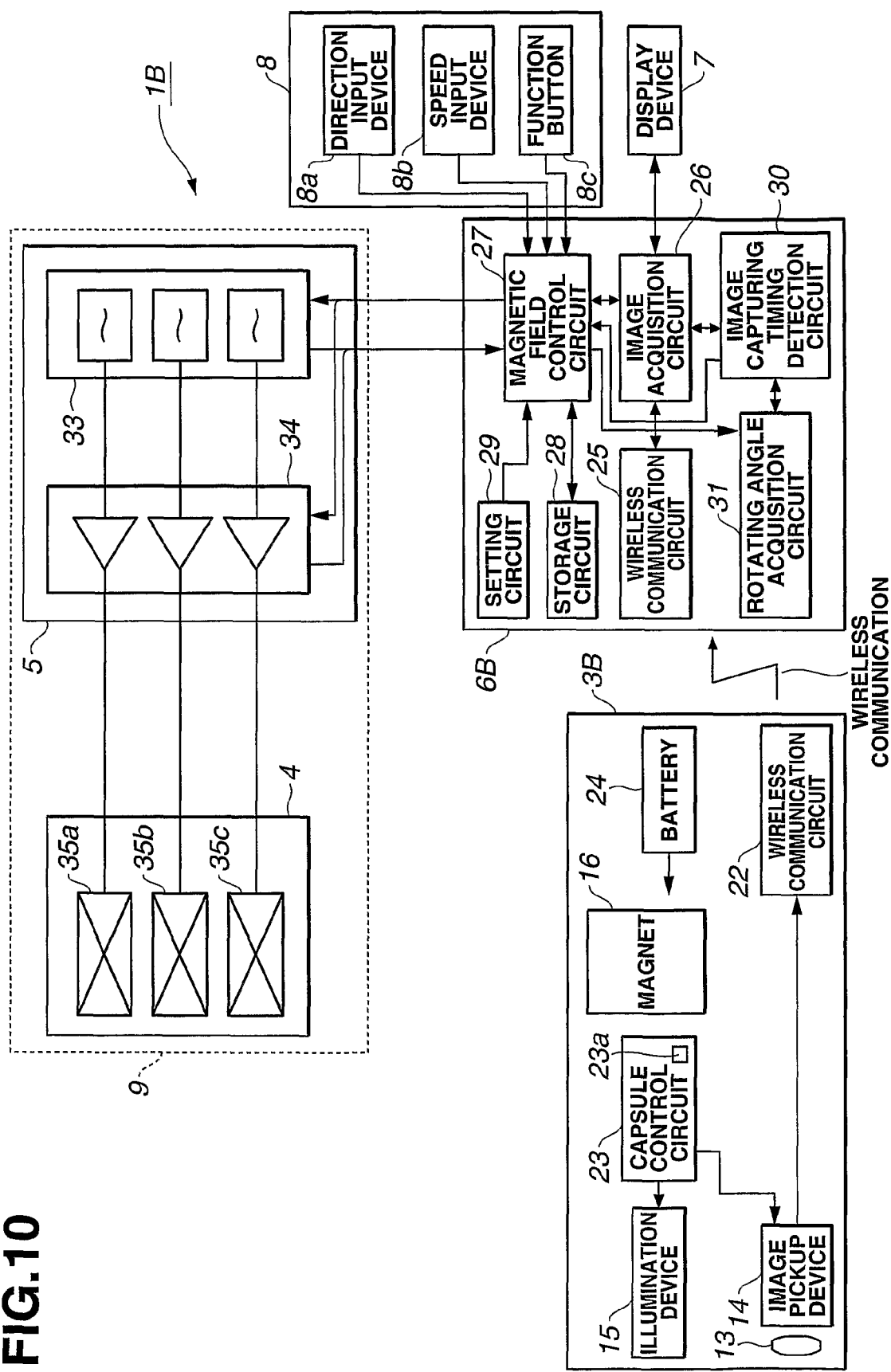
FIG. 10 is a block diagram showing an internal configuration of the components of a capsule medical system according to an embodiment 2 of the present invention.
Figure 11:
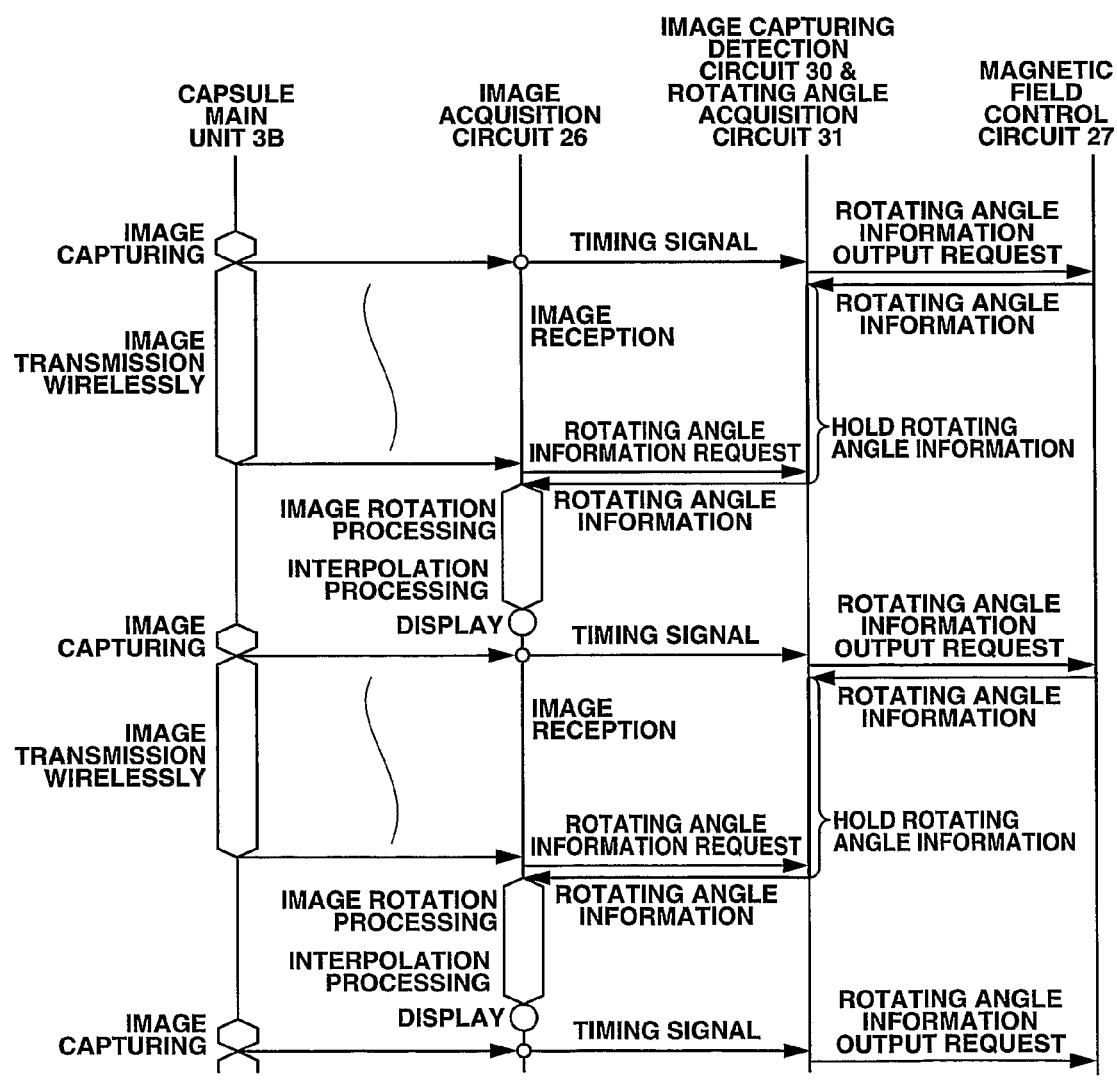
FIG. 11 is a timing chart showing the operation of the present embodiment.

Next, description will be made regarding an embodiment 2 according to the present invention with reference to FIGS. 10 and 11. FIG. 10 shows a configuration of a capsule medical system 1B according to the embodiment 2 of the present invention.

The capsule medical system 1B comprises: a capsule 3B; the magnetic field generating apparatus 9; a processing device 6B; the display device 7; and the operation input device 8.

The capsule 3B has generally the same configuration as that of the capsule 3 shown in FIG. 2, except for a configuration in which the captured image signal captured by the image pickup device 14 is transmitted in the form of an analog signal modulated by the wireless communication circuit 22. That is to say, the capsule 3B has generally the same configuration as that shown in FIG. 2, except for not including the signal processing circuit 20 for A/D conversion, image-data compression, and so forth, and the memory 21.

Furthermore, the capsule control circuit 23 includes a timer 23a for controlling the illumination device 15 and the image pickup device 14, thereby enabling the capsule 3B to perform image capturing at a predetermined cycle. That is to say, the capsule control circuit 23 has a function serving as an image capturing controller for controlling the image-capturing timing of the image pickup device 14.

Furthermore, with the present embodiment, the capsule 3B has only a function for transmitting the captured image with the ratio communication circuit 22, and has no function for receiving any signal.

On the other hand, the processing device 6B receives the image transmitted from the capsule 3B. In this case, the processing device 6B generates a timing signal, which employs the point in time at which the first portion of the image data has been received as the point in time of image capturing. The processing device 6B acquires the rotating angle information from the magnetic field control circuit 27 according to the timing signal. Then, the processing device 6B performs image-rotation processing and interpolation processing for the received image. That is to say, the processing device 6B performs rotation-correction for the image received from the capsule 3B, and outputs the rotation-corrected image to the display device 7.

Note that the processing device 6B detects the point in time of image capturing as being the point in time at which the processing device 6B has received the image transmitted wirelessly. Accordingly, in order to improve the detection precision of the point in time of image capturing, an arrangement may be made in which the processing device 6B instructs the magnetic field control circuit 27 to output the rotating angle information with respect to a point in time prior to the wireless communication corresponding to the delay time.

The other components are the same as those shown in FIG. 2. Next, description will be made regarding the operation of the present embodiment with reference to a timing chart shown in FIG. 11.

With the present embodiment, the capsule 3 performs image capturing with a constant cycle. Then, the image captured by the image pickup device 14 is subjected to high-frequency modulation by the wireless communication circuit 22. The modulated images are sequentially transmitted wirelessly. With the processing device 6B, the transmitted images are demodulated by the wireless communication circuit 25, and the demodulated images are sequentially transmitted to the image acquisition circuit 26. The image is received by (input to) the image acquisition circuit 26 trough the wireless communication circuit 25. Upon detecting the first portion of the image thus received, the image acquisition circuit 26 transmits a timing signal to the image capturing timing detection circuit 30. With such an arrangement in which the first portion of the image is detected, a mark may be added to the first portion of the image, thereby facilitating the detection of a first portion thereof. Also, an arrangement may be made in which the first portion is detected by making a comparison between the input signal and a predetermined threshold using a comparator or the like without involving such a mark.

Immediately upon receiving the timing signal, the image capturing timing detection circuit 30 detects the timing signal as image-capturing timing, and transmits a rotating angle information output request signal to the magnetic field control circuit 27. The magnetic field control circuit 27 outputs the rotating angle information regarding the point in time of input of the signal, and the rotating angle acquisition circuit 31 acquires this rotating angle information.

On the other hand, immediately upon detecting end of the image reception, the image acquisition circuit 26 transmits a rotating angle information request signal to the rotating angle acquisition circuit 31 for requesting the rotating angle information thus held (by the rotating angle acquisition circuit 31), thereby acquiring the rotating angle information. With such an arrangement in which the end of image reception is detected, a mark may be added to the end portion of the image data in the same way as described above.

Upon acquiring the rotating angle information, the image acquisition circuit 26 performs image rotation processing and interpolation processing, thereby creating a video signal which can be displayed on the display device 7. The video signal thus created is input to the display device 7. Thus, the display device 7 displays a rotation-corrected image.

Following end of the video signal creation by the image acquisition circuit 26, the capsule 3 performs the next image capturing operation. Then, the aforementioned processing is repeated.

With the present embodiment, the capsule 3 performs image capturing while passing through the body cavity without control of external circuits. On the other hand, the processing device 6B outside of the subject's body receives an image transmitted from the capsule 3B. At that time, the rotating angle information is acquired from the magnetic field control circuit 27 with the point in time of detection of the first portion of the received image as the point in time of image capturing. Then, image rotation processing is performed based upon the rotating angle information thus acquired. This enables display of images without rotation with a simple configuration.

Also, in order to solve the problem that there is a delay time elapsed from the point in time of detection of the first portion of the received image up to the point in time of actual image capturing, an arrangement may be made which acquires the rotating angle information with respect to a point in time prior to the detection time by the aforementioned delay time, thereby enabling display of a high-precision rotation-corrected image.

Embodiment 3

Figure 12:
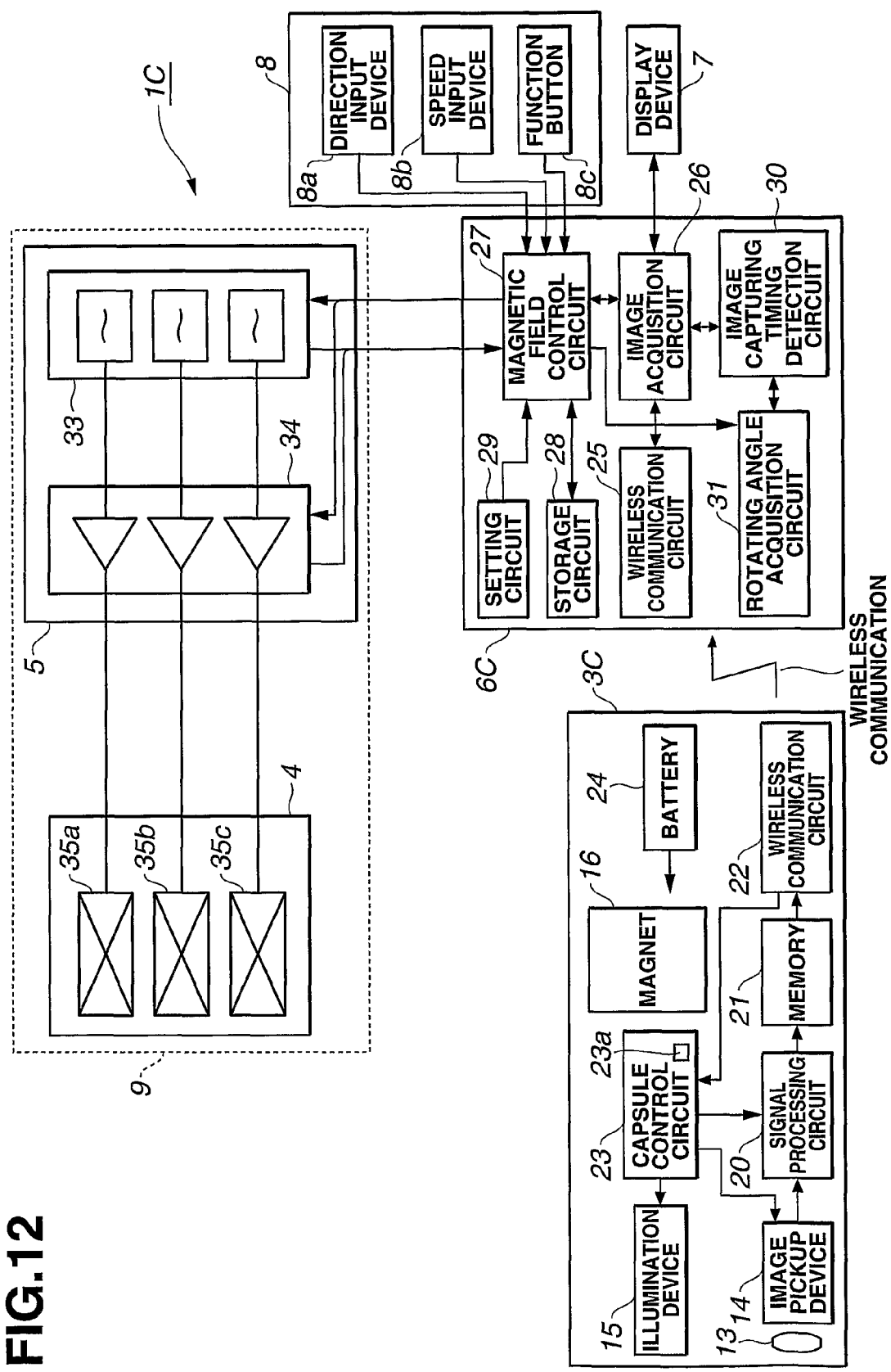
FIG. 12 is a block diagram showing an internal configuration of the components of a capsule medical system according to an embodiment 3 of the present invention.

Next, description will be made regarding an embodiment 3 according to the present invention with reference to FIGS. 12 and 13. FIG. 12 shows a configuration of a capsule medical system 1C according to the embodiment 3 of the present invention.

While the capsule 3C according to the present embodiment has only a function for transmitting the captured image in the same way as the capsule 3B shown in FIG. 10, the capsule 3C includes the signal processing circuit 20 and the memory 21, and transmits the compressed image data in the same way as the embodiment 1.

Furthermore, with the present embodiment, after a predetermined period of time following transmission of the compressed image data, the next image capturing is started. That is to say, the capsule 3C performs the next image-capturing operation in parallel with the operation of the processing device 6C for performing decompression of compressed image data and so forth.

Furthermore, the capsule control circuit 23 includes the timer 23a therewithin in the same way as with that shown in FIG. 10. Following the step from the start of image capturing performed by the image pickup device 14 up to the image processing including compression, the image is transmitted after a predetermined period of time t0 from the time at which the image pickup device 14 has performed image capturing.

That is to say, the image is always transmitted after a predetermined period of time t0 from the point in time at which the image pickup device 14 has started image capturing, or from the middle point of the image capturing time, even in a case of change in a period of time required for image compression.

On the other hand, with the processing device 6C for receiving the image thus transmitted, upon detecting the first portion of the transmitted image, the image acquisition circuit 26 transmits a rotating angle information output request signal to the magnetic field control circuit 27. In this case, the image acquisition circuit 26 transmits the rotating angle information output request signal to the magnetic field control circuit 27 for outputting the rotating angle information with respect to a point in time prior to the transmission of the request signal by the predetermined period of time t0.

The magnetic field control circuit 27 reads out the past rotating angle information with respect to the point in time prior to reception of the signal by the predetermined period of time t0, from the storage circuit 28, and outputs the past rotating angle information thus read out.

The image acquisition circuit 26 performs image rotation processing based upon the rotating angle information with respect to a point in time prior to the transmission of the request signal by the predetermined period of time t0. In order to provide such a function, with the present embodiment, the storage circuit 28 connected to the magnetic field control circuit 27 stores the past rotating angle information at all times with respect to at least a period from the past point in time prior to the current time by the predetermined period of time t0. Also, an arrangement may be made in which the image acquisition circuit 26 transmits the rotating angle information output request signal to the storage circuit 28 for outputting the rotating angle information with respect to a point in time prior to the transmission of the request signal by the predetermined period of time t0.

The other components are the same as those shown in FIG. 10.

Figure 13:
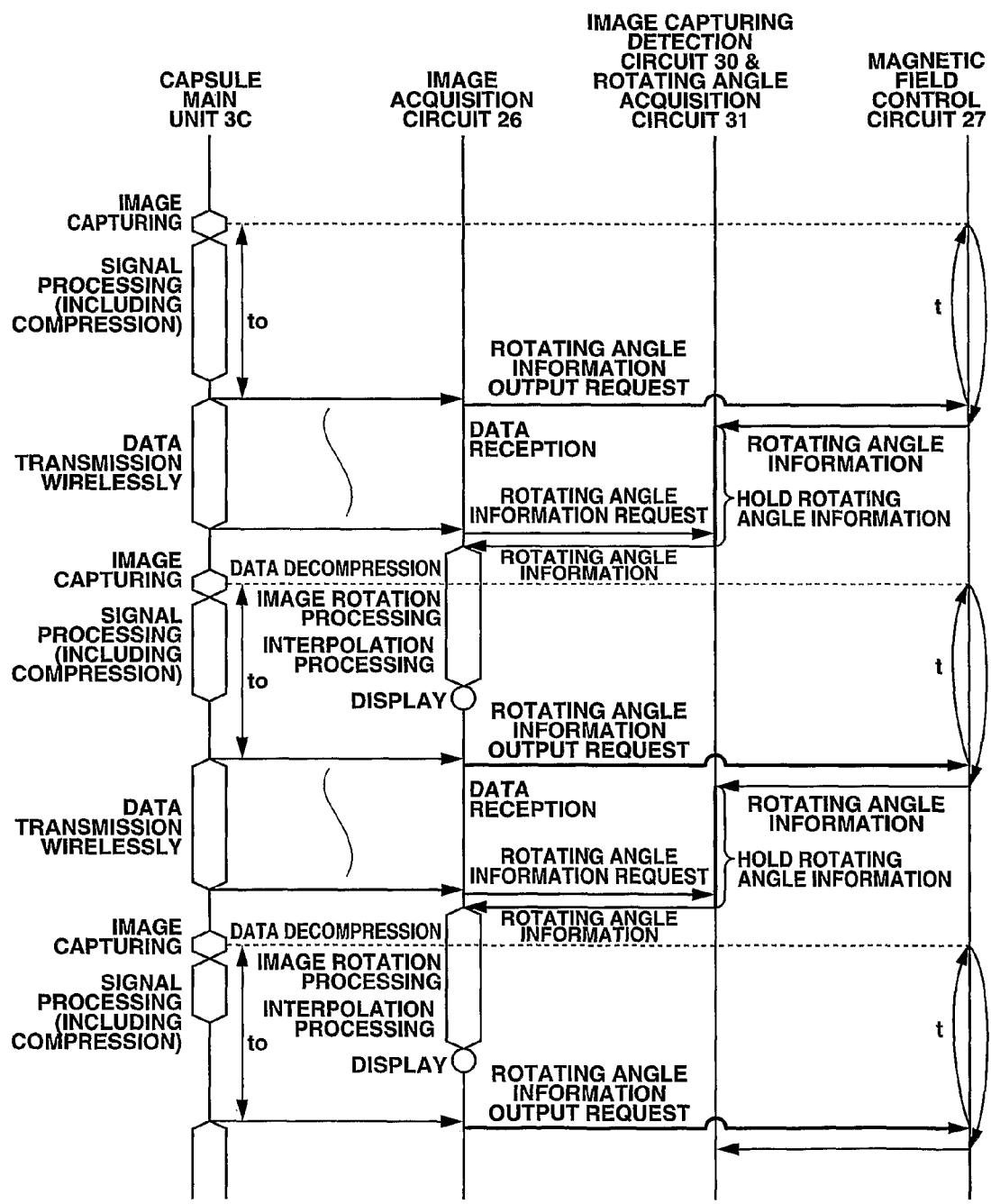
FIG. 13 is a timing chart showing the operation of the present embodiment.

FIG. 13 is a timing chart which shows the operation of the present embodiment. As shown in FIG. 13, the capsule 3C performs image capturing at approximately constant cycle. The image thus captured is subjected to A/D conversion by the signal processing circuit 20, following which the image data is compressed. Then, with the capsule control circuit 23, the image data is transmitted from the wireless communication circuit 22 after the predetermined period of time t0 from the point in time of image capturing.

The image acquisition circuit 26 included in the processing circuit 6C detects the image data through the wireless communication circuit 25. Upon detecting the first portion of the image data, the image acquisition circuit 26 transmits the rotating angle information output request signal to the magnetic field control circuit 27 with respect to the point in time prior to the reception of the signal by the predetermined period of time t0.

The magnetic field control circuit 27 reads out the rotating angle information with respect to a point in time prior to reception of the signal by the predetermined period of time t0, from the storage circuit 28, and outputs the rotating angle information thus read out. The rotating angle information is held by the rotating angle acquisition circuit 31. Upon completion of reception of the image data transmitted from the capsule 3C to the image acquisition circuit 26, the image acquisition circuit 26 performs image rotation processing and so forth with reference to the rotating angle information held by the rotating angle acquisition circuit 31. The rotation-corrected image is displayed on the display device 7.

On the other hand, after a predetermined period of time following completion of the transmission of the image data wirelessly, the capsule 3C starts the next image-capturing operation.

While the present embodiment, which performs the aforementioned operation, has a configuration in which only the image data is transmitted from the capsule 3C to the processing device 6C wirelessly without two-way wireless communication, the present embodiment has a function for detecting the point in time of image capturing performed by the capsule 3C with high precision and acquiring the corresponding rotating angle information, thereby enabling high-precision rotation correction.

Furthermore, capsule 3C can perform the next image-capturing operation in parallel with data decompression, image rotation processing, and so forth, performed by the processing device 6C, thereby enabling image capturing at a shorter cycle.

Furthermore, the present embodiment has a function for displaying an image corresponding to a predetermined rotating angle by rotation correction, thereby improving ease of use for propelling the capsule by adjusting the rotational magnetic field while observing the image.

Description has been made in the present embodiment regarding an arrangement in which the compressed image data is transmitted wirelessly after the predetermined period of time t0 from the time of image capturing. Also, in order to solve the problem of irregularities in the timing of image transmission due to compression, an arrangement may be made in which the compressed image data, to which time information has been appended, is transmitted immediately after image compression.

With such an arrangement, the capsule control circuit 23 controls so as to transmit the information (time information) regarding the period of time from the point in time of image capturing of the image pickup device 14 up to the start of transmission following image compression in a form appended to the first portion of the image.

Specifically, upon completion of the compression processing, the signal processing circuit 20 transmits an end signal to the capsule control circuit 23. The capsule control circuit 23 calculates the period of time from the point in time of image capturing up to reception of the end signal, and transmits the time information regarding the period thus calculated, to the wireless communication circuit 22. The wireless communication circuit 22 appends the time information to the image data, and starts output of the image data.

Then, the processing device 6C outside of the subject's body reads out the time information appended to the first portion of the image thus received, appends the time information to the rotating angle information output request signal, and transmits the rotating angle information output request signal including the time information to the magnetic field control circuit 27.

The magnetic field control circuit 27 outputs the rotating angle information with respect to a point in time prior to the time of input of the rotating angle information output request by the time t obtained from the time information. The rotating angle information thus output is held by the rotating angle acquisition circuit 31.

Then, with such an arrangement, the image acquisition circuit 26 performs image decompression processing for the compressed image, image-rotation processing, and so forth, based upon the rotating angle information.

Figure 14:
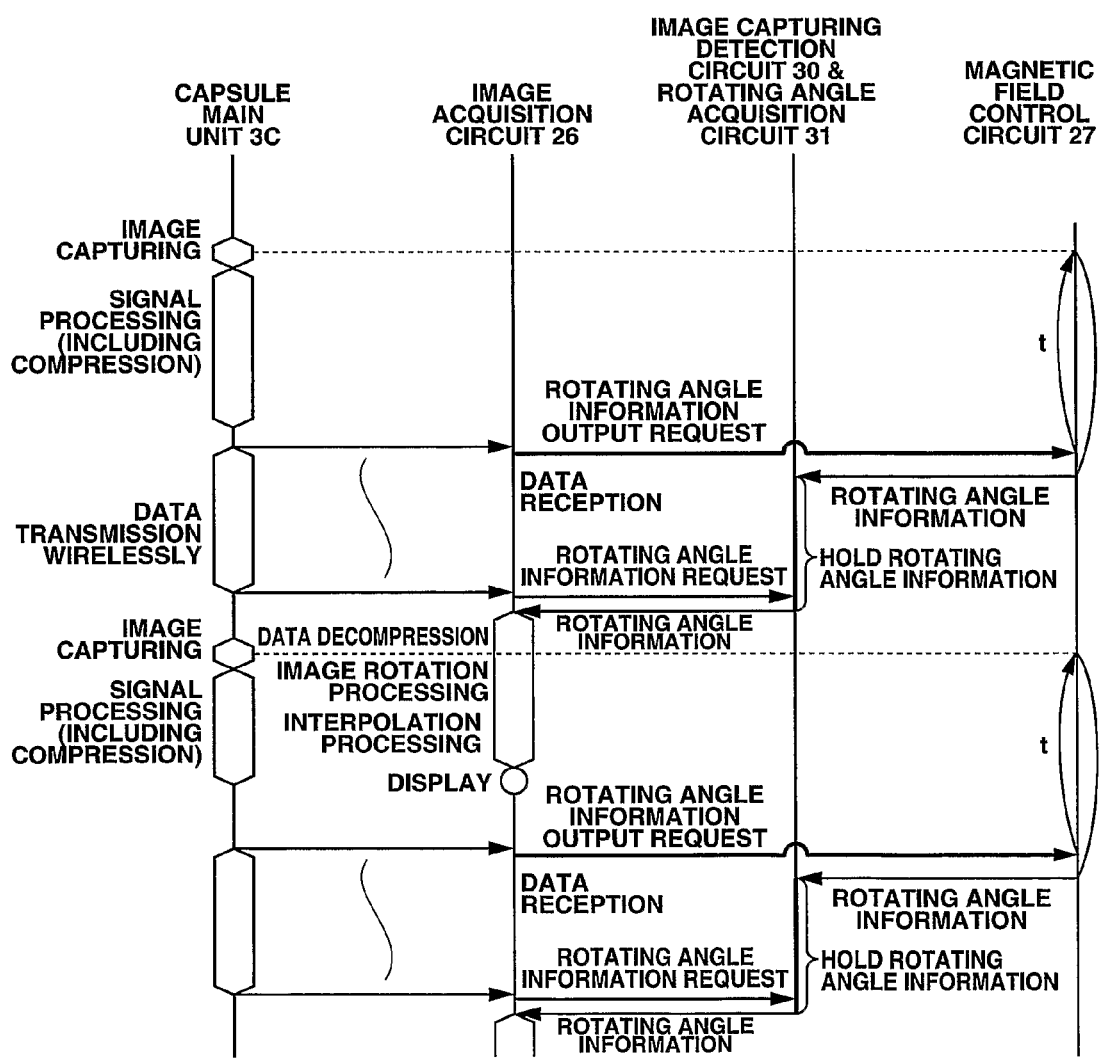
FIG. 14 is a timing chart showing the operation of a first modification.

FIG. 14 is a timing chart which shows the operation of the first modification.

With the capsule 3C, the capsule control circuit 23 controls the illumination device 15 so as to perform illumination with a constant cycle as well as controlling the image pickup device 14 so as to perform image capturing, for example. At the point in time of image capturing, the capsule control circuit 23 starts the timer 23a so as to start measurement of time.

The captured image signal captured by the image pickup device 14 is subjected to A/D conversion by the signal processing circuit 20. Furthermore, the image data is compressed, and the image data thus compressed is stored in the memory 21.

At the time of transmission from the wireless communication circuit 22 following completion of image-data compression, the signal processing circuit 20 notifies the capsule control circuit 23 of the end of data compression. The capsule control circuit 23 obtains the period of time t from the time of the start of image capturing using the timer 23a, appends the information regarding the period of time t to the first portion of the image data, and transmits the image data.

The image acquisition circuit 26 reads out the information regarding the period of time t appended to the first portion of the image data at the time of reception of the image data, and instructs the magnetic field control circuit 27 to output the rotating angle information with respect to a point in time prior to the current time by the period of time t.

Upon completion of acquisition of the image data thus transmitted, the image acquisition circuit 26 performs decompression of the compressed image data, image-rotation processing based upon the rotating angle information, and so forth. The rotation-corrected image is displayed on the display device 7.

On the other hand, with the capsule 3C, the capsule control circuit 23 performs the next image capturing operation after a predetermined period of time from the previous image capturing operation.

The present modification, which performs such operation, needs to transmit the time information with respect to the point in time of image capturing in the form of appended information. However, the present modification has the advantage of enabling transmission of the image data wirelessly immediately after completion of compression of the image data, regardless of irregularities in time up to completion of the compression processing principally due to compression of the image data.

That is to say, the present modification enables detection of the time of image capturing in a sure manner even in a case of irregularities in time required for image compression due to the nature of the captured image. This allows high-precision display of the images without rotation with a simple configuration.

Next, description will be made regarding a second modification. With the embodiment 3, following transmission of the image data wirelessly, the capsule 3C starts the next image-capturing operation while the processing device 6C performs decompression processing for the compressed image data and so forth. Also, an arrangement may be made in which the capsule 3C performs the next image-capturing operation after the processing device 6C has performed image-data decompression processing and so forth.

Figure 15:
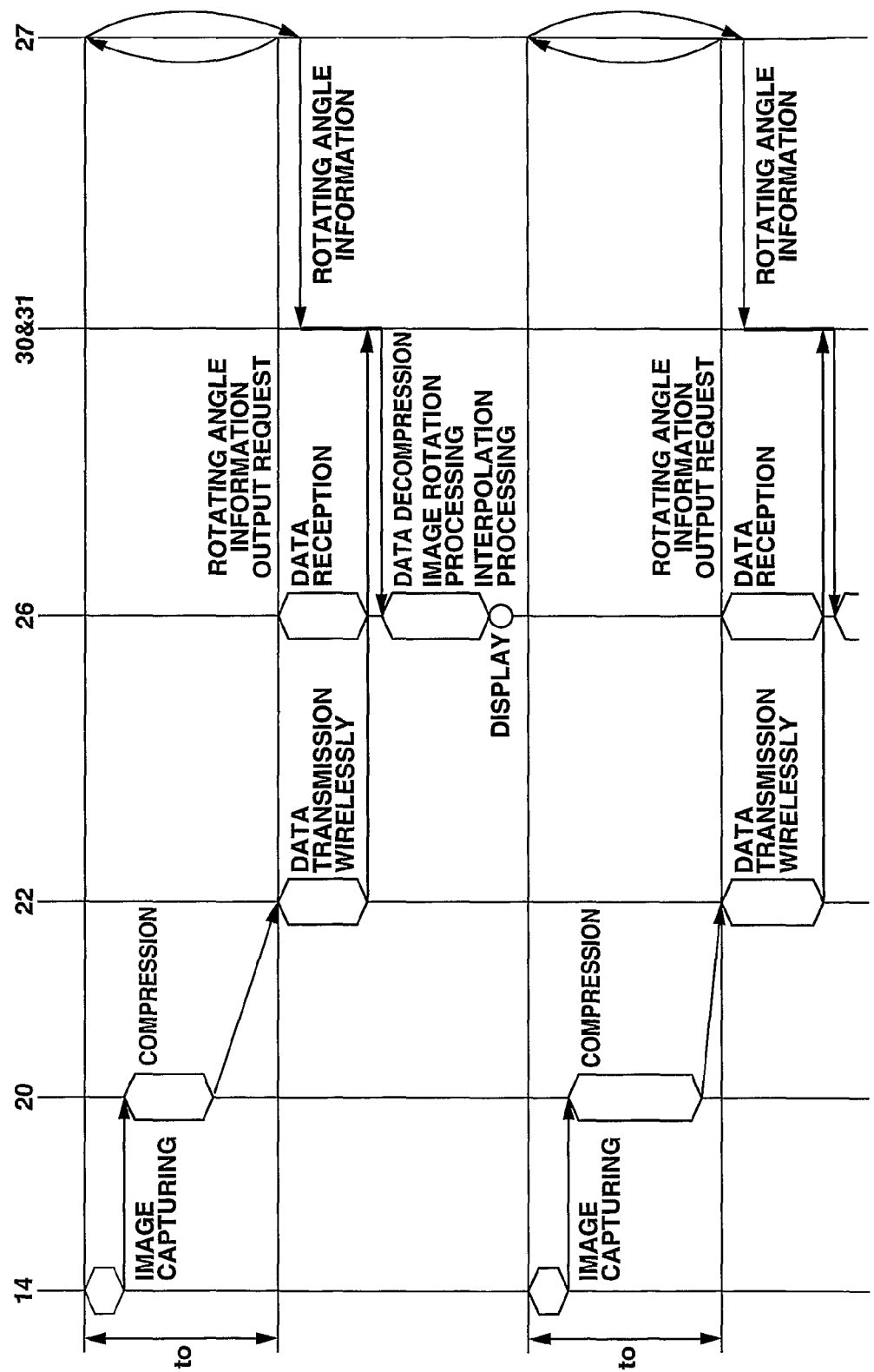
FIG. 15 is a timing chart showing the operation of a second modification.

FIG. 15 is a timing chart which shows the operation of such an arrangement. In FIG. 15, the operation of the capsule 3C shown in FIG. 13 is classified into: the operation of the image pickup device 14 for performing image capturing; the operation of the signal processing circuit 20 for performing A/D conversion and image-data compression processing; and the operation of the wireless communication circuit 22 for transmitting the compressed image data stored in the memory 21 wirelessly.

With the operation shown in FIG. 15, the capsule 3C starts wireless communication of the image data through the wireless communication circuit 22 after the predetermined period of time from the time of image capturing, as shown in FIG. 13. Note that in FIG. 15, the point in time of image capturing matches the point in time of the start of image capturing for simplicity of description.

The image acquisition circuit 26 receives the image data transmitted wirelessly. Upon detecting the first portion of the image data, the image acquisition circuit 26 transmits a rotating angle information output request signal to the magnetic field control circuit 27 so as to instruct the magnetic field control circuit 27 to output the rotating angle information with respect to a point in time prior to reception of the signal by the predetermined period of time t0. The rotating angle acquisition circuit 31 holds the rotating angle information thus output.

Furthermore, the image acquisition circuit 26 performs decompression of the compressed image data, image-rotation processing based upon the rotating angle information, and so forth. Subsequently, the image data is output to the display device 7, whereby the display device 7 displays the rotation-corrected image.

After a predetermined period of time from display of the image on the display device 7, the capsule 3C starts the next image-capturing operation.

Next, description will be made regarding a third modification. The present modification modified from the second modification has a function for performing image capturing and image-rotation correction at shorter intervals and sequentially displaying the rotation-corrected images than that of the embodiment 3.

With the present modification, the image acquisition circuit 26 is formed of two separate units of: an image data storage unit 26a for acquiring image data from the wireless communication circuit 25 and storing the image data in memory or the like; and an image processing unit 26b for performing decompression processing, image rotation processing, and interpolation processing for the image data stored in the image data storage unit 26a.

With such a configuration, the image data storage unit 26a receives (stores) the next image data in parallel with decompression processing performed by the image processing unit 26b, thereby improving the frame rate of image capturing. Note that FIG. 16 shows the image data storage unit 26a and the image data processing unit 26b denoted by these reference numerals.

Figure 16:
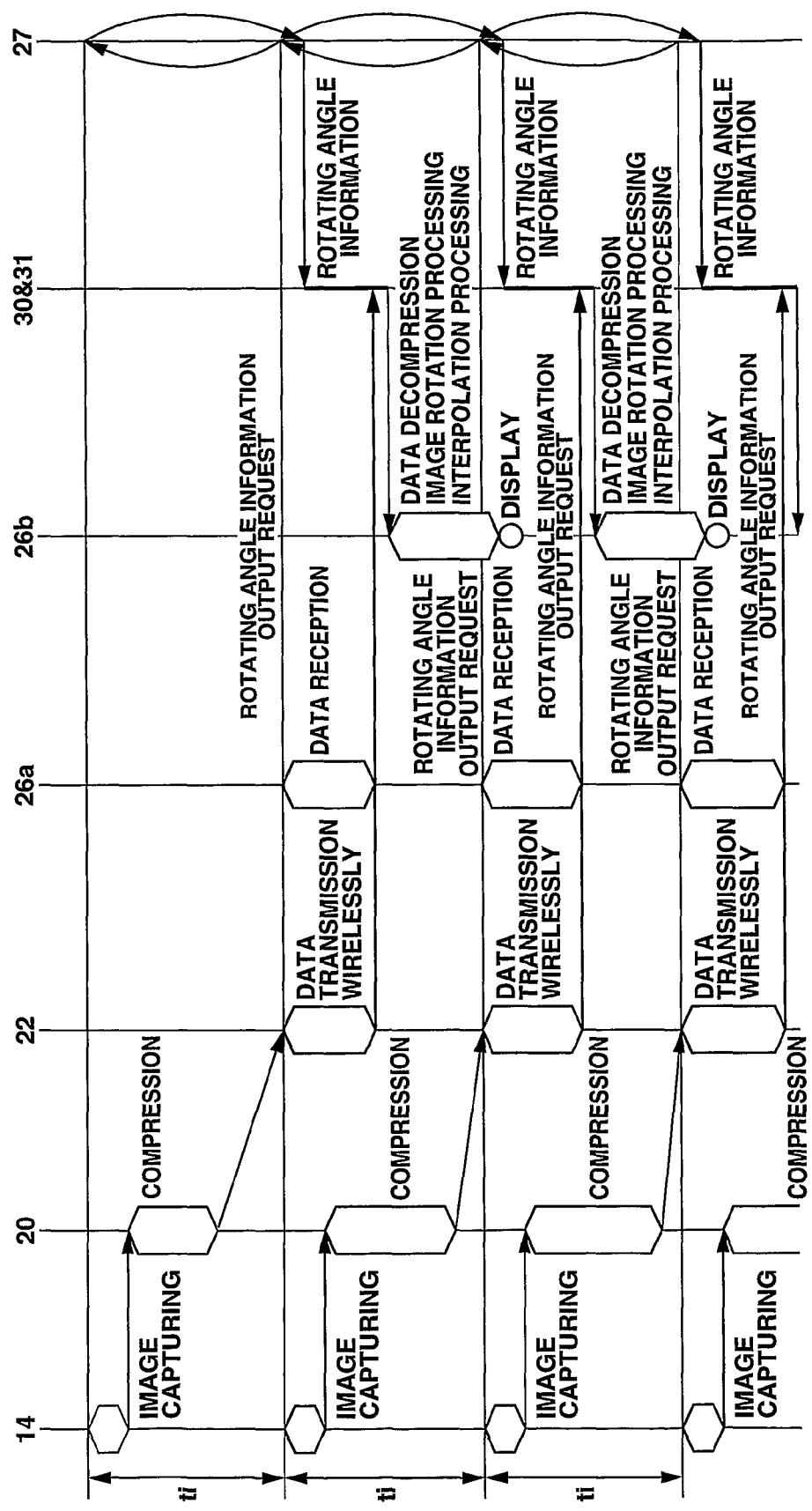
FIG. 16 is a timing chart showing the operation of a third modification.

FIG. 16 is a timing chart which shows the operation of the third modification. In FIG. 16, the operation of the image acquisition circuit 26 shown in FIG. 15 is classified into: the operation of the image data storage unit 26a which comprises memory and so forth for sequentially storing image data from the wireless communication circuit 25; and the operation of the image processing unit 26b for performing image decompression processing, image rotation processing, and interpolation processing for the image data stored in the image data storage unit 26a.

With the operation shown in FIG. 16, in the capsule 3C, upon completion of image capturing at the image pickup device 14, the signal processing circuit 20 performs A/D conversion for the image, and image-data compression processing, whereby the compression processing ends.

In this case, after a predetermined period of time t1 from the time of image capturing, the wireless communication circuit 22 starts the operation for transmitting the compressed image data wirelessly, while the image pickup device 14 starts the next image-capturing operation (under the control of the capsule control circuit 23).

Upon transmission of the image data wirelessly, the image data storage unit 26a of the processing device 6C receives the image data. Upon detecting the first portion of the image data, the image data storage unit 26a transmits a rotating angle information output request signal to the magnetic field control circuit 27 for instructing the magnetic field control circuit 27 to output the rotating angle information with respect to a point in time prior to reception of the signal by the predetermined period of time t0. The rotating angle acquisition circuit 31 holds the rotating angle information.

Upon receiving (storing) the entire image data, the image data storage unit 26a transmits a signal for requesting the rotating angle acquisition circuit 31 to transmit the rotating angle information held therein to the image processing unit 26b. Subsequently, the image processing unit 26b performs decompression of the image data stored in the image data storage unit 26a, image rotation processing based upon the rotating angle information, and so forth. The rotation-corrected image is output to the display device 7, whereby the rotation-corrected image is displayed on the display device 7.

With the aforementioned capsule 3C, following the image-capturing operation, the signal processing circuit 20 starts A/D conversion for the image and image-data compression processing. Furthermore, after the predetermined period of time t1 from the time of image capturing, the image pickup device 14 performs the next image-capturing operation (under the control of the capsule control circuit 23) while the wireless communication circuit 22 starts transmission of the compressed image data wirelessly.

The present modification, which performs such operation, enables image capturing and rotation-correction for the image thus captured at shorter intervals than with the embodiment 3. This allows display of images equivalent to those captured by the image pickup device without rotation, thereby facilitating observation.

Note that the aforementioned system is more suitably applied to the case in which the sum of the image-capturing time and the processing time in the capsule 3C is greater than the time for transmission of the data to the image acquisition circuit 26.

Embodiment 4

Next, description will be made regarding an embodiment 4 according to the present invention with reference to FIG. 17.

Figure 17:
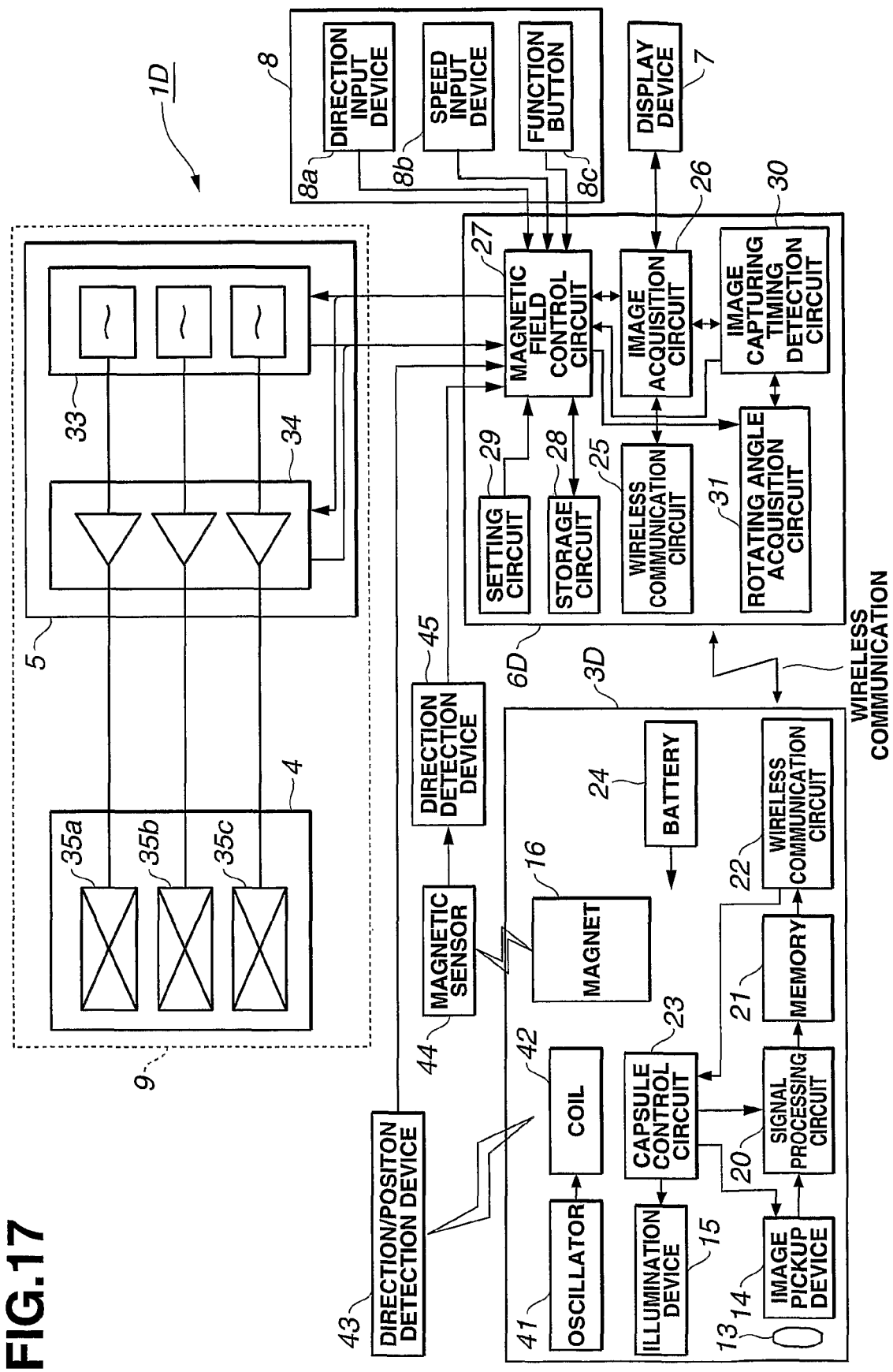
FIG. 17 is a block diagram showing an internal configuration of the components of a capsule medical system according to an embodiment 4 of the present invention.

FIG. 17 shows a configuration of a capsule medical system 1D according to the embodiment 4 of the present invention.

The capsule medical system 1D according to the present embodiment includes a capsule 3D having generally the same configuration as that of the capsule 3 included in the capsule medical system 1 according to the embodiment 1 shown in FIG. 2, except for further including an oscillator 41 and a coil 42 for generating an AC magnetic field therearound using the output signal from the oscillator 41.

On the other hand, the components provided outside of the capsule 3D include: a direction/position detection device 43 for detecting both the direction and the position of the capsule 3D in the longitudinal direction thereof using the A/C magnetic field generated by the coil 42; a magnetic-pole sensor 44 for detecting the direction of the magnet 16 included within the capsule 3D; and a (magnet) direction detection device 45 for detecting the direction of the magnet based upon the output of the magnetic-pole sensor 44.

The capsule 3D has generally the same configuration as that of the capsule 3 shown in FIG. 3A, except for further including the coil 42 therewithin around the rear end of the exterior container 11 with a predetermined direction. Specifically, the capsule 3D stores the coil 42 wound in the form of a solenoid therewithin, with the direction of the solenoid matching the longitudinal direction of the capsule 3D, for example.

The aforementioned direction/position detection device 43 includes multiple sensor coils for detecting the AC magnetic filed, for example, thereby detecting the direction and the position of the coil 42 based upon the signals detected by the sensor coils. On the other hand, the magnetic-pole sensor 44 comprises multiple magnetic-pole sensors, and detects the magnetic direction of the magnet 16 based upon the output signals of the multiple magnetic-pole sensors. Furthermore, such a configuration allows detection of the direction of the capsule 3D in the longitudinal direction, such as the front direction and so forth, based upon the positions of the coil 42 and the magnet 16 included within the capsule 3D.

Also, an arrangement may be made employing an antenna instead of the coil 42. With such an arrangement, the air waves transmitted from the antenna is received by the direction/position detection device 43 in order to detect the direction and the position of the capsule 3D in the longitudinal direction thereof.

The information detected by the direction/position detection device 43 and the information detected by the direction detection device 45 are input to the magnetic field control circuit 27 of the processing device 6D.

While the processing device 6D has the same configuration as that of the processing device 6 shown in FIG. 2, part of the operation of the magnetic field control circuit 27 is different thereamong.

Upon the user operating the operation input device 8, the magnetic field control circuit 27 generates a rotational magnetic field or controls the direction and so forth of the rotational magnetic field thus generated, within a suitable range, based upon the information detected by the information stored in the storage circuit 28 and the information detected by the direction/position detection device 43 and the direction detection device 45.

Specifically, let us say that the user operates the operation input device 8 so as to change the direction of the rotational magnetic field, for example. Based on the information detected by the direction/position detection device 43 and the direction detection device 45, the magnetic field control circuit 27 determines whether or not change in the rotating magnetic field direction changed from the current direction of the magnet 16 of the capsule 3D is within a suitable range giving consideration to the torque and so forth applied to the magnet 16.

In a case that the change in the rotating magnetic field direction is within a suitable range, the direction of the rotational magnetic field is changed according to the operation input. On the other hand, in a case that the change in the rotating magnetic field direction deviates from the suitable range, the operation input is suppressed with respect to the time (i.e., the rate of change is reduced with respect to the time) to be within the suitable range.

This controls the direction of the rotational magnetic field, the change in the frequency thereof, and so forth, requested by the operation input from the operation input device 8, within a suitable range giving consideration to the response of the capsule 3D, thereby enabling smooth control of the propelling operation by rotation of the capsule 3D.

The present embodiment has the same advantages as with the embodiment 1, in addition to the aforementioned advantage.

Note that while description has been made regarding an arrangement in which the present embodiment is applied to the embodiment 1 shown in FIG. 2, it is needless to say that the present embodiment may be applied to the modification of the embodiment 1, the embodiment 2, and the embodiment 3. Such an arrangement also has the advantage of smooth propelling actions of the capsule and so forth by suppressing the operation input of the operation input device 8 to be within a suitable range as described above.

Embodiment 5

Figure 18:
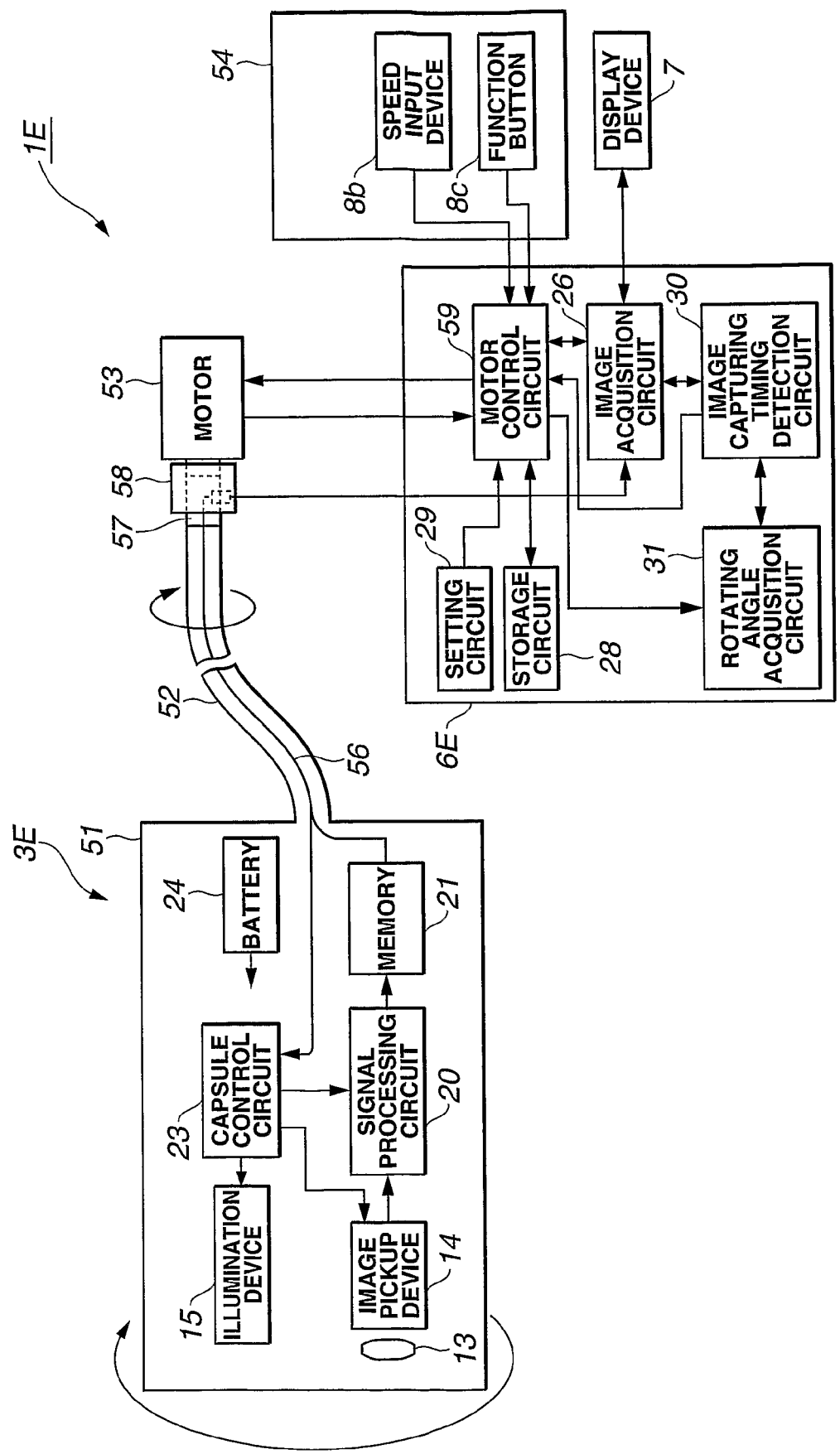
FIG. 18 is a block diagram showing an internal configuration of the components of a capsule medical system according to an embodiment 5 of the present invention.
Figure 19:
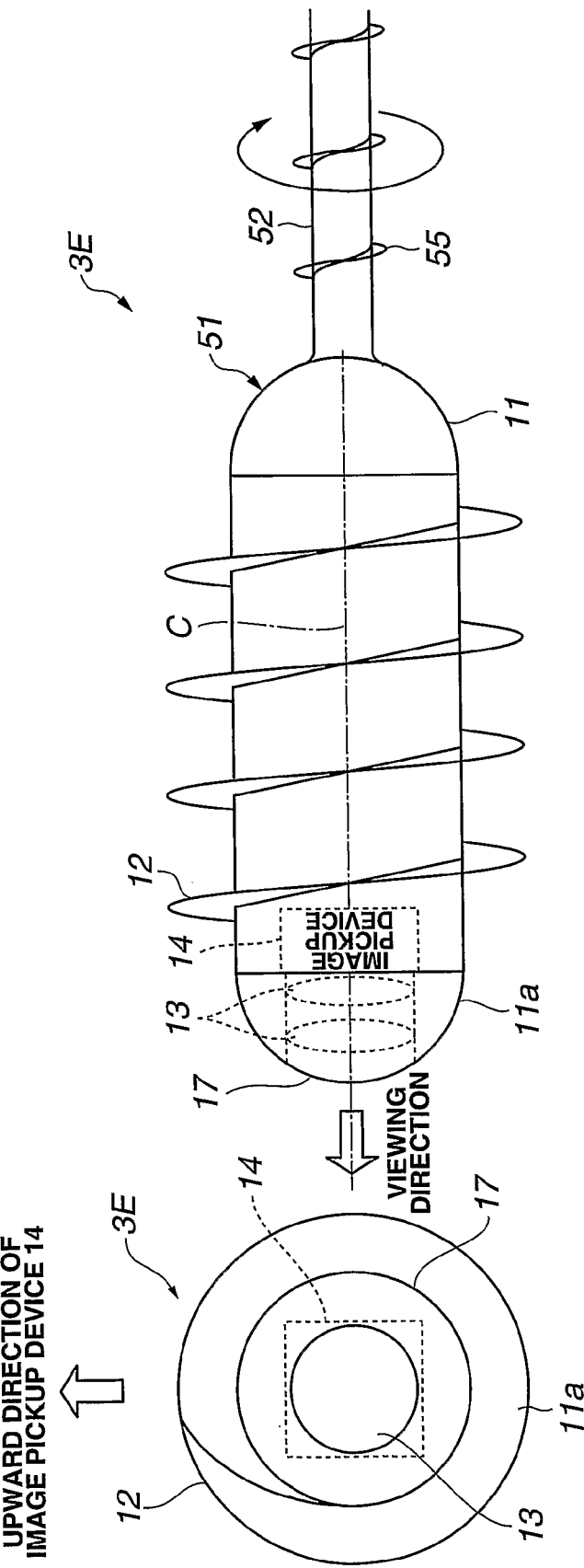
FIG. 19A is a side view of the medical device.
FIG. 19B is a front view of the medical device.

Next, description will be made regarding an embodiment 5 according to the present invention with reference to FIGS. 18 through 19B. FIG. 18 shows a configuration of a medical system 1E according to the embodiment 5 of the present invention. While description has been made in the above-described embodiments regarding an arrangement which allows the rotational speed of the capsule 3 and so forth to be changed by controlling the rotational magnetic field, with the present embodiment, the capsule is driven so as to be rotated using rotation driving means without involving the rotational magnetic field, as described below.

As shown in FIG. 18, a medical system 1E includes: a medical device 3E having a structure in which a capsule-shaped unit 51 is provided to the distal end of a flexible tube 52; a motor 53 for driving so as to rotate the medical device 3E; an operation input device 54 which allows change of the rotational speed of the motor 53 and so forth; a processing device 6E for controlling the rotation of the motor 53 according to the operation input from the operation input device 54 and performing signal processing for the signal captured by the image pickup device 14 included within the medical device 3E; and the display device 7 for displaying the image captured by the image pickup device 14.

As shown in FIGS. 19A and 19B, the medical device 3E has generally the same configuration as that of the capsule 3 shown in FIGS. 3A and 3B, except for a structure in which the distal end of the flexible tube 52 is connected to the rear end of the capsule-shaped unit 51 having the capsule-shaped exterior container 11. In such a structure, the distal end of the flexible tube 52 is provided with the axis thereof matching the center axis C of the capsule-shaped unit 51. Thus, the front view thereof shown in FIG. 19B shows generally the same structure as that shown in FIG. 3B. Note that the present embodiment does not use the rotational magnetic field, and employs the motor 53 for rotating the medical device 3E. Accordingly, the magnet 16 is not included within the capsule-shaped unit 51.

Furthermore, with the present embodiment, a helical protrusion 55 is provided to the outer face of the flexible tube 52 at the same pitch of that of the helical protrusion 12 provided to the outer face of the capsule-shaped unit 51. The combination of the helical protrusions 12 and 55 serves as a propelling-force generating structure having a function for generating greater propelling force than with an arrangement including only the helical protrusion 12.

The capsule-shaped unit 51 stores the illumination device 15, the image pickup device 14, and so forth, therewithin, as shown in FIG. 18. Note that the capsule-shaped unit 51 stores the same components as those stored in the capsule 3 shown in FIG. 2, except for the magnet 16 and the wireless communication circuit 22. While the capsule-shaped unit 51 stores the battery 24, an arrangement may be made in which electric power is supplied from the processing device 6E outside of the capsule-shaped unit 51.

Furthermore, the memory 21 and the capsule control circuit 23 stored within the capsule-shaped unit 51 are connected to one end of a signal line 56 inserted into the flexible tube 52. The other end is connected to the contact provided to the outer face of a connector 57 provided to the rear end (base) of the flexible tube 52.

The contact of the connector 57 is connected to the rotary shaft of the motor 53. Note that a slip ring 58 is provided to the outer portion of the rotary shaft with the connector 57 serving as a rotor. A signal line connected to a stator-side contact provided to the inner face of the slip ring 58 is connected to the image acquisition circuit 26 of the processing device 6E.

The image acquisition circuit 26 transmits an image capturing request signal to the capsule control circuit 23 as well as receiving the image data which has been captured by the image pickup device 14 and has been subjected to image processing by the signal processing circuit 20, in the same way as with the embodiment 1.

While description has been made in the embodiment 1 regarding an arrangement in which the signal is exchanged wirelessly through the wireless communication circuit 22 or the like, with the present embodiment, the signal is exchanged through the signal line 56.

Furthermore, the processing device 6E includes a motor control circuit 59 for controlling the rotational speed of the motor 53, instead of the magnetic field control circuit 27 in the processing device 6 in FIG. 2. The motor control circuit 59 controls the motor 53, which allows change in the rotational speed thereof according to the operation input via the operation input device 54.

Note that the operation input device 54 includes the speed input device 8b and the function button 8c in the same way as with the embodiment 1, but does not include the direction input device 8a.

The present embodiment has the same configuration as with the embodiment 1, except for the aforementioned configurations.

Description has been made in the embodiment 1 regarding an arrangement in which upon detecting the point in time of image capturing, the processing device 6 acquires the rotating angle information regarding the rotational magnetic field from the magnetic field control circuit 27, and performs image rotation processing for the image data acquired by the capsule 3 so as to rotate the image, thereby correcting the image to correspond to a predetermined rotating angle. With the present embodiment, upon detecting the point in time of image capturing, the processing device 6E acquires the rotating angle information regarding the motor 53 from the motor control circuit 59, and performs image rotation processing for the image data acquired by the capsule-shaped unit 51 so as to rotate the image, thereby correcting the image to correspond to a predetermined rotating angle.

The operation of the rotation correction according to the present embodiment is generally the same as the operation according to the embodiment 1 shown in the timing chart in FIG. 7, with the magnetic field circuit 27 replaced by the motor control circuit 59.

The present embodiment also has a function for displaying the images corresponding to a predetermined rotating angle even in a case of driving and rotating the capsule-shaped unit 51 in the same way as with the embodiment 1.

Figure 20:
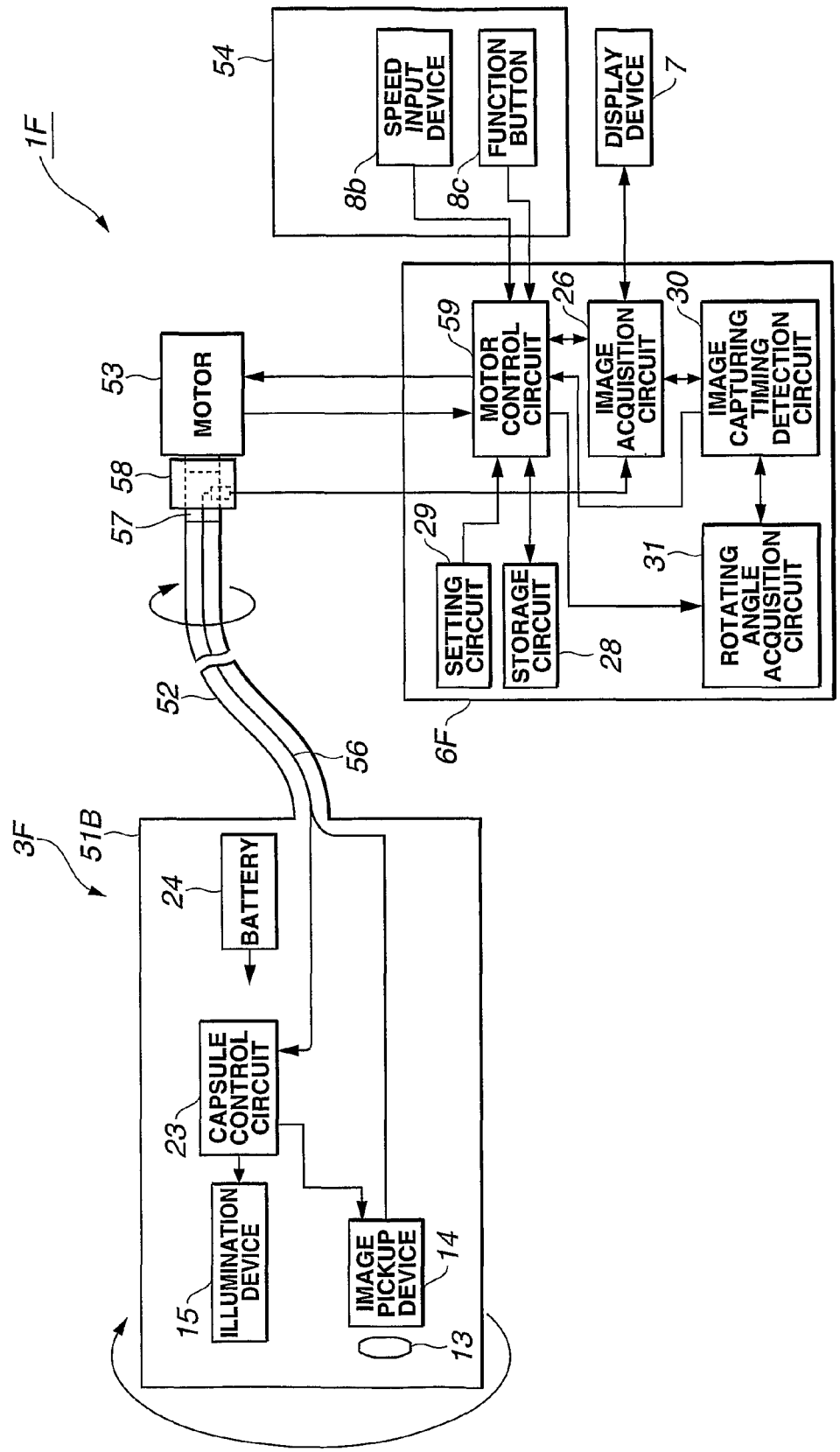
FIG. 20 is a block diagram showing an internal configuration of the components of a capsule medical system according to a modification.

FIG. 20 shows the configuration of a medical system 1F according to a modification. The medical system 1F has the same configuration as that of the medical system 1E shown in FIG. 18, except for employing the capsule-shaped unit 51B which does not include the signal processing circuit 20 and the memory 21, which are included in the capsule-shaped unit 51.

That is to say, with the present modification, the image acquisition circuit 26 acquires the image captured by the image pickup device 14 through the signal line 56. The other configuration is the same as that shown in FIG. 18.

The present modification provides generally the same advantages as those of the embodiment 5 at lower costs than with the embodiment 5.

Description has been made in the present modification regarding an arrangement in which the image acquisition circuit 26 transmits the image capturing request signal to the capsule control circuit 23. Also, an arrangement may be made in which the capsule-shaped unit 51 performs image capturing at predetermined timing intervals or the like, and at that time, the capsule control circuit 23 transmits a signal to the image acquisition circuit 26 or the image capturing timing detection circuit 30 for detection of the point in time of image capturing.

Embodiment 6

Next, description will be made regarding an embodiment 6 according to the present invention with reference to FIGS. 21 through 23. The difference between a capsule medical system 1G according to the embodiment 6 shown in FIG. 21 and the capsule 3 according to the embodiment 1 is that a capsule 3G includes multiple image pickup devices. Note that the same components as those of the capsule medical system 1 according to the embodiment 1 are denoted by the same reference numerals, and description thereof will be omitted.

Figure 21:
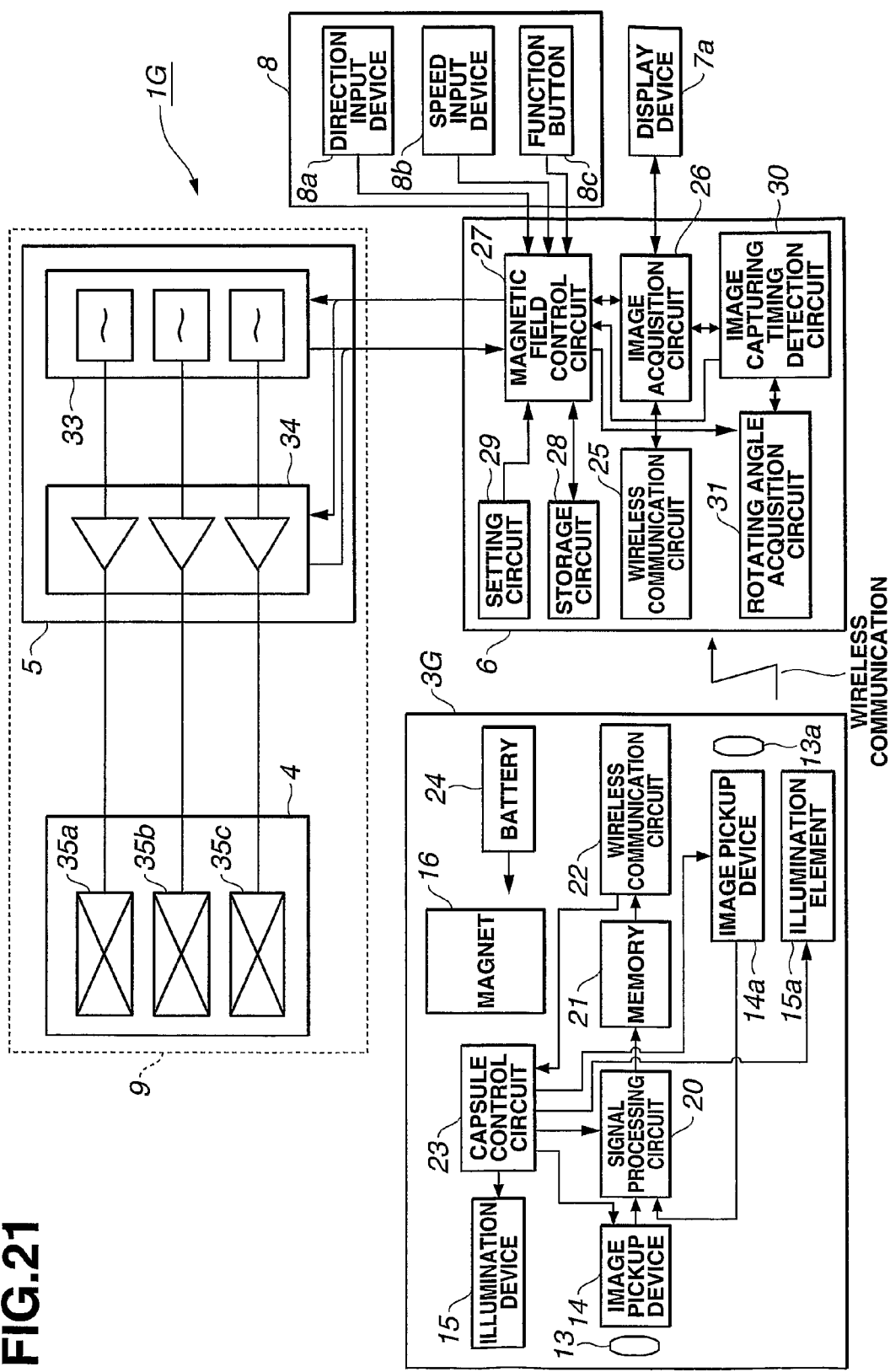
FIG. 21 is an overall configuration diagram showing a capsule medical system according to an embodiment 6 of the present invention.
Figures 22A, 22B:
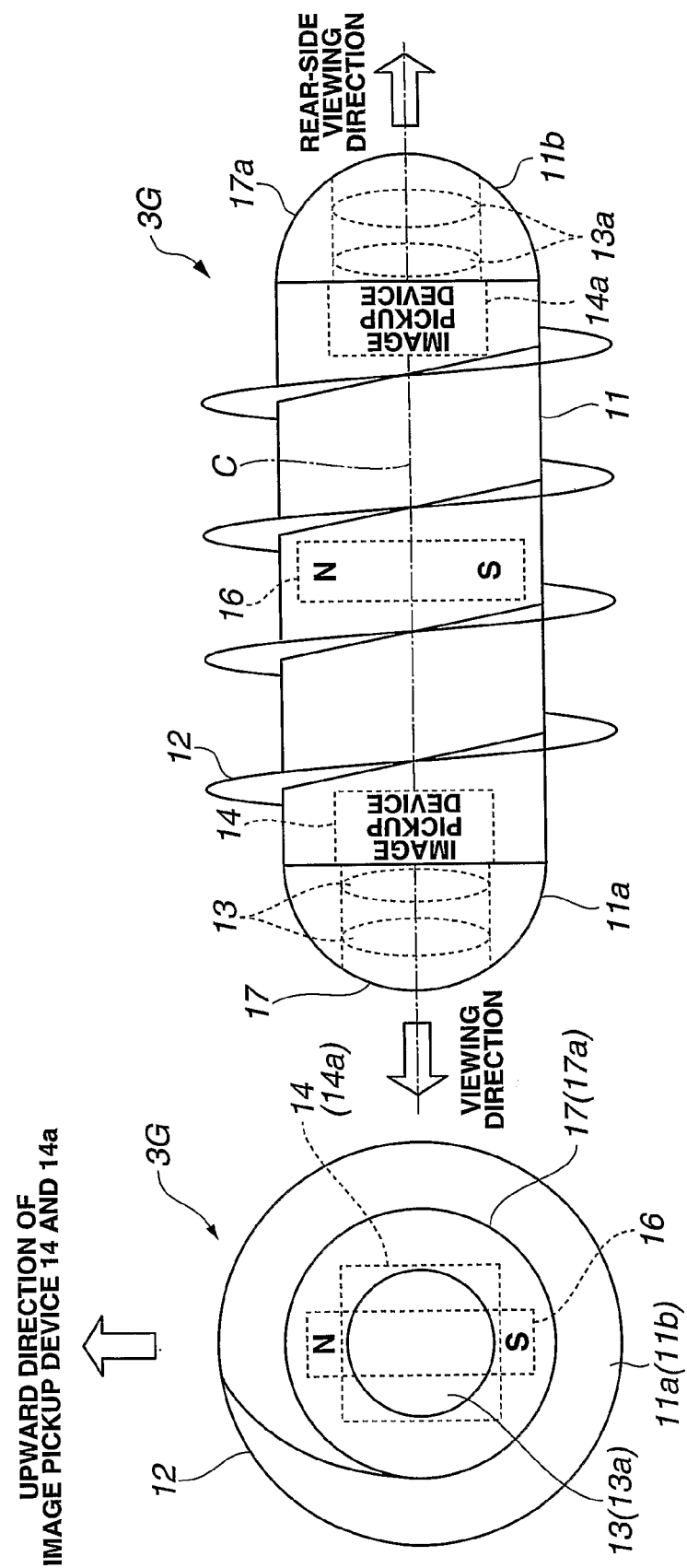
FIG. 22A is a side view of the capsule.
FIG. 22B is a front view of the capsule.

FIG. 21 shows an internal configuration of the components of the capsule medical system 1G according to the present embodiment. FIG. 22A shows a side view of the capsule 3G. FIG. 22B shows a front view of the capsule 3G. FIG. 23 shows a display device 7a displaying the image captured by the capsule 3G according to the present embodiment.

As shown in FIG. 21, the capsule medical system 1G of the present embodiment includes an objective optical system 13a and an image pickup device 14a disposed at an image-forming position of the objective optical system 13a, which form image capturing means, and an illumination device 15a for performing illumination, in addition to the components of the capsule 3 according to the embodiment 1.

Furthermore, the image pickup device 14a is connected to the signal processing circuit 20. The captured image signal output from the image pickup device 14a is subjected to signal processing by the signal processing circuit 20 in the same way as the captured image signal output from the image pickup device 14.

The image pickup devices 14 and 14a are disposed at opposite ends of the exterior container 11 of the capsule 3G in the longitudinal direction as described below, thereby capturing images in directions opposite to each other.

As shown in FIG. 22A, the objective optical system 13a is disposed so as to face the opposite direction of the objective optical system 13 with the optical axis thereof matching the center axis C of the cylindrical capsule 3G. The aforementioned objective optical system 13a is disposed inside of a transparent front cover 11b formed in the shape of a hemisphere forming a part of the exterior container 11, for example. Furthermore, an observation window 17a is provided to the center of the front cover 11b as shown in FIG. 22B. Note that an illumination device 15a is disposed around the objective optical system 13a, which is not shown in FIGS. 22A and 22B.

Figure 23:
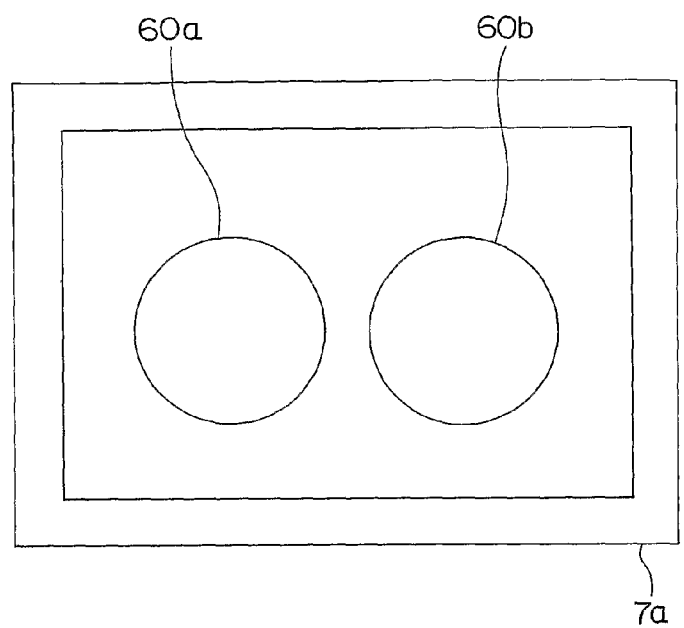
FIG. 23 is a diagram showing an example in which two images captured by the capsule are displayed on a display device.

Furthermore, the display device 7a has a configuration for displaying the images captured by both the image pickup devices 14 and 14a on display windows 60 and 60a, as shown in FIG. 23. The other components are the same as those of the embodiment 1.

Next, description will be made regarding the operation of the present embodiment having the aforementioned configuration.

A general outline description will be made of the present embodiment regarding only the operation from the image capturing by the multiple image pickup devices 14 and 14a of the capsule 3G up to the start of rotation processing for the images thus captured, and display of the images subjected to rotation processing. The other operation is the same as that of the embodiment 1, and detailed description thereof will be omitted.

In capsule 3G, upon the capsule control circuit 23 receiving an image request signal from the image acquisition circuit 26 through the wireless communication circuit 22, the capsule control circuit 23 instructs the illumination device 15a to perform illumination so as to illuminate the field of view of the image pickup device 14a as well as instructing the image pickup device 14a to perform image capturing. Subsequently, the capsule control circuit 23 instructs the illumination device 15 to perform illumination as well as instructing the image pickup device 14 to perform image capturing.

Thus, the capsule control circuit 23 operates the image pickup devices 14 and 14a alternately, thereby capturing images by the image pickup devices 14 and 14a, disposed at the opposite ends of the capsule 3, alternately.

The captured image signals output from the image pickup devices 14a and 14 are subjected to compression processing by the signal processing circuit 20. Furthermore, the compressed image data is subjected to image processing for appending a signal (image pickup device identifying signal) for identifying whether the signal has been output from the image pickup devices 14 or 14a, following which the image data is stored in the memory 21.

The image data stored in the memory 21 is modulated by the wireless communication circuit 22 in the same way as with the embodiment 1, and the modulated image data is transmitted to the processing device 6 by wireless communication. The image acquisition circuit 26 included within the processing device 6 identifies whether the image has been captured by the image pickup device 14 or 14a with reference to the image pickup device identifying signal appended by the signal processing circuit 20.

In a case that the received image is an image captured by the image pickup device 14, the same image rotation processing is performed as with the embodiment 1, and the image thus processed is displayed on the display window 60 of the display device 7a.

On the other hand, in a case that the received image is an image captured by the image pickup device 14a, image rotation processing is performed using a rotating angle obtained by multiplying the aforementioned rotating angle by −1 (i.e., the same image rotation processing as with the image captured by the image pickup device 14, except for the reverse rotating direction), and the image thus processed is displayed on the display window 60a of the display device 7a. The reason why such image rotation processing is performed is as follows. That is to say, the viewing directions of the image pickup devices 14a and 14 are different from each other (i.e., the viewing directions are opposite from each other), and accordingly, the rotating directions thereof are different from each other.

With the present embodiment, the two image pickup devices 14 and 14a have the opposite viewing directions different from each other. Accordingly, the image data output from the image pickup device 14a is subjected to the image rotation processing using rotating angle obtained by multiplying the aforementioned rotating angle by −1.

With the present embodiment, the image captured by each of the multiple image pickup devices (image sensors) included in the capsule 3G is subjected to rotation processing using a corresponding rotating angle, thereby displaying the images from all the image pickup devices without the concern for rotation thereof. Furthermore, let us say that the operator operates the capsule 3G so as to change the propelling direction of the capsule 3G to the reverse direction. In this case, the present embodiment provides images in the rear-side viewing direction, thereby improving ease of use.

While description has been made with reference to FIG. 22A with the direction of the image pickup device 14 as the viewing direction, and with the direction of the image pickup device 14a as the rear-side viewing direction for simplicity of description, description may be made with the direction of the image pickup device 14a as the viewing direction, and with the direction of the image pickup device 14 as the rear-side viewing direction.

Description has been made regarding an arrangement in which the display device 7a displays the images captured by the image pickup devices 14 and 14a on the display windows 60 and 60a in parallel, respectively. Also, an arrangement may be made in which the display device 7a displays the image captured by the propelling-direction image pickup device alone. With such an arrangement, upon the user operating so as to reverse the capsule 3G, the display device 7a switches the image displayed thereon (i.e., switches from the image captured by the image pickup device 14 to the image captured by the image pickup device 14a). Also, an arrangement may be made in which the display device 7a displays the images captured by the image pickup devices 14 and 14a in different sizes.

Description has been made in the present embodiment regarding an arrangement in which the image pickup devices 14 and 14a operate alternately. Also, an arrangement may be made in which the signal processing circuit 20 has twofold processing performance so as to allow the image pickup devices 14 and 14a to operate in parallel.

Also, description will be made in an embodiment 7 and the following embodiments regarding other arrangements of the medical device for performing image capturing while rotating within the body cavity.

Embodiment 7

Next, description will be made regarding an embodiment 7 according to the present invention with reference to FIGS. 24 through 43. It is an object of the embodiment 7 and the following embodiments to provide a capsule medical device and a capsule medical system which have a function for generating the propelling force of the medical device inserted within the body cavity by actions of the helical rotation propelling structure with high efficiency.

Figure 24:
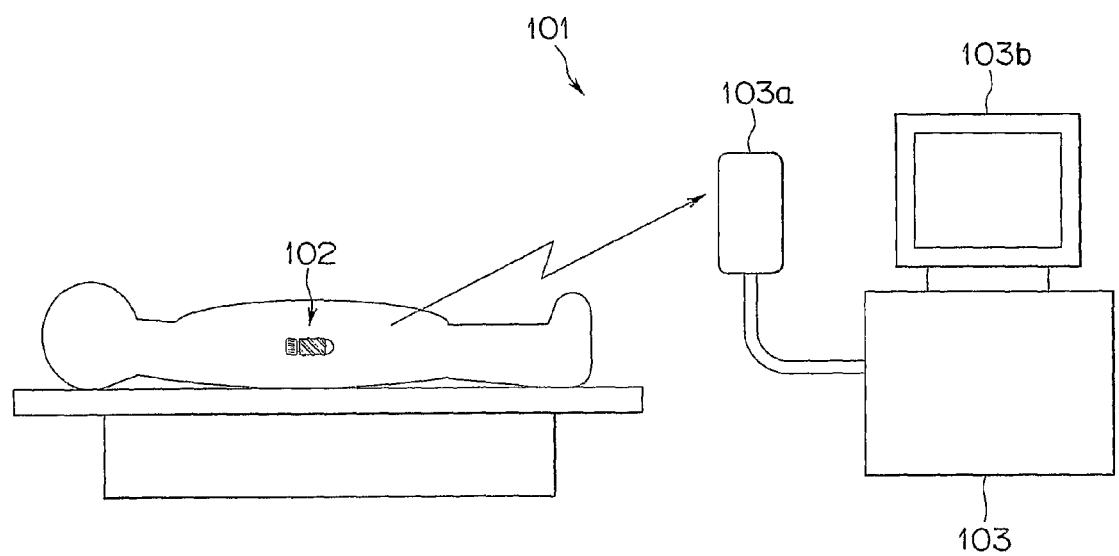
FIG. 24 is an overall configuration diagram showing a schematic configuration of a capsule medical system according to an embodiment 7 of the present invention.

As shown in FIG. 24, a capsule medical system 101 according to the embodiment 7 comprises: a capsule 102 to be inserted and propelled within the body cavity; and an external apparatus 103 installed around the subject, i.e., outside of the subject's body, for exchange of signals with the capsule 102.

The capsule 102 includes in-vivo information acquisition means for acquiring in-vivo information. The in-vivo information acquired by the in-vivo information acquisition means is transmitted from an unshown capsule-side antenna wirelessly.

The aforementioned external apparatus 103 receives the in-vivo information from the capsule 102 with an external antenna 103a, and performs signal processing for the in-vivo information. Then, the in-vivo information is displayed on a display screen of the monitor 103b.

With the present embodiment, the in-vivo image information is acquired as the in-vivo information.

That is to say, the aforementioned capsule 102 serves as a capsule endoscope for performing image capturing within the body cavity. The aforementioned external apparatus 103 performs signal processing for the image information transmitted from the aforementioned capsule 102, and displays the image, captured within the body cavity, on the display screen of the aforementioned monitor 103b.

Figure 25:
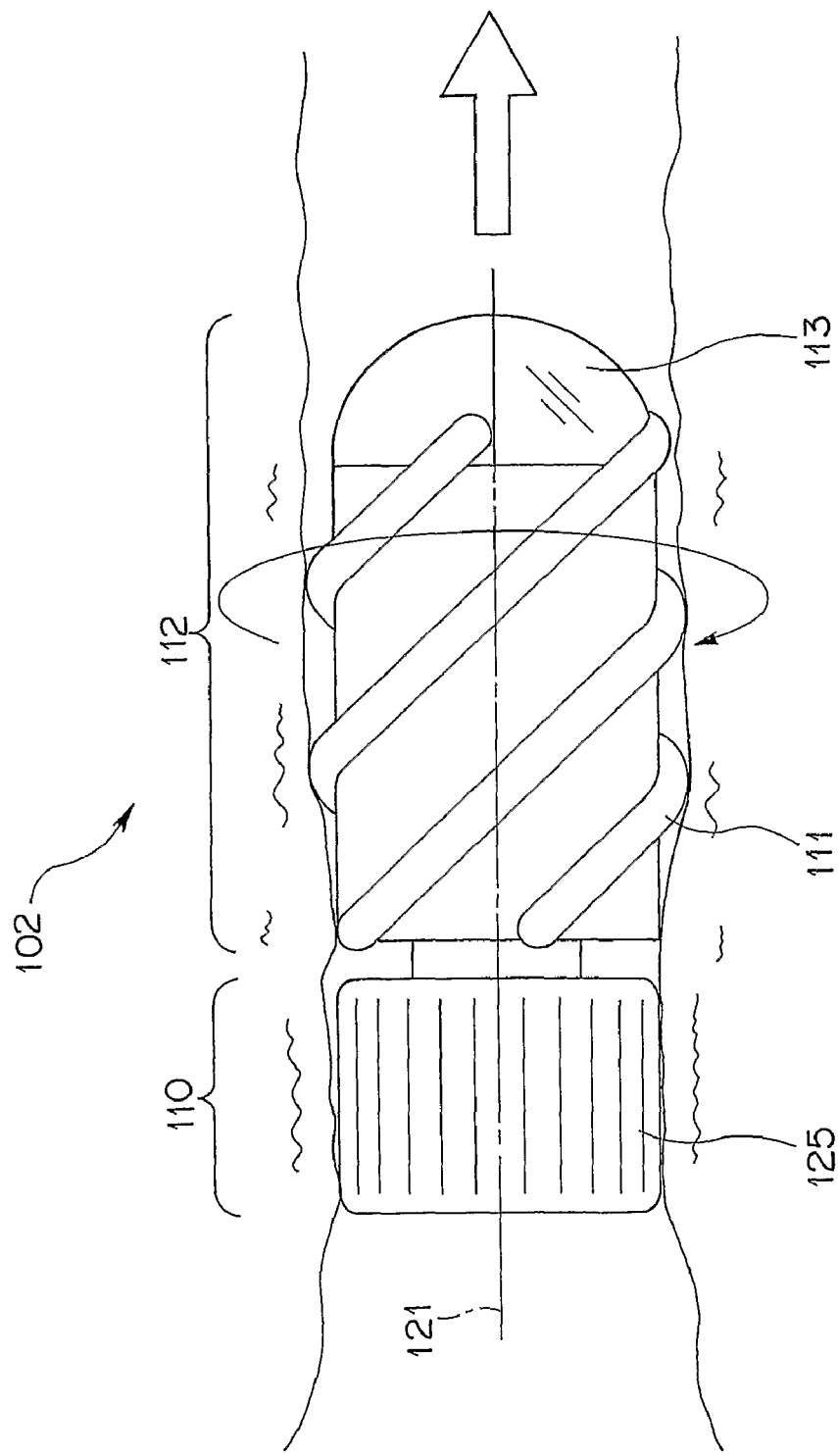
FIG. 25 is an explanatory external view of the capsule shown in FIG. 24.
Figure 26:
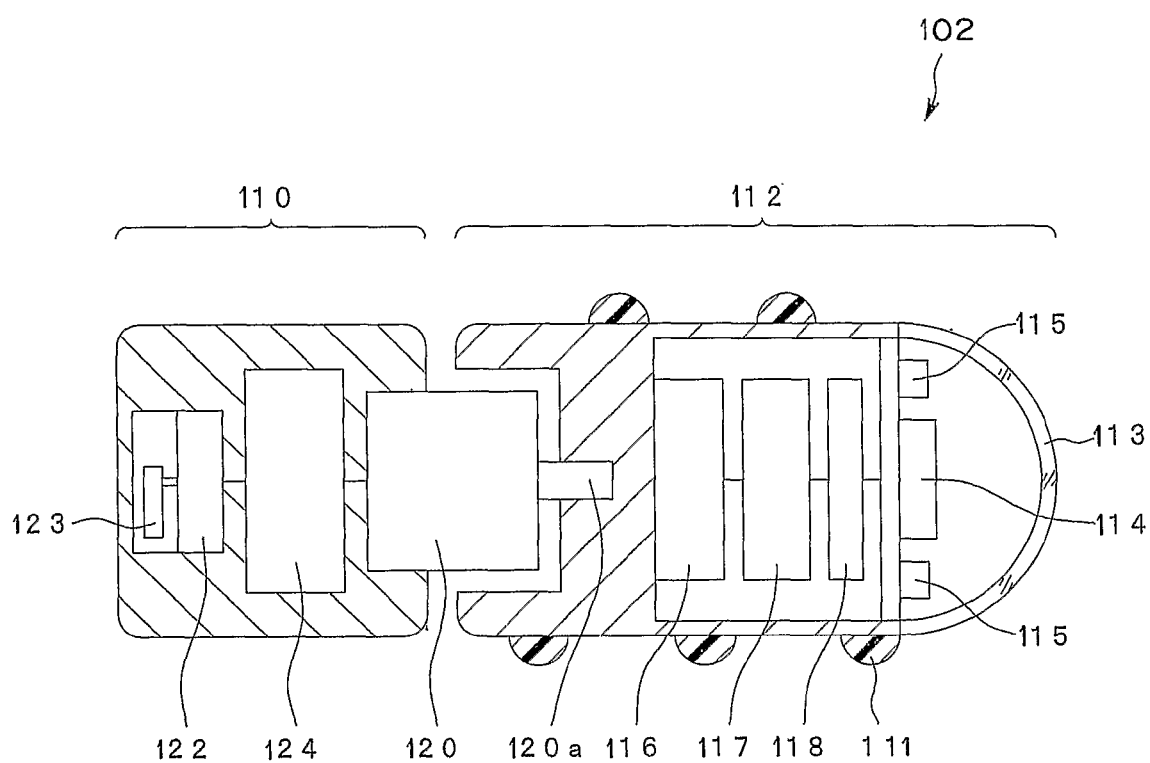
FIG. 26 is an explanatory diagram for describing the internal configuration of the capsule shown in FIG. 25.

As shown in FIGS. 25 and 26, the capsule 102 comprises a base 110 and a helical rotation propelling unit 112 which is connected to the base 110 and which includes a helical protrusion 111 on the outer face thereof.

The helical protrusion 111 is formed on the outer face of the helical rotation propelling unit 112 in a round shape and with a cross-section approximating a semicircle, which allows the helical protrusion 111 to be smoothly in contact with the inner face of the body cavity.

With the helical rotation propelling unit 112, a transparent member 113 is formed on one end thereof (which will be referred to "front end") in the shape of a hemisphere. Furthermore, an image pickup device 114 such as a CCD (Charge Coupled Device) or the like is disposed around the center of the helical rotation propelling unit 112 so as to face the transparent member 113. Furthermore, four illumination devices 115 such as LEDs (Light Emitting Diodes) or the like, are disposed around the image pickup device 114, for example.

Furthermore, the helical rotation propelling unit 112 includes a first battery 116, an image transmission unit 117, and a control circuit 118 on the rear side of the image pickup device 114 and the illumination devices 115.

The first battery 116 supplies electric power to each component included within the helical rotation propelling unit 112. The image transmission unit 117 performs signal processing and transmission processing such as modulation or the like for the captured image signal from the image pickup device 114, and transmits the image data to the external apparatus 103 via the unshown capsule-side antenna. Note that the image transmission unit 117 may include the capsule-side antenna therewithin. Alternatively, the capsule 102 includes the capsule-side antenna as a separate unit.

The control circuit 118 controls the image pickup device 114 and the illumination devices 115.

On the other hand, the base 110 includes a first motor 120 which is rotating means for rotating the helical rotation propelling unit 112. Note that the unit including a motor for rotating the helical rotation propelling unit 112 will be referred to as "base 110" hereafter.

The motor shaft 120a of the first motor 120 is fit and fixed to the rear end of the helical rotation propelling unit 112, thereby allowing the helical rotation propelling unit 112 to be rotated relatively with respect to the base 110.

With such a configuration, the helical rotation propelling unit 112 is rotated relatively with respect to the base 110 by the rotating force of the first motor 120. The helical protrusion 111 converts the rotation into the propelling force, thereby generating the propelling force in the helical-axis direction (direction of the helical axis 121).

Furthermore, the base 110 includes a second motor 122 for assisting the helical protrusion 111 of the helical rotation propelling unit 112 to remain in contact with the living body tissue. The second motor 122 includes an eccentric rotor 123 so as to serve as swinging means (vibrating means) for generating swinging (vibration).

With the capsule 102, the eccentric rotor 123 generates vibration by driving the second motor 122, and the vibration is transmitted to the helical rotation propelling unit 112 through the base 110, whereby the entire capsule is swung (vibrated).

This allows the operator to handle a situation in which the capsule 102 cannot be propelled due to the helical protrusion 111 not being in contact with the inner face of the body cavity. That is to say, the entire capsule is swung (vibrated) so as to prevent the capsule 102 from jamming, thereby returning to a normal situation in which the capsule 102 can be propelled with the helical protrusion 111 being in contact with the inner face of the body cavity. Note that electric power is supplied to the first motor 120 and the second motor 122 from a second battery 124 provided to the base 110.

Furthermore, multiple grooves 125 are formed on the outer face of the base 110 in parallel with the longitudinal axis, which serves as rotation preventing means for preventing rotation of the base 110.

This prevents the base 110 from rotating with respect to the inner wall of the body cavity without affecting propelling of the capsule 102.

Description will be made regarding the operation of the present embodiment having such a configuration.

First, the subject swallows the capsule 102 for examination of the body cavity. While the capsule 102 inserted into the body cavity passes through the body cavity such as the esophagus and so forth, image capturing is performed by the image-capturing device 114, illuminating with the illumination devices 115.

With the capsule 102, the captured image signal from the image pickup device 114 is subjected to signal processing by the image transmission unit 117, and the image signal thus obtained is subjected to transmission processing such as modulation or the like. The image signal is transmitted to the external apparatus 103 from the capsule-side antenna wirelessly.

With the external apparatus 103, the air waves received by the external antenna 103a is demodulated, and the demodulated image data is subjected to signal processing, thereby obtaining the image data. Then, the external apparatus 103 sequentially displays the image data captured by the capsule 102 on the display screen of the monitor 103b as a capsule-captured image.

Here, with the capsule 102, electric power is supplied to the first motor 120 from the second battery 124, thereby driving the first motor 120. Thus, the helical rotating propelling unit 112 fit to the motor shaft 120a of the first motor 120 is rotated.

The helical rotation propelling unit 112 receives the rotating force from the motor shaft 120a of the first motor 120. The rotating force of the first motor 120 rotates the helical rotation propelling unit 112 relatively with respect to the base 110. Note that the base 110 prevents rotation thereof with respect to the inner wall of the body cavity without affecting propelling of the capsule 102 through the grooves 125 formed on the outer face thereof.

The capsule 102 converts the rotation of the helical rotation propelling unit 112 into the propelling force thereof with the helical protrusion 111 of the helical rotation propelling unit 112 being in contact with the inner face of the body cavity, like a male screw thread inserted into a female screw groove.

Thus, the capsule 102 generates the propelling force in the helical-axis direction (direction of the helical axis 121) by actions of the helical rotation propelling unit 112, thereby moving forward.

Thus, the capsule 102 generates the propelling force within the body cavity by actions of the helical rotation propelling unit 112 with high efficiency.

Figure 27:
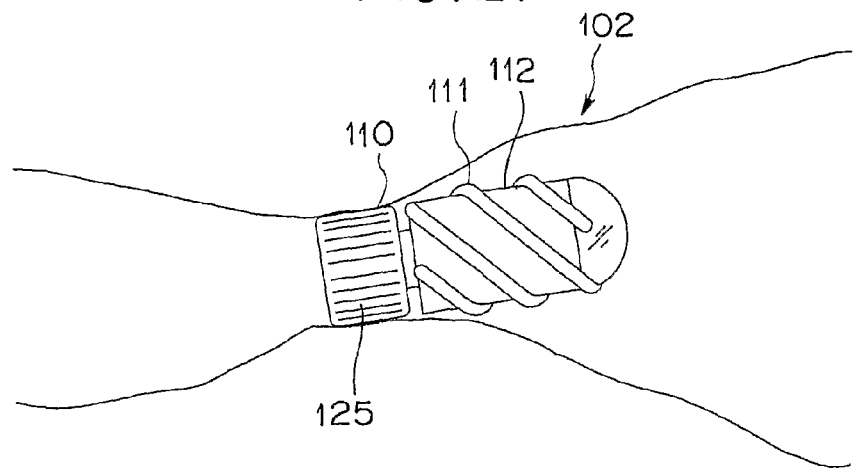
FIG. 27 is an explanatory diagram showing the capsule shown in FIG. 25 immediately prior to passing through a narrow part of the lumen within the body cavity.

Let us consider a situation in which the capsule 102 passes through a narrow path within the body cavity as shown in FIG. 27. Let us say that there is a wide space in the forward direction.

In such a situation, the helical rotation propelling unit 112 is not in contact with the inner face of the body cavity, leading to a problem that the capsule 102 cannot be moved forward.

Figure 28:
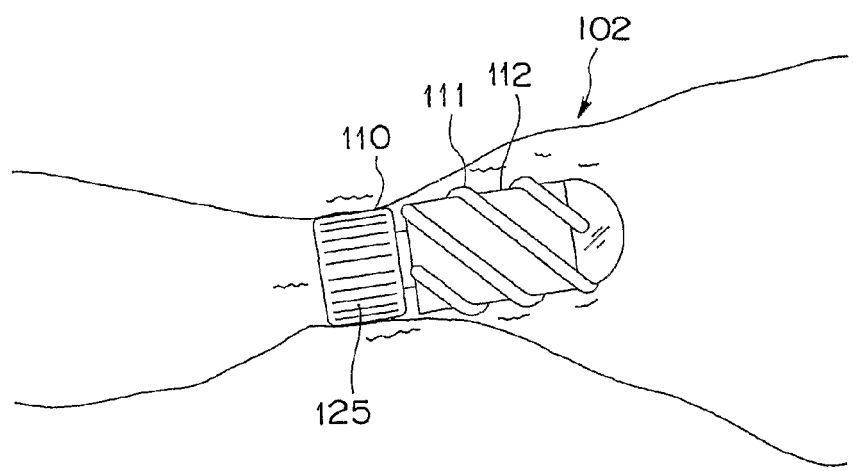
FIG. 28 is an explanatory diagram showing the capsule performing swinging motion (vibration motion) for releasing from the narrow part of the lumen within the body cavity following the situation shown in FIG. 27.
Figure 29:
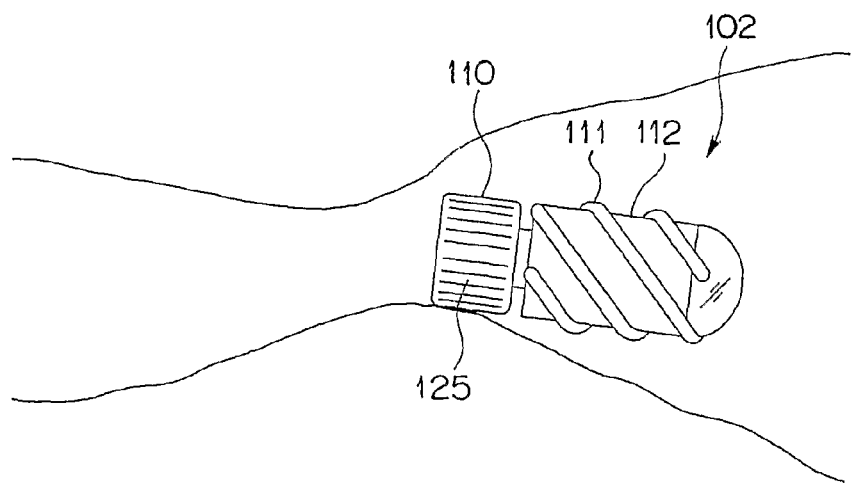
FIG. 29 is an explanatory diagram showing the capsule immediately after releasing from the narrow part of the lumen within the body cavity following the situation shown in FIG. 28.

In this case, the second motor 122 of the capsule 102 is driven as shown in FIG. 28.

In the capsule 102, the eccentric rotor 123 generates vibration by driving the second motor 122. The vibration is transmitted from the base 110 to the helical rotation propelling unit 112, whereby the entire capsule is swung (vibrated).

The capsule 102 is released from the narrow space of the path of the body cavity by the vibration (swinging), and returns to a normal situation in which the capsule 102 is propelled by rotation of the helical rotation propelling unit 112 with the helical rotation propelling unit 112 being contact with the inner face of the body cavity.

This allows the operator to handle a situation in which the capsule 102 cannot be propelled due to the helical protrusion 111 not being in contact with the inner face of the body cavity. That is to say, the entire capsule is swung (vibrated) so as to prevent the capsule 102 from jamming, thereby returning to a normal situation in which the capsule 102 can be propelled with the helical protrusion 111 being in contact with the inner wall of the body cavity.

Thus, with the capsule medical system 101 according to the present embodiment, the capsule 102 generates the propelling force thereof within the body cavity by actions of the helical rotation propelling unit 112 with high efficiency.

With the capsule 102, the image pickup device 114 is included within the helical rotation propelling unit 112, leading to a problem that rotating capsule-captured images are obtained.

In order to solve the aforementioned problem, angle detecting means is provided to the first motor 120, and the capsule-captured image is subjected to angle correction based upon the angle information detected by the angle detecting means, thereby performing rotation processing for the image. Alternatively, an angular speed detecting means is provided, and the angle is obtained based upon the integral value of the information obtained from the angular speed detecting means.

Figure 30:
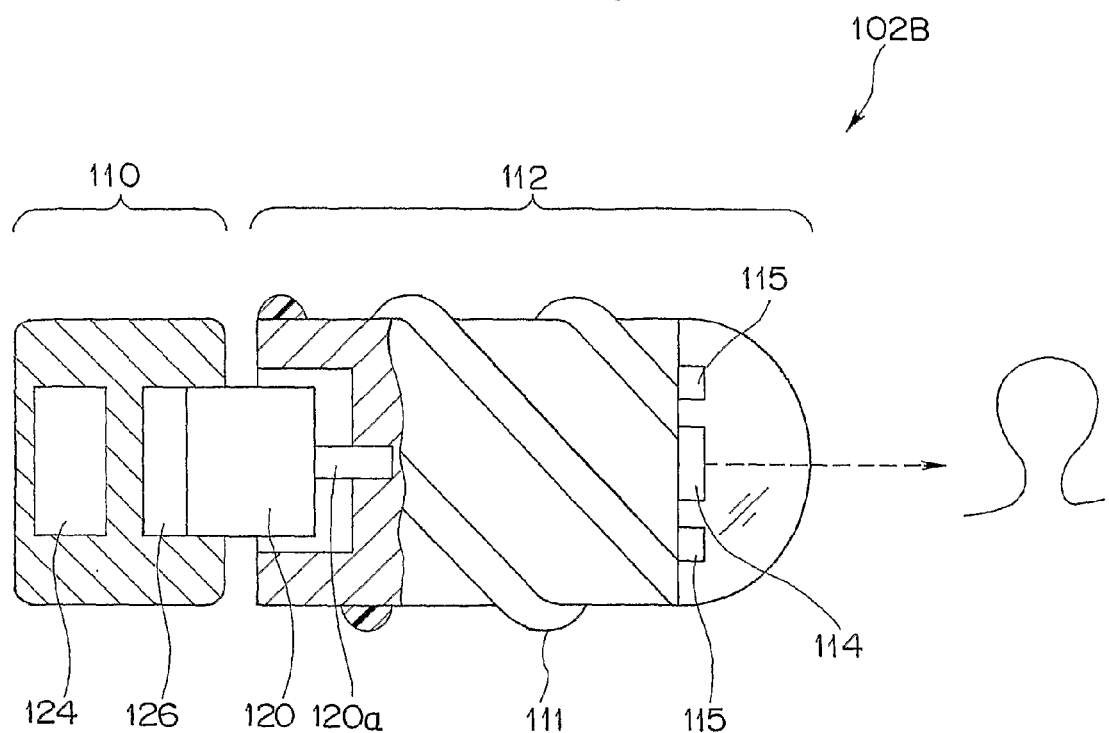
FIG. 30 is a schematic diagram which shows the capsule including an angle detection sensor.

FIG. 30 shows a capsule 102B including an angle detection sensor 126 provided to the first motor 120.

With such a configuration, the image transmission unit 117 transmits the captured image signal, output from the image pickup device 114, to the external apparatus 103 in a form correlated with the angle information from the angle detection sensor 126.

Figure 31:
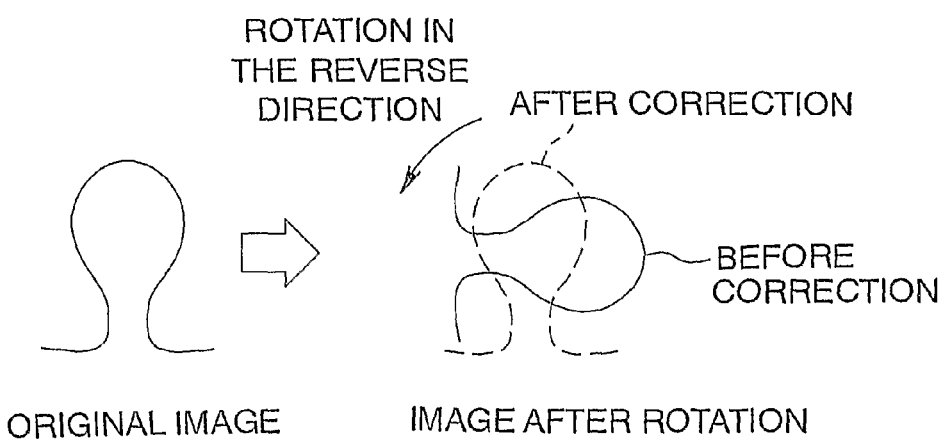
FIG. 31 is a conceptual diagram for describing angle correction processing performed based upon angle information detected by the angle detection sensor shown in FIG. 30.

Then, the external apparatus 103 performs angle correction processing for the image signal based upon the angle information received from the capsule 102 as shown in FIG. 31.

Note that an arrangement may be made in which the angle correction processing is performed by the image transmission unit 117. With such an arrangement, the image transmission unit 117 may transmit the image signal, which has been obtained by performing the angle correction processing for the captured image signal from the image pickup device 114 based upon the angle information from the angle detection sensor 126, to the external device 103.

Thus, the capsule 102B obtains the capsule-captured image without rotation.

Figure 32:
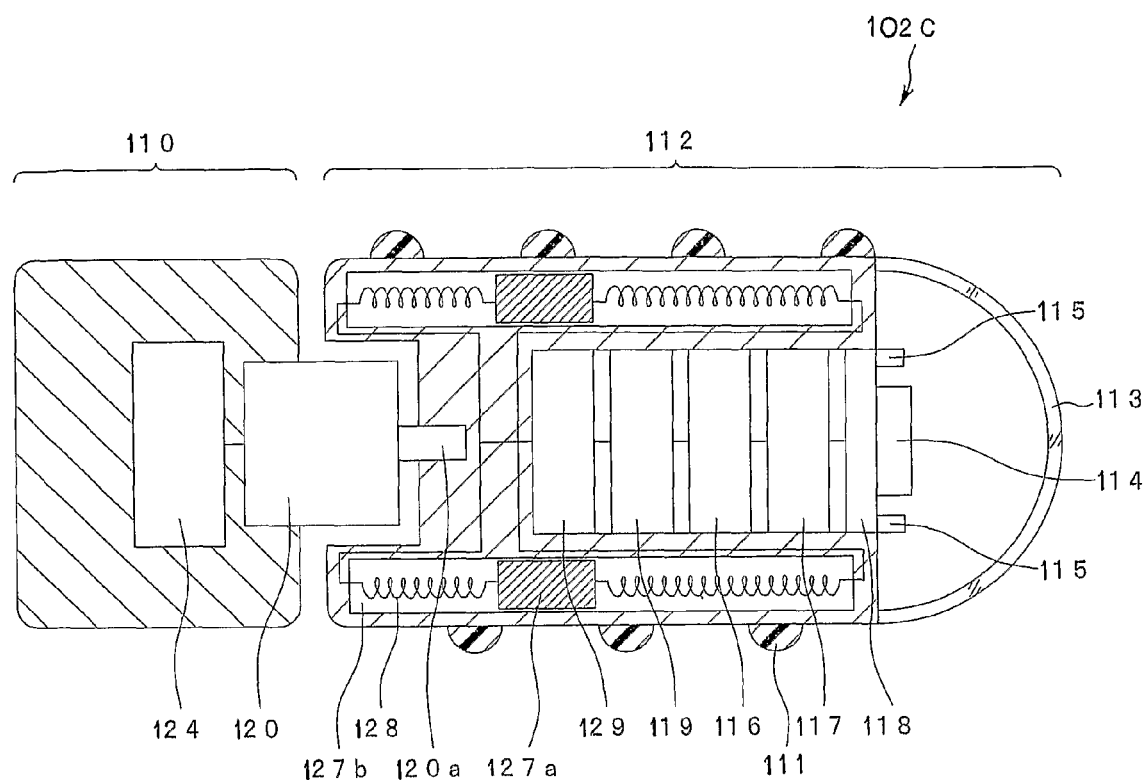
FIG. 32 is a sectional view which shows the internal configuration of the capsule including swinging means (vibration means) employing shape memory alloy, which serves as helical-structure contact means.

Also, the capsule includes the swinging means (vibration means) which are helical-structure contact means formed of shape memory alloy, instead of employing the second motor 122, as shown in FIG. 32.

FIG. 32 shows a capsule 102C employing the swinging means (vibration means) formed of SMA (Shape Memory Alloy), which are provided to the helical rotation propelling unit 112.

More Specifically, the capsule 102C has a space 127b formed around the outer face of the helical rotation propelling unit 112 for storing a weight 127a so as to allow movement thereof. The weight 127a is stored within the space 127b with both ends connected to SMA coils 128 formed of SMA wires. With the present embodiment, application of electricity to the SMA coils 128 causes extension/contraction thereof, thereby enabling reciprocating motion of the weight 127a.

Furthermore, the helical rotation propelling unit 112 includes an SMA driving circuit 129 for applying electricity to the SMA coils 128.

With the capsule 102C, extension/contraction of the front-side SMA coil 128 or the rear-side SMA coil 128 is performed according to a signal from the SMA driving circuit 129, leading to reciprocating motion of the weight 127a. This changes the center of gravity of the entire capsule.

Thus, the capsule 102C has a function for continuously changing the center of gravity of the entire capsule, thereby generating swinging (vibration) with the same or greater magnitude as compared with an arrangement described in the embodiment 7. Note that with the capsule 102C, conductive polymer (artificial muscle) or a linear actuator may be employed instead of the SMA coil 128.

Also, the capsule may include the helical-structure contact means having a configuration which allows the helical rotation propelling unit 112 to swing with respect to the base 110.

Figure 33:
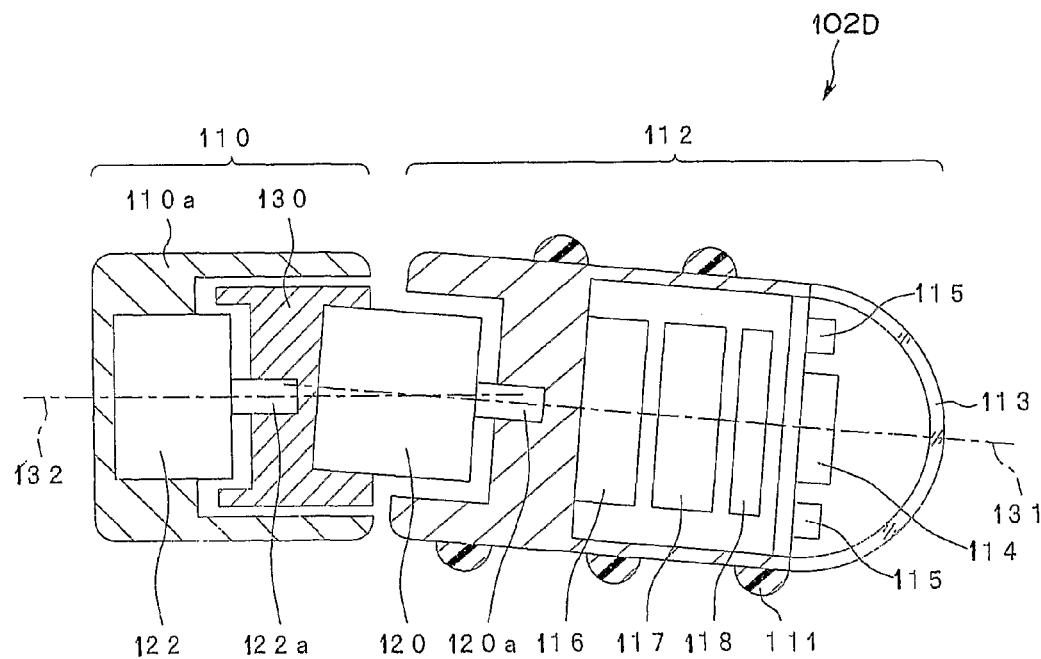
FIG. 33 is a sectional view which shows the internal configuration of the capsule including helical-structure contact means which allows swinging of a helical rotation propelling unit with respect to a base.

FIG. 33 shows a capsule 102D including the base 110 divided into two units each of which has a rotating motor.

More specifically, with the capsule 102D, the first motor 120 for rotating the helical rotation propelling unit 112 is fit and fixed to an inclining base 130 so as to incline with respect to the inclining base 130.

A motor shaft 122a of the second motor 122 is fit and fixed to the rear end of the inclining base 130, thereby allowing rotation of the inclining base 130 and the helical rotation propelling unit 112 in the form of a single unit by driving the second motor 122. Note that the second motor 122 is provided to a base main unit 110a.

Figure 34:
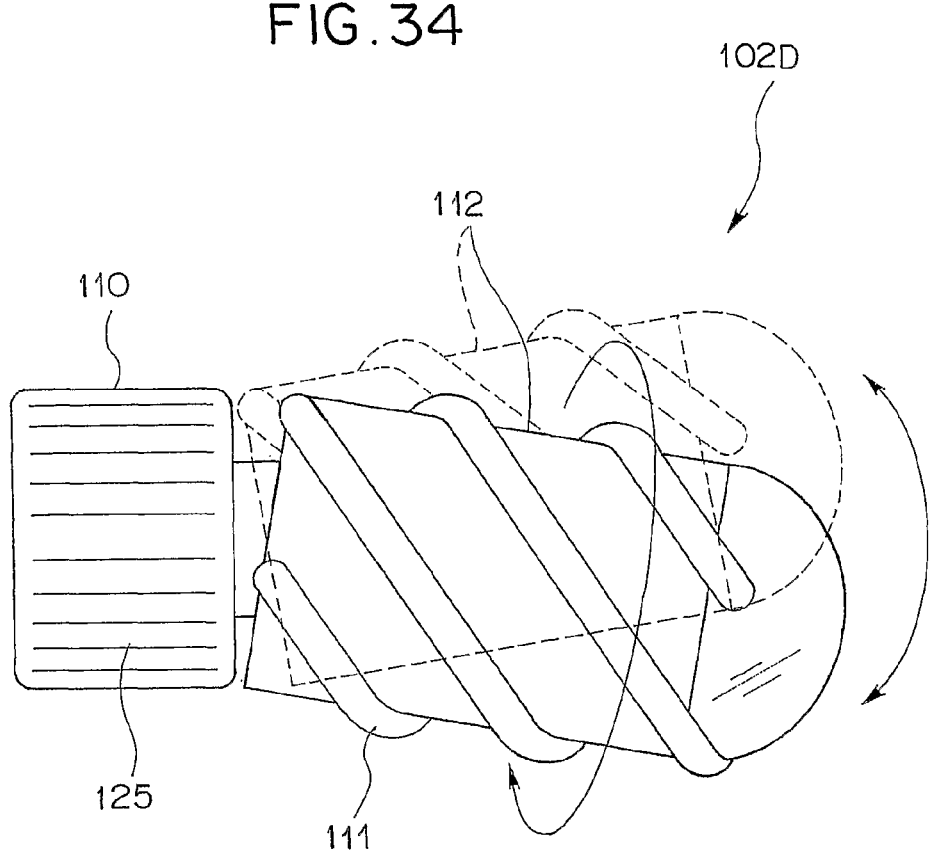
FIG. 34 is a diagram which shows the operation of the capsule shown in FIG. 33.

With the capsule 102D having such a configuration, the rotating axis 131 of the helical rotation propelling unit 112 slants with respect to the center axis 132 of the inclining base 130. Such a configuration allows rotation of the helical rotation propelling unit 112 while swinging with respect to the base 110 as shown in FIG. 34.

Thus, the capsule 102D has the same advantages as with the embodiment 7. Furthermore, with the capsule 102D, the helical rotation propelling unit 112 is swung with respect to the base 110 at all times, thereby improving the frequency of the helical rotation propelling unit 112 being in contact with the inner wall of the body cavity. This facilitates propelling of the capsule 102D.

Also, the capsule may include the helical-structure contact means having a configuration in which the helical rotation propelling unit 112 is mounted to the base 110 with a certain offset between the axes thereof.

Figure 35:
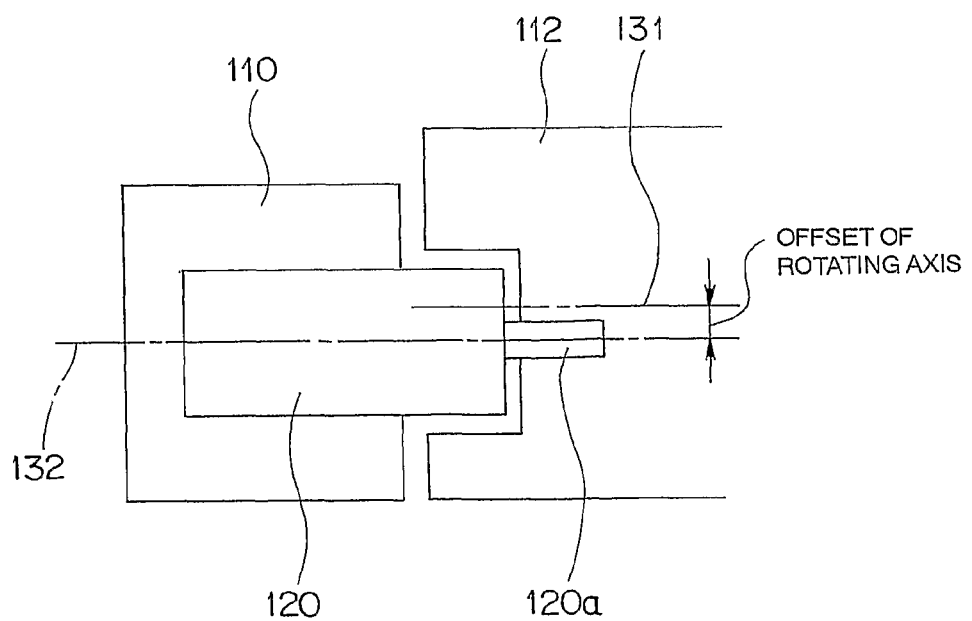
FIG. 35 is a principal-component explanatory diagram which shows a capsule having a configuration in which the motor shaft of a first motor is fit and fixed to the rear end of the helical rotation propelling unit with a certain offset between the center axis of the helical rotation propelling unit and the rotary axis of the first motor.

FIG. 35 shows a capsule 102E having a configuration in which the motor shaft 120a of the first motor 120 is fit and fixed to the rear end of the helical rotation propelling unit 112 with a certain offset between the center axis 132 of the helical rotation propelling unit 112 and the rotating axis 131 of the first motor 120.

Figure 36:
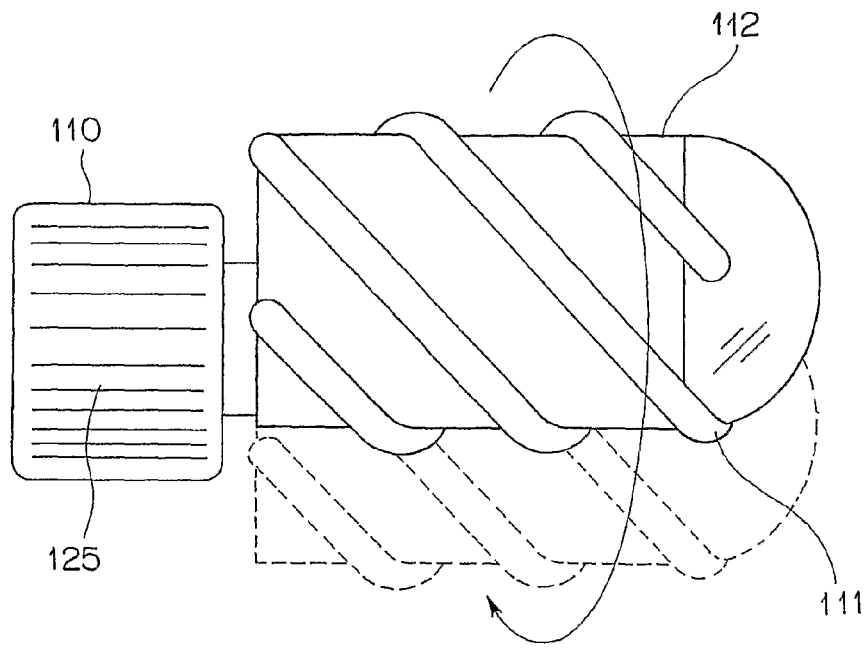
FIG. 36 is a diagram which shows the operation of a capsule including helical-structure contact means having the configuration shown in FIG. 35 so that the helical rotation propelling unit is mounted to the base with a certain offset between the axes thereof.

With the capsule 102E having such a configuration, the helical rotation propelling unit 112 is mounted to the base 110 with a certain offset between the axes thereof. Thus, with the capsule 102E, the helical rotation propelling unit 112 is rotated while swinging with respect to the base 110 at all times as shown in FIG. 36.

Thus, the capsule 102E has the same advantages as with the aforementioned capsule 102D.

Also, the capsule may include the helical-structure contact means having a configuration in which the base 110 is divided into two units each of which includes a rotating motor in the same way as with the capsule 102D, and the helical rotation propelling unit 112 is mounted to the base 110 with a certain offset between the axis the axes therebetween in the same way as with the capsule 102E.

Figure 37:
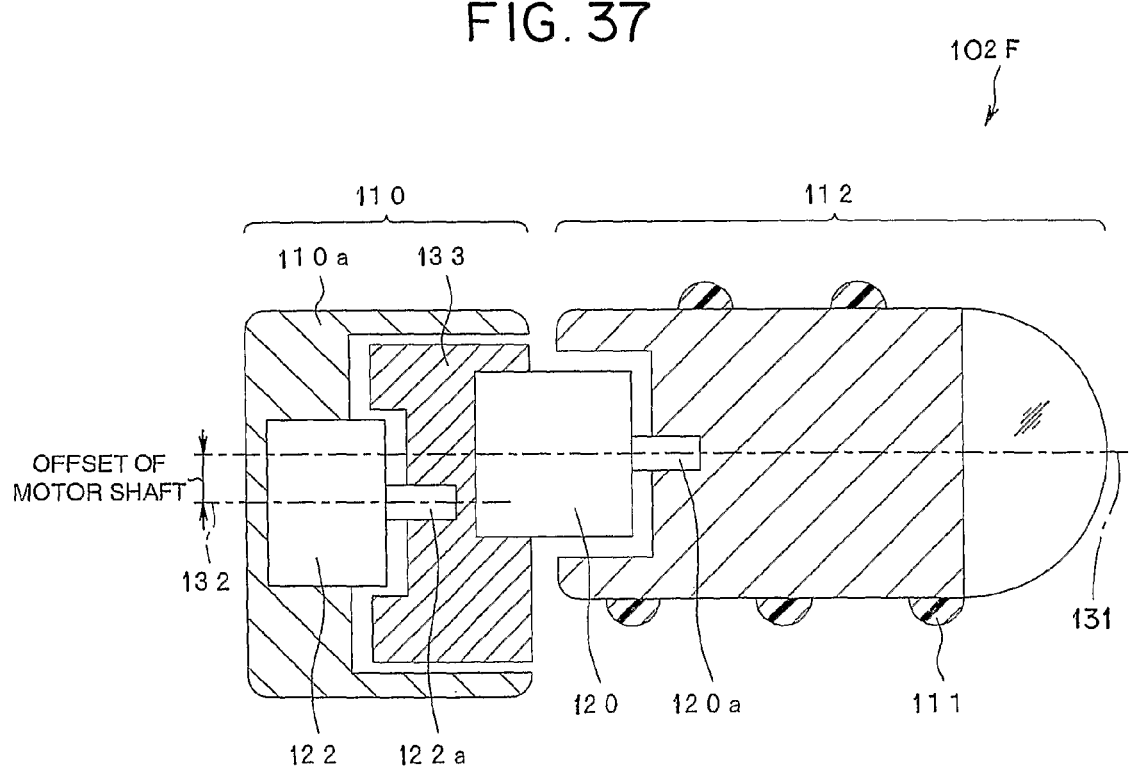
FIG. 37 is a sectional view which shows the internal configuration of a capsule having a configuration in which the base is divided into two portions each of which includes a motor, and the helical rotation propelling unit is mounted to the base with a certain offset between the axes therebetween, which serves as helical-structure contact means.

FIG. 37 shows a capsule 102F having a configuration in which the first motor 120 for rotating the helical rotation propelling unit 112 is fit and fixed to a base 133. Furthermore, the motor shaft 122a of the second motor 122 is fit and fixed to the rear end of the base 133 with a certain offset between the rotating axis 132 of the second motor 122 and the rotating axis 131 of the first motor 120. Such a configuration allows rotation of the base 133 and the helical rotation propelling unit 112 in the form of a single unit by driving the second motor 122. Note that the second motor 122 is provided to the base main unit 110a.

Figure 38:
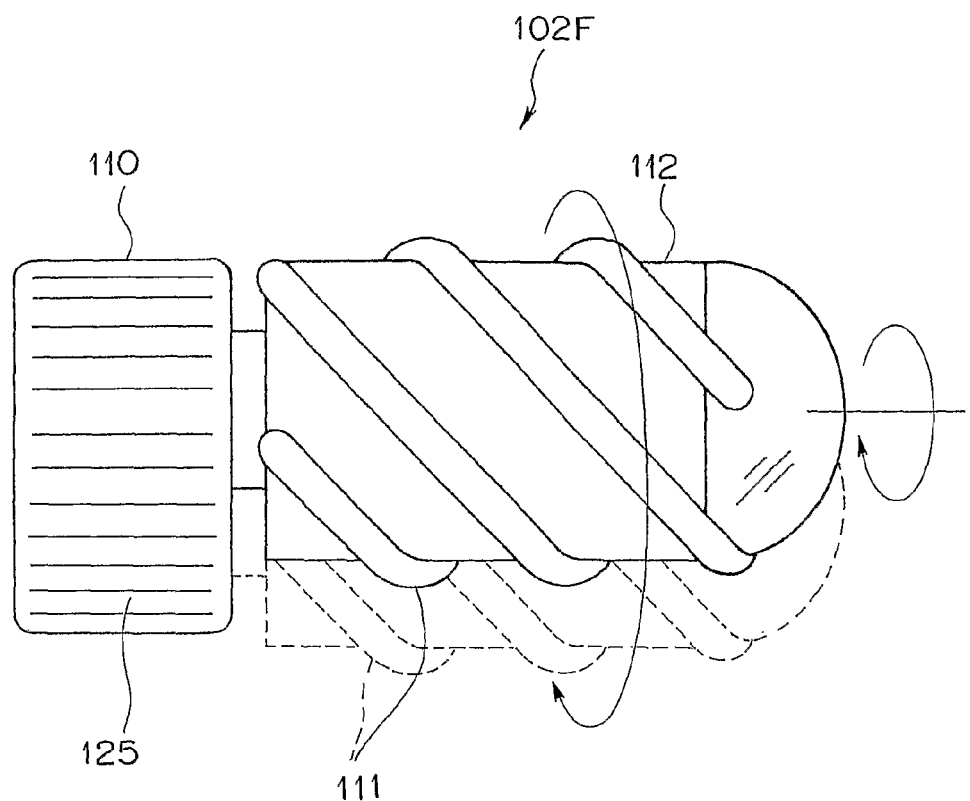
FIG. 38 is an explanatory diagram which shows the operation of the capsule shown in FIG. 37.

With the capsule 102F having such a configuration, the helical rotation propelling unit 112 is mounted to the base 110 with a certain offset between the axes thereof. Thus, with the capsule 102F, the helical rotation propelling unit 112 is rotated about its center axis 132 while swinging with respect to the base 110 at all times as shown in FIG. 38.

Thus, the capsule 102F has the same advantages as with the aforementioned capsule 102E.

Also, the capsule may have the helical-structure contact means having a configuration which allows the helical rotation propelling unit 112 to be bent.

Figure 39:
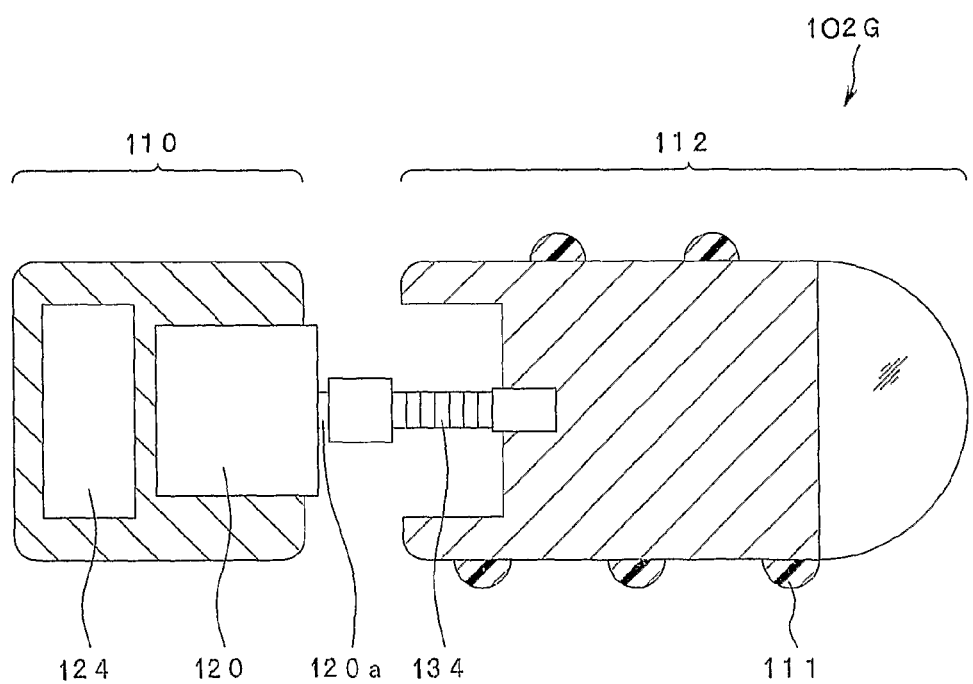
FIG. 39 is a schematic sectional view which shows the internal configuration of the capsule including helical-structure contact means which allows the helical rotation propelling unit to be bent.

FIG. 39 shows a capsule 102G having a configuration in which the first motor 120 and the helical rotation propelling unit 112 are joined with a flexible shaft 134 having a suitable flexibility, thereby allowing the helical rotation propelling unit 112 to be bent. That is to say, the aforementioned flexible shaft 134 serves as helical-structure bending means.

Figure 40:
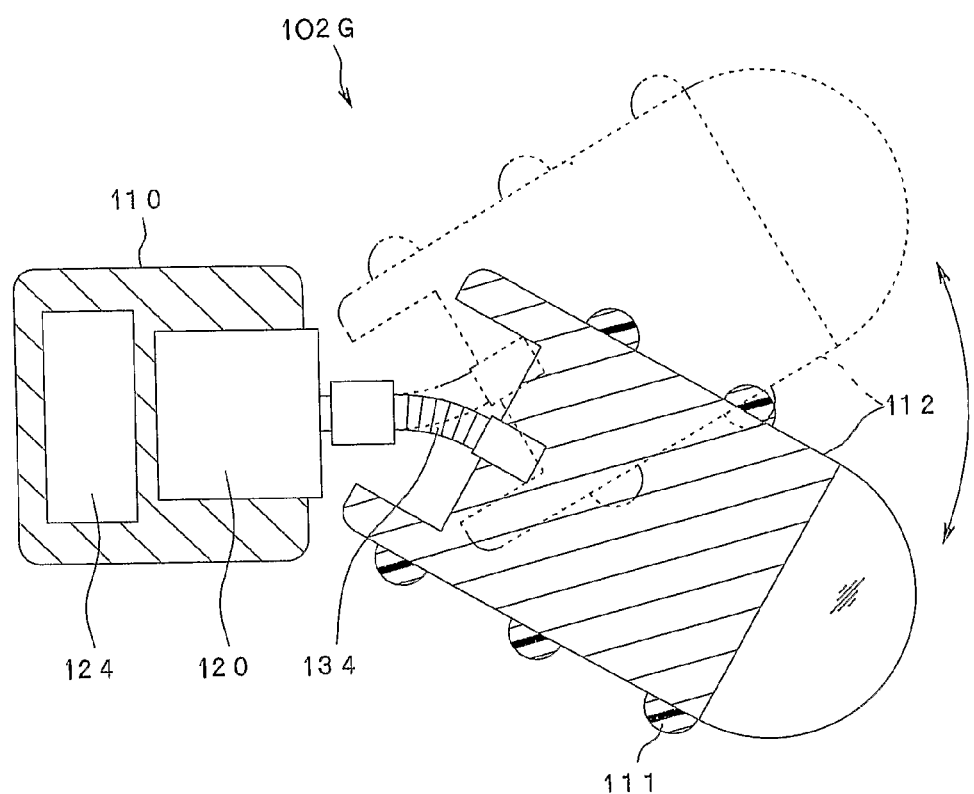
FIG. 40 is an explanatory diagram which shows the operation of the capsule shown in FIG. 39.

With the capsule 102G having such a configuration, the helical rotation propelling unit 112 inclines with respect to the base 110 following the external force without great resistance while rotating, as shown in FIG. 40.

Figure 41:
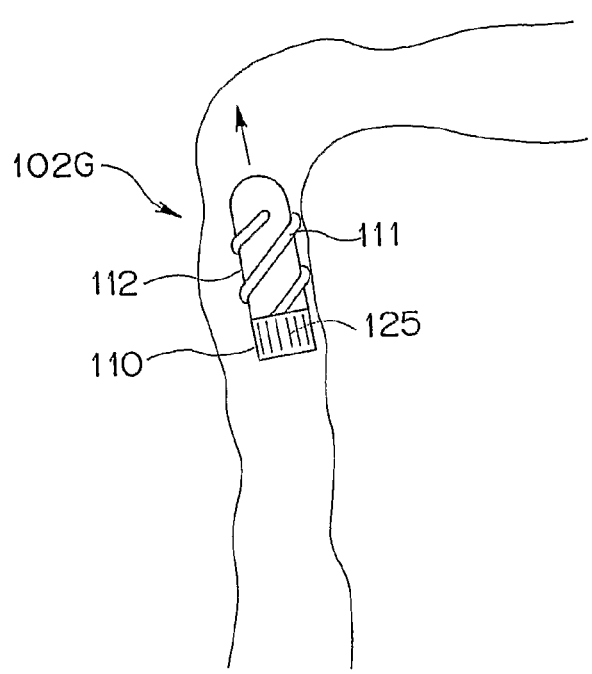
FIG. 41 is an explanatory diagram which shows the capsule shown in FIG. 39 immediately prior to passing through a curve of the lumen within the body cavity.
Figure 42:
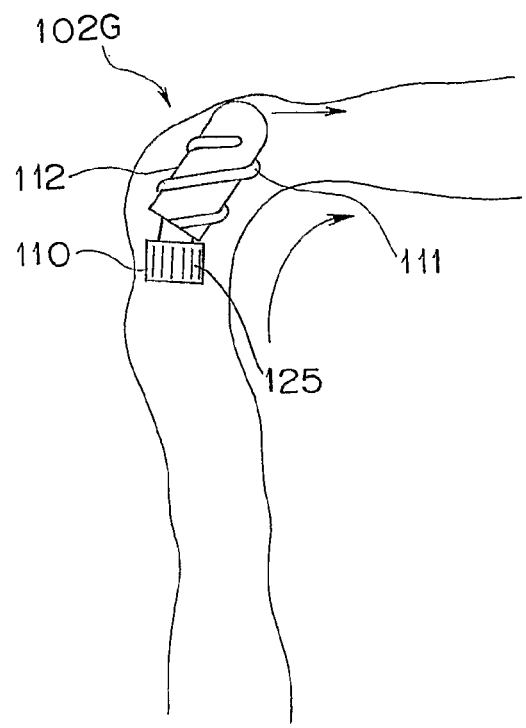
FIG. 42 is an explanatory diagram which shows the capsule passing through the curve of the lumen within the body cavity following the situation shown in FIG. 41.

Thus, the capsule 102G has a function of handling a situation in which the capsule 102G has reached the curve of the body cavity as shown in FIG. 41. That is to say, upon the helical rotation propelling unit 112 coming in contact with the inner wall of the body cavity, the helical rotation propelling unit 112 turns following the curve, thereby facilitating passing thereof through the curve, as shown in FIG. 42.

Furthermore, with the capsule 102G, the helical rotation propelling unit 112 is rotated while swinging due to the centrifugal force of rotation. Thus, the capsule 102G has the same advantages as those of the capsule 102E.

Also, the capsule may have the bending means for bending the helical rotation propelling unit 112.

Figure 43:
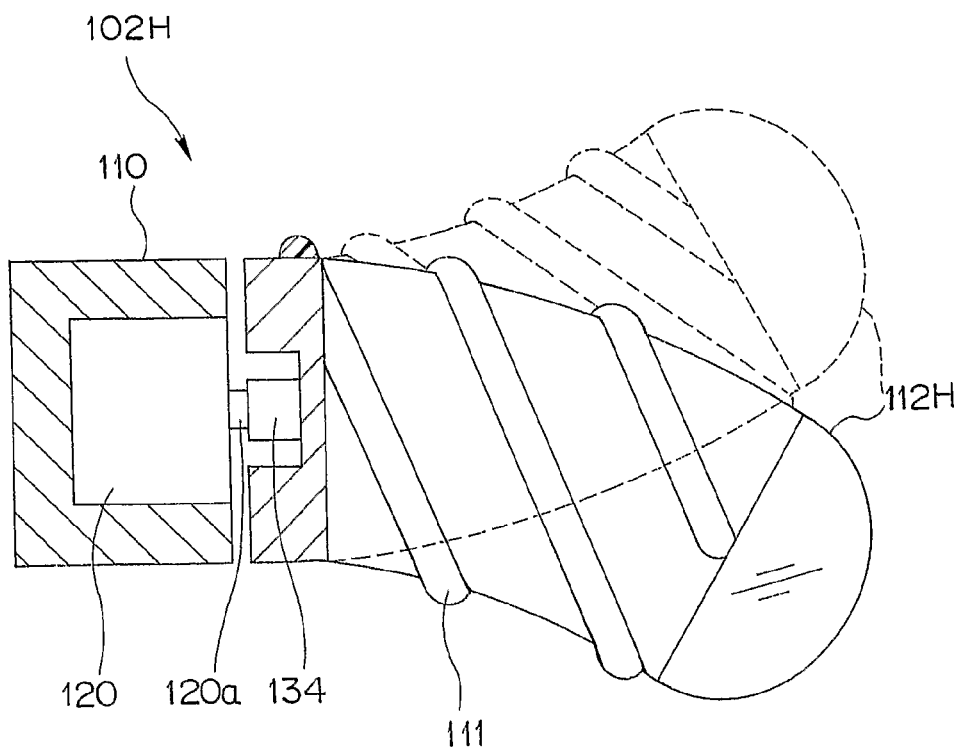
FIG. 43 is an explanatory diagram which shows a capsule including bending means which allows the helical rotation propelling unit to be bent.

FIG. 43 shows a capsule 102H having a configuration in which the helical rotation propelling unit 112H is formed of a flexible member for allowing change in the shape thereof following the external force. In such a configuration, the helical rotation propelling unit 112H itself serves as the bending means.

Thus, the capsule 102H has the same advantages as with the aforementioned capsule 102G.

Note that with the present embodiment, the present invention is applied to a capsule which serves as a capsule endoscope having a function for performing image capturing within the body cavity. However, the present invention is not restricted to such an arrangement. Also, the present invention may be applied to a tissue collecting capsule medical device including collecting means for collecting a tissue sample, a medicine carrying capsule medical device for carrying and releasing medicine, and a cautery capsule medical device for cauterizing the tissue.

Embodiment 8

Next, description will be made regarding an embodiment 8 according to the present invention with reference to FIGS. 44 through 54.

Description has been made in the embodiment 7 regarding an arrangement in which the single helical rotation propelling unit 112 is connected to the base 110. On the other hand, with the embodiment 8, two helical rotation propelling units 112 are provided with the base 110 as the center. The other components are generally the same as those of the aforementioned embodiment 7. Accordingly, the same components are denoted by the same reference numerals, and description thereof will be omitted.

Figure 44:
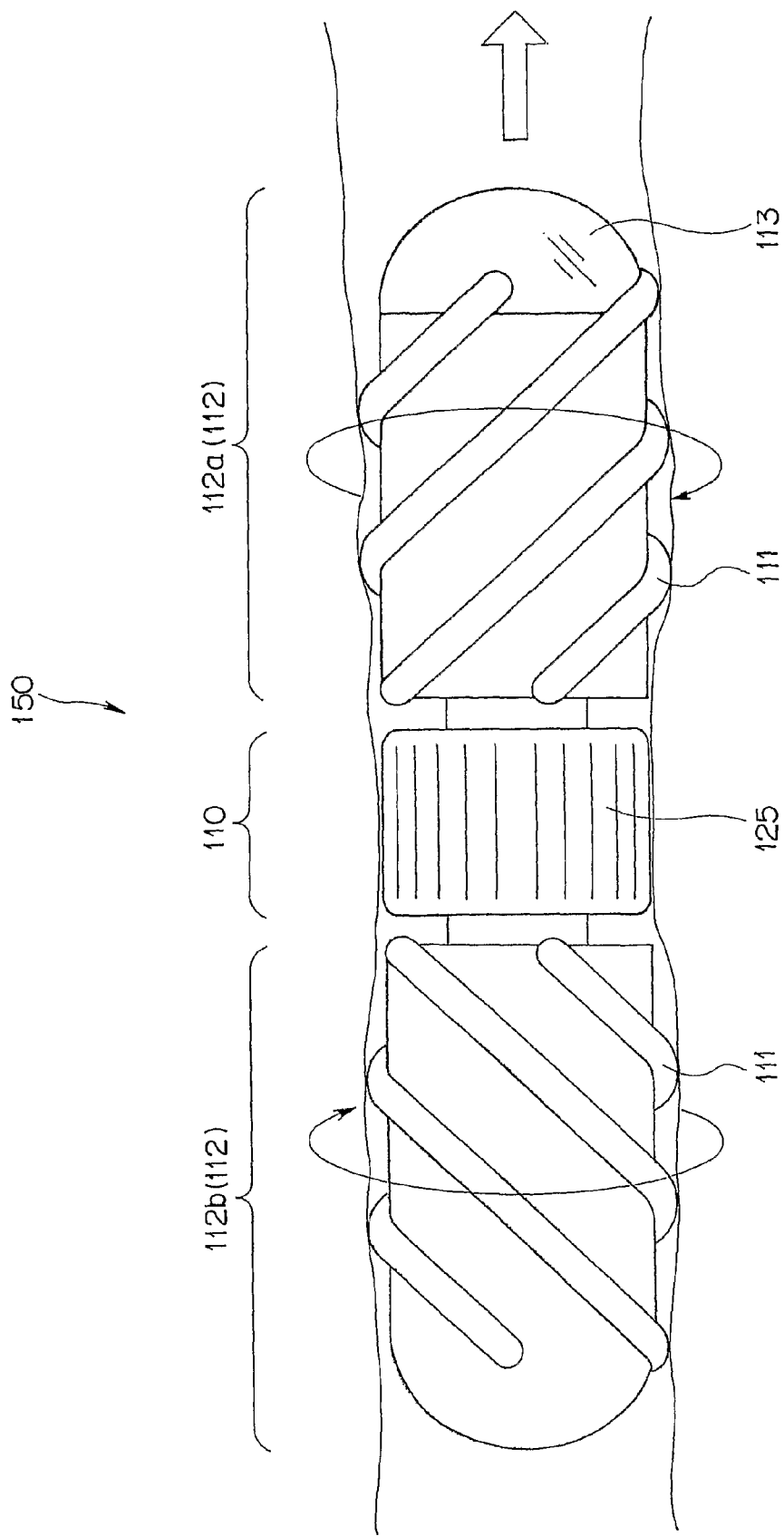
FIG. 44 is an external view which shows a capsule according to an embodiment 8.
Figure 45:
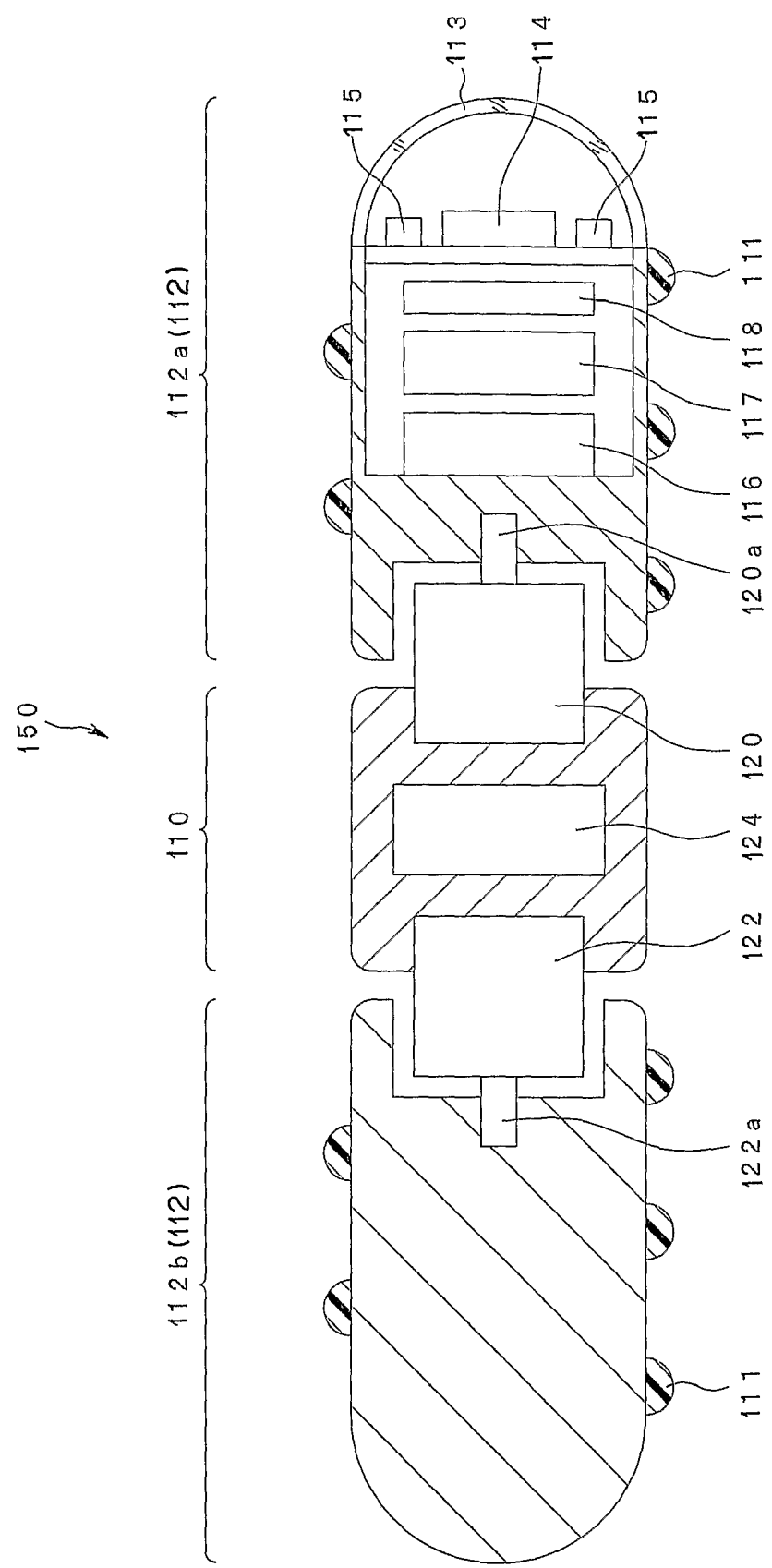
FIG. 45 is a sectional view which shows the internal configuration of the capsule shown in FIG. 44.

As shown in FIGS. 44 and 45, a capsule 150 according to the embodiment 8 has a configuration having the two helical rotation propelling units 112 with the base 110 as the center.

More specifically, the aforementioned capsule 150 comprises: the base 110; the first motor 120 mounted to the base 110; a front-side helical rotation propelling unit 112a and a rear-side helical rotation propelling unit 112b having a function of rotating thereof relatively with respect to the base 110 by driving the first motor 120 and the second motor 122 mounted to the base 110.

The front-side helical rotation propelling unit 112a and the rear-side helical rotation propelling unit 112b have the helical protrusions 111 formed on the outer face thereof, respectively, with the spiral directions different from each other.

Note that description will be made with the viewing direction of the image pickup device 114 as the front-side direction.

The base 110 includes: the first motor 120 for rotating the front-side helical rotation propelling unit 112*a*; the second motor 122 for rotating the rear-side helical rotation propelling unit 112*b*; and the second battery 124 for supplying electric power for driving the first motor 120 and the second motor 122.

The aforementioned capsule 150 having such a configuration has a function for handling a situation in which one helical rotation propelling unit 112 (the front-side helical rotation propelling unit 112*a* or the rear-side helical rotation propelling unit 112*b*) generates no propelling force due to the helical rotation propelling unit 112 not being in contact with the inner wall of the body cavity. Even in such a case, the other helical rotation propelling unit 112 (the rear-side helical rotation propelling unit 112*b* or the front-side helical rotation propelling unit 112*a*) generates propelling force with the helical rotation propelling unit 112 being in contact with the inner wall of the body cavity, thereby propelling the capsule 150.

Also, the capsule may have the helical-structure contact means having a function of applying electric stimulus.

Figure 46:
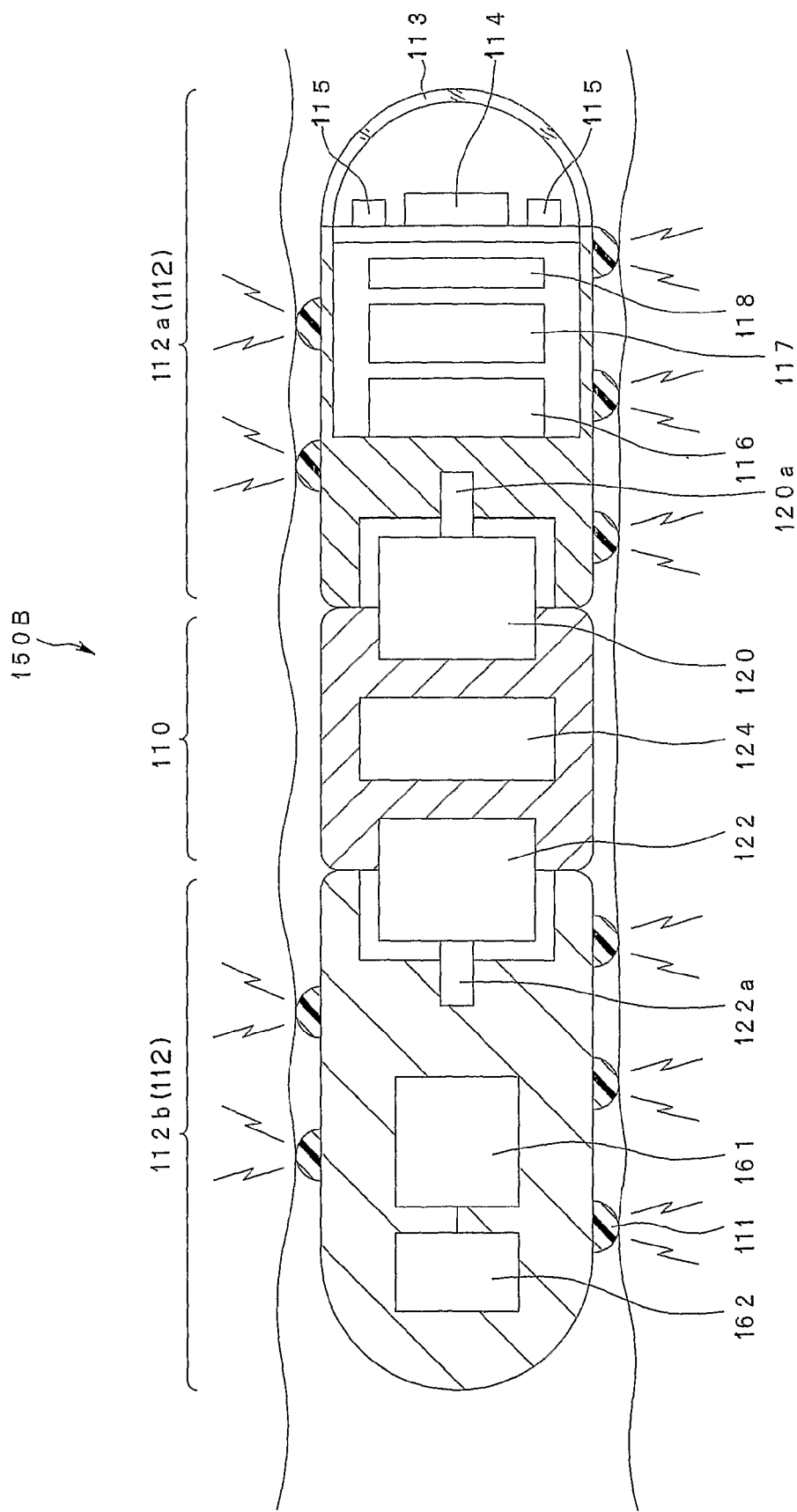
FIG. 46 is a sectional view which shows the internal configuration of a capsule including helical-structure contact means having a function of applying electric stimulus.

FIG. 46 shows a capsule 150B having a function of applying electric stimulus so as to contract the intestinal tract which is the lumen within the body cavity, as shown in FIG. 46. This assists in maintaining the state in which the helical rotation propelling unit 112 is in contact with the inner wall of the intestinal tract at all times.

More specifically, the capsule 150B comprises: an electric stimulus control circuit 161 for outputting an electric signal serving as an electric stimulus to an unshown electrode formed on the helical protrusion 111; and a third battery 162 for supplying electric power for driving the electric stimulus control circuit 161. Note that with the helical protrusion 111, one end is electrically connected to the electric stimulus control circuit 161, and the other end thereof is electrically connected to the electric stimulus control circuit 161 through an unshown slip ring, thereby forming a closed circuit.

The capsule 150B having such a configuration has a function of applying electric stimulus to the intestinal tract which is a lumen within the body cavity through the helical protrusion 111 so as to cause contraction thereof. This assists in maintaining the state in which the base 110 and the helical rotation propelling unit 112 (the front-side helical rotation propelling unit 112*a* or the rear-side helical rotation propelling unit 112*b*) are in contact with the inner wall of the intestinal tract at all times, thereby propelling the capsule 150B in a sure manner.

Also, the capsule may include the helical-structure contact means having a suction mechanism for applying suction to the inner wall of the body cavity.

Figure 47:
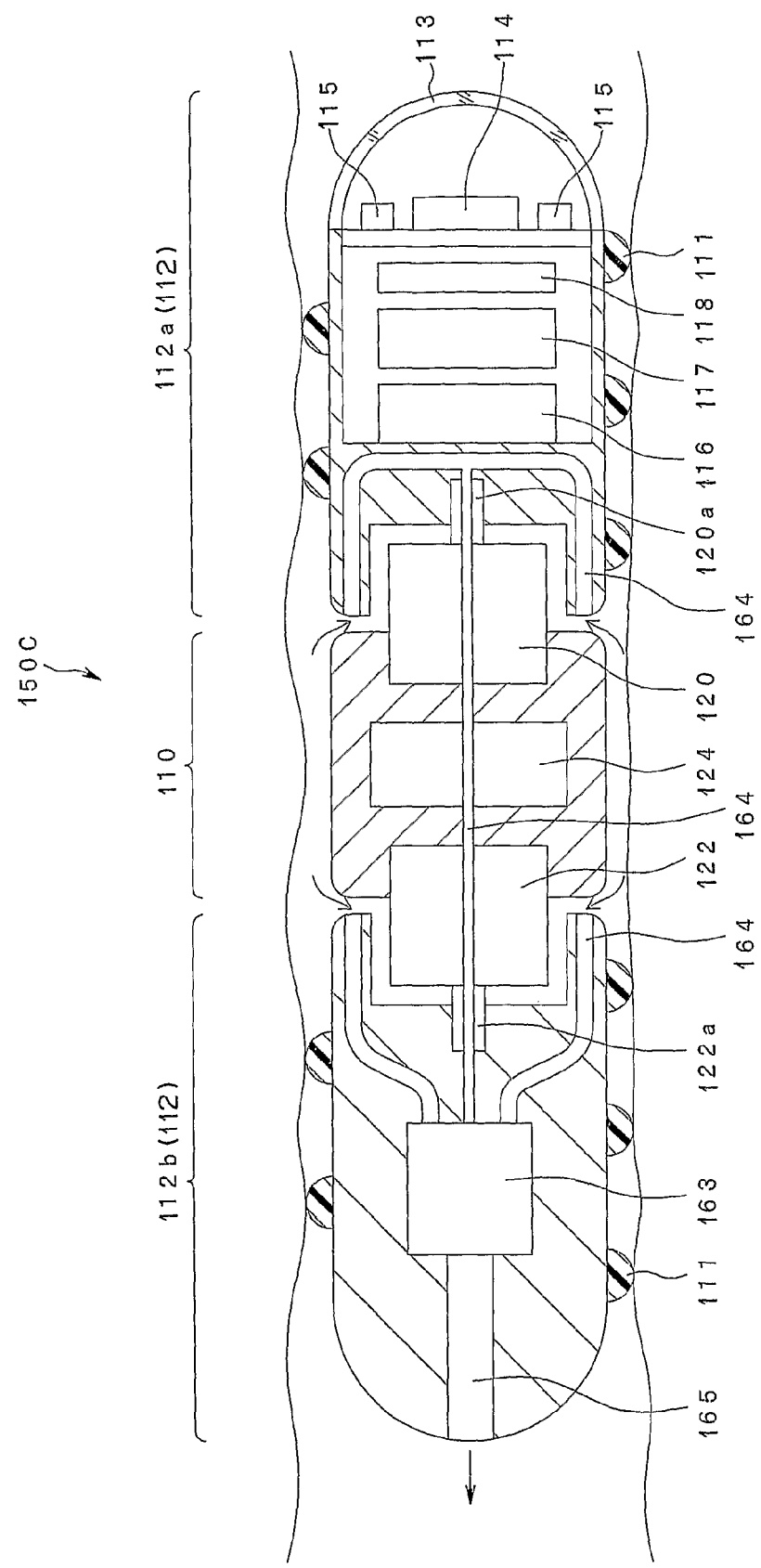
FIG. 47 is a sectional view which shows the internal configuration of a capsule including a suction mechanism for suction within the body cavity, which serves as helical-structure contact means.

FIG. 47 shows a capsule 150C having a function of assisting in maintaining the state in which the helical rotation propelling unit 112 is in contact with the inner wall of the intestinal tract at all times by actions of a suction mechanism for applying suction to the inner wall of the body cavity.

More specifically, the capsule 150C comprises: a suction device 163 for drawing fluid such as air, body fluid, and so forth within the intestinal tract; a suction channel 164 connected to the suction device 163 for drawing the fluid; and a discharging channel 165 for discharging the fluid thus drawn in.

The suction device 163 is provided to the rear-side helical rotation propelling unit 112*b*. Accordingly, with regard to the front-side helical rotation propelling unit 112*a*, the suction channel 164 is connected to the suction device 163 through the base 110.

The suction channel 164 is connected via the first motor 120 and the second motor 122.

Figure 48:
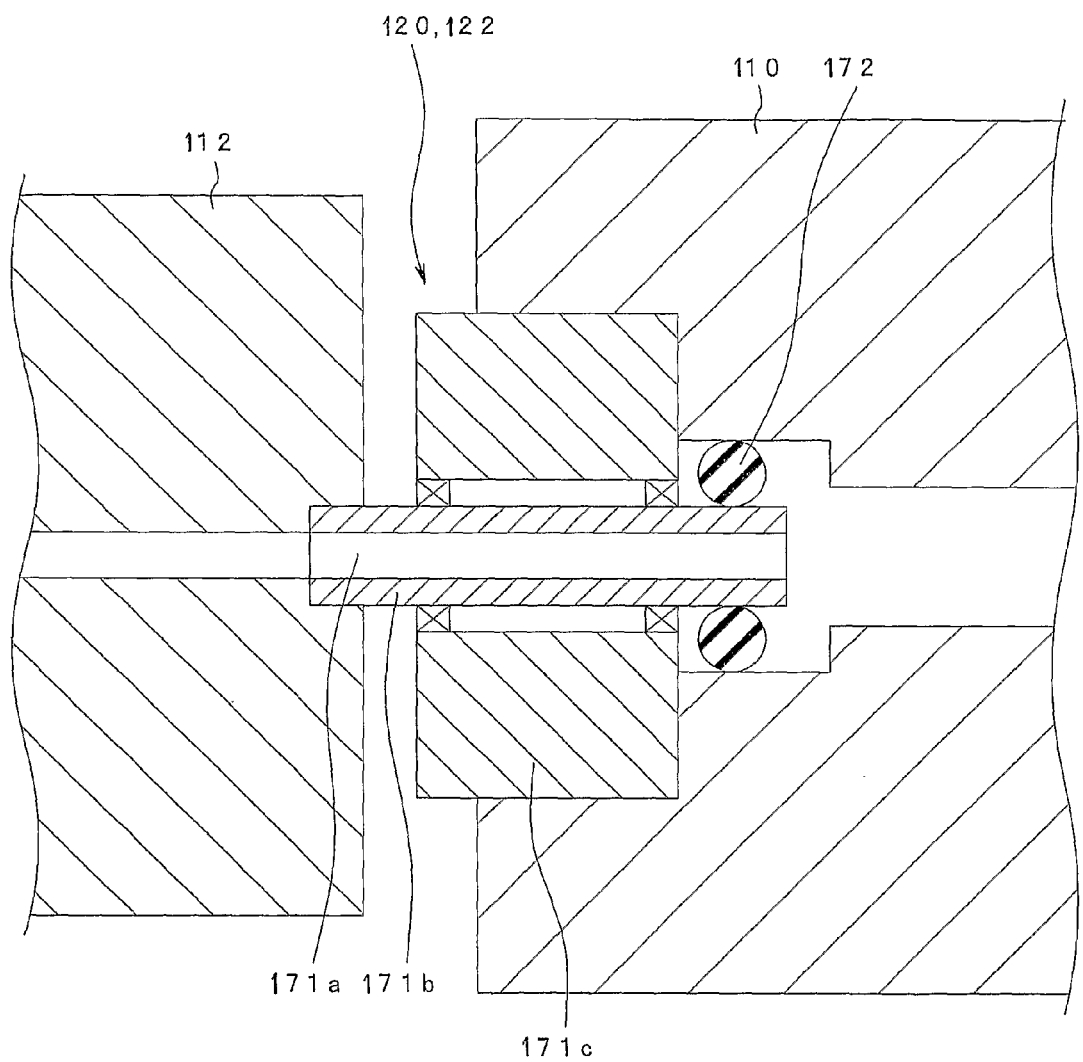
FIG. 48 is a principal component explanatory diagram which shows the first motor and the second motor shown in FIG. 47.

As shown in FIG. 48, with the first motor 120 and the second motor 122, a through channel 171*a* formed so as to pass through a rotary shaft 171, which is provided so as to pass through the inside of the motor, is sealed with an O-ring 172, thereby forming the suction channel 164. Note that each of the motor 120 and 122 comprises a rotor 171*b* and a stator 171*c*.

The capsule 150C having such a configuration has a function for drawing fluid such as air, body fluid, and so forth within the intestinal tract which is a lumen within the body cavity. This contracts the intestinal tract in the same way as with the aforementioned capsule 150B. This assists in maintaining the state in which the base 110 and the helical rotation propelling unit 112 are in contact with the inner wall of the intestinal tract at all times, thereby propelling the capsule 150C in a sure manner.

Also, the capsule may have a variable diameter mechanism for changing the diameter of the helical rotation propelling unit 112 by actions of a fluid supply mechanism provided thereto, which serves as the helical-structure contact means.

Figure 49:
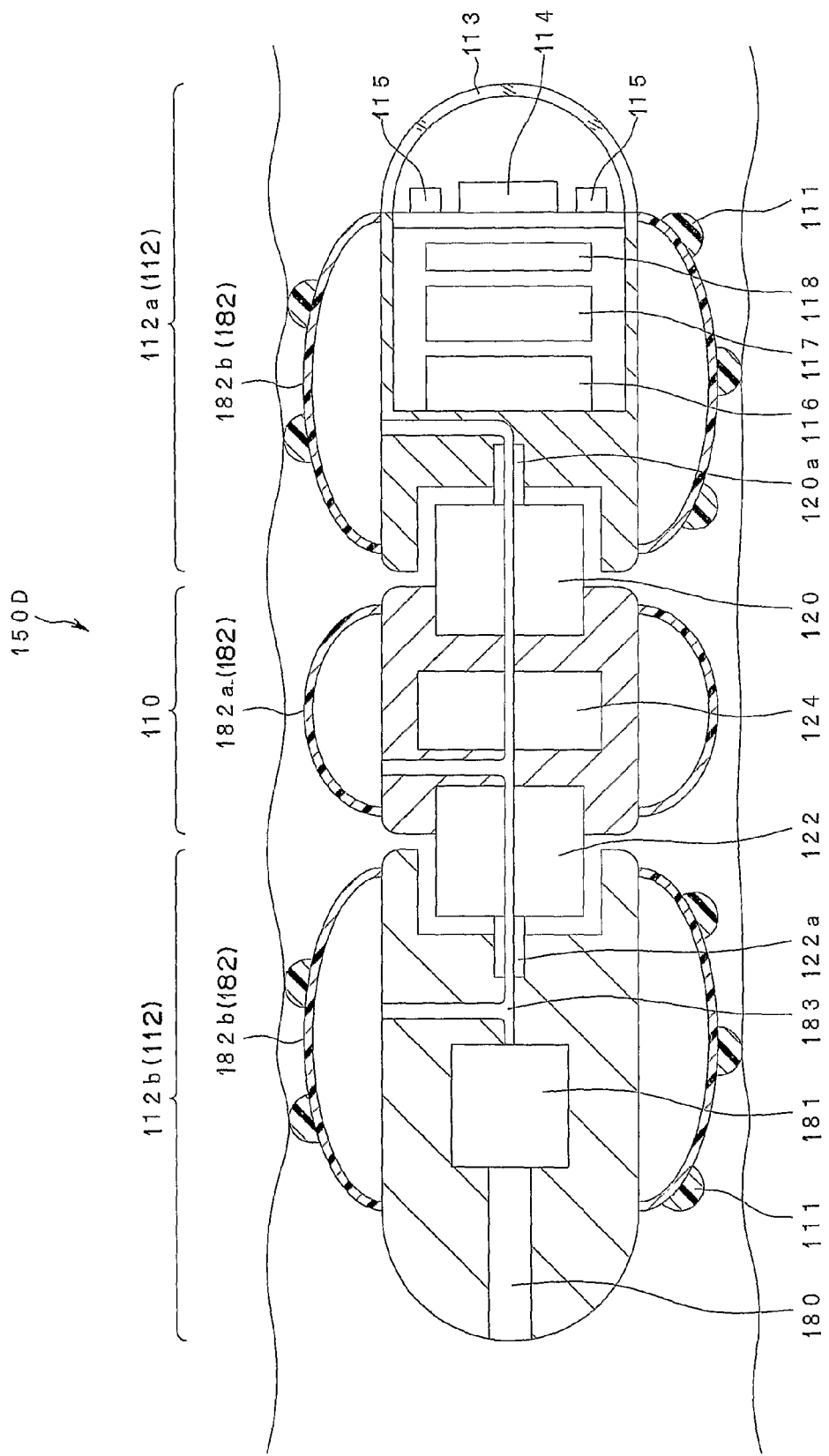
FIG. 49 is a sectional view which shows the internal configuration of a capsule including diameter-variable means which allows change in the diameter of the helical rotation propelling unit by actions of a fluid supply mechanism included therein, which serves as helical-structure contact means.

FIG. 49 shows a capsule 150D having a function for expanding the helical rotation propelling unit 112 and the base 110 by actions of the fluid supply mechanism. This assists in maintaining the state in which the helical rotation propelling unit 112 and the base 110 are in contact with the inner wall of the intestinal tract at all times.

More specifically, the capsule 150D comprises: a suction channel 180 for drawing air and the body fluids within the intestinal tract; a fluid supply device 181, connected to the suction channel 180, for supplying the fluid thus sucked; balloons 182 provided to the base 110 and the helical rotation propelling units 112; and a fluid supply cannel 183 for supplying fluid from the fluid supply device 181 to the balloons 182. That is to say, the balloons 182 serve as the diameter-variable means.

Note that a base-side balloon 182*a* provided to the base 110 has multiple grooves 125 formed on the outer face thereof in parallel with the longitudinal axis, which serves as anti-rotation means. On the other hand, helical-structure-side balloons 182*b* provided to the helical rotation propelling units 112 have the helical protrusions 111.

The fluid supply device 181 is provided to the rear-side helical rotation propelling unit 112*b*. Accordingly, the balloons 182 provided to the base 110 and the front-side helical rotation propelling unit 112*a* are connected to the fluid supply device 181 through the fluid supply channel 183. Here, a part of the fluid supply channel 183 is formed of the first motor 120 and the second motor 122 in the same way as with the capsule 150B described above.

The capsule 150D having such a configuration has a function of drawing fluid such as air, body fluids, and so forth within the intestinal tract and supplying the fluid thus sucked to the balloons 182 (base-side balloon 182*a* and helical-structure-side balloon 182*b*) so as to expand the balloons 182. This assists in maintaining the state in which the base 110 and the helical rotation propelling units 112 are in contact with the inner wall of the intestinal tract at all times.

Also, the capsule may have a balloon forming helical protrusions, as well as serving as diameter-variable means.

Figure 50:
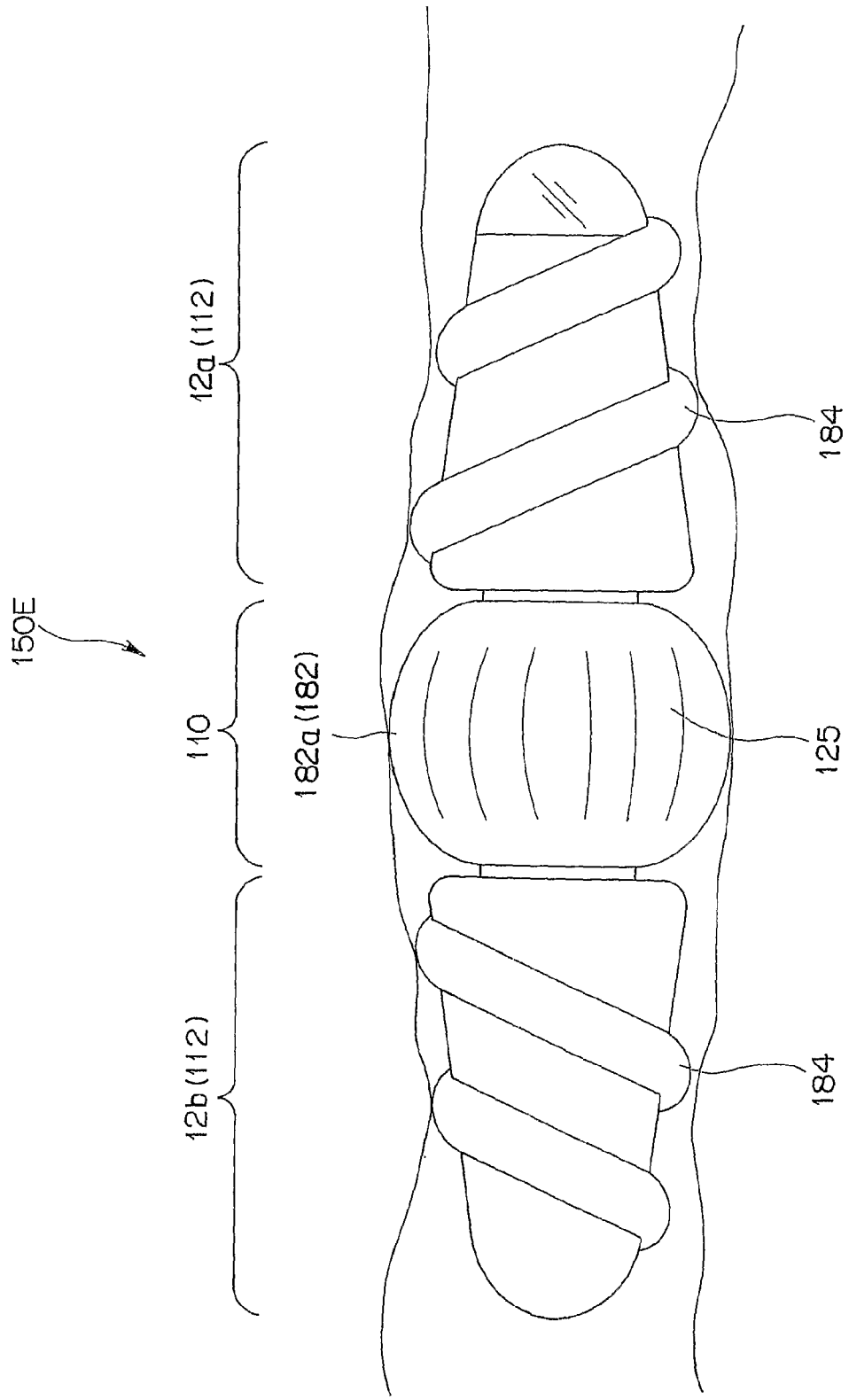
FIG. 50 is an external view of a capsule including helical protrusions formed of balloons, which serves as diameter-variable means.

FIG. 50 shows a capsule 150E having helical-structure balloons 184 each of which forms a helical protrusion. That is to say, the helical-structure balloons 184 serve as diameter-variable means. Note that the capsule 150E has the fluid supply channel 183 connected to the helical-structure balloons 184, which is not shown in the drawing.

The capsule 150E having such a configuration has a function of drawing fluid such as air, body fluid, and so forth within the intestinal tract and supplying the fluid thus sucked to the balloon 182 provided to the base 110 and the helical-structure balloons 184 so as to expand these balloons. This assists in maintaining the state in which the base 110 and the helical rotation propelling units 112 are in contact with the inner wall of the intestinal tract at all times, thereby enabling the capsule 150E to be propelled in a sure manner.

Also, the base 110 may have the anti-rotation means having configurations as shown in FIGS. 51 through 54.

Figure 51:
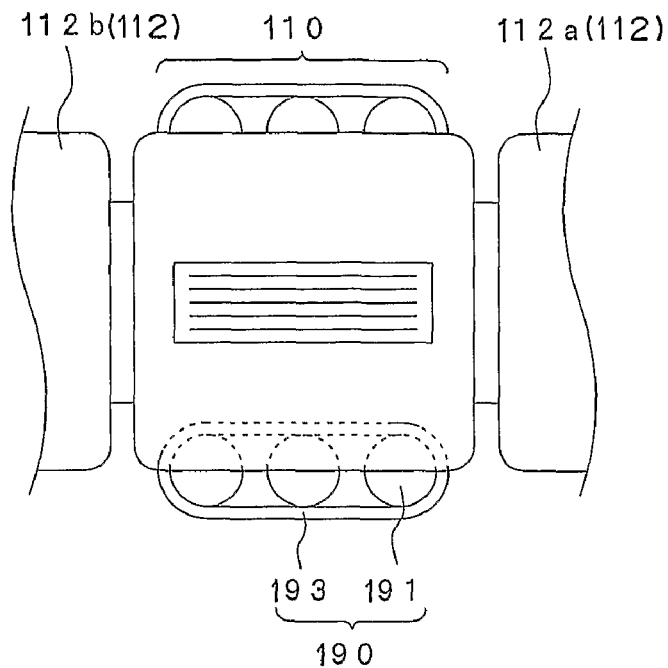
FIG. 51 is an explanatory diagram which shows the base including caterpillar tracks serving as rotation preventing means.

FIG. 51 shows the base 110 including caterpillar tracks 190 as the anti-rotation means. Each caterpillar track 190 comprises multiple roller tires 191 (the drawing shows three tires) each of which is rotatably mounted with an unshown axis as the center of rotation, and a belt 192 is placed on the roller tires 191. Note that the base 110 includes multiple caterpillar tracks 190 (four caterpillar tracks mounted symmetrically in the vertical direction and the direction perpendicular to the drawing).

Figure 52:
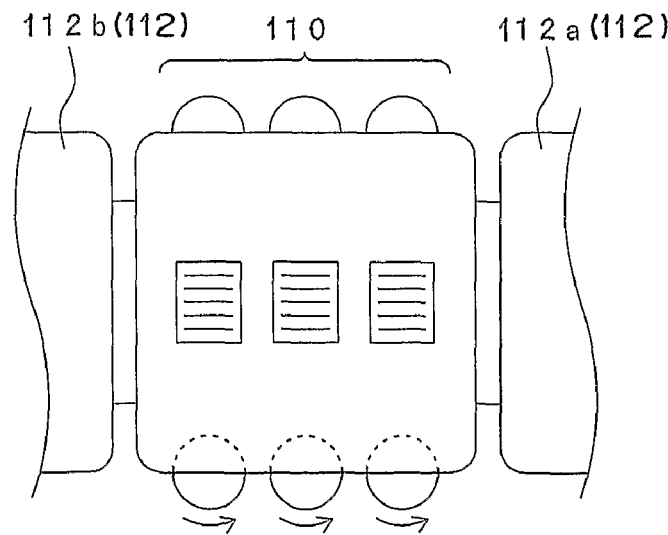
FIG. 52 is an explanatory diagram which shows the base including roller tires serving as rotation preventing means.
Figure 53:
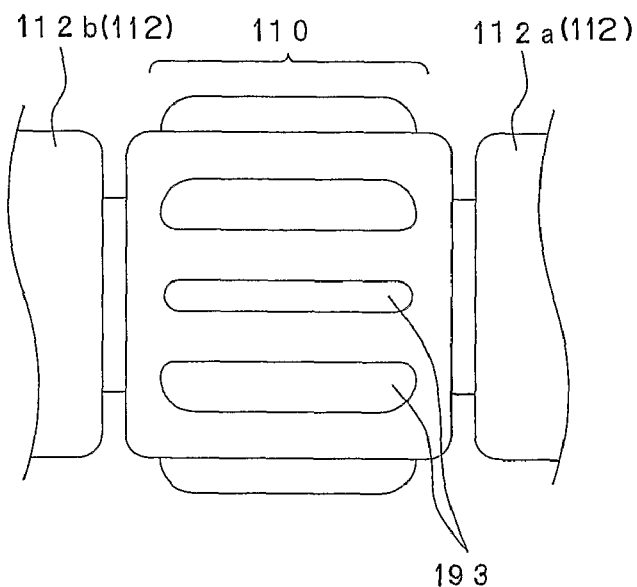
FIG. 53 is an explanatory diagram which shows the base including fin-shaped protrusions serving as rotation preventing means.
Figure 54:
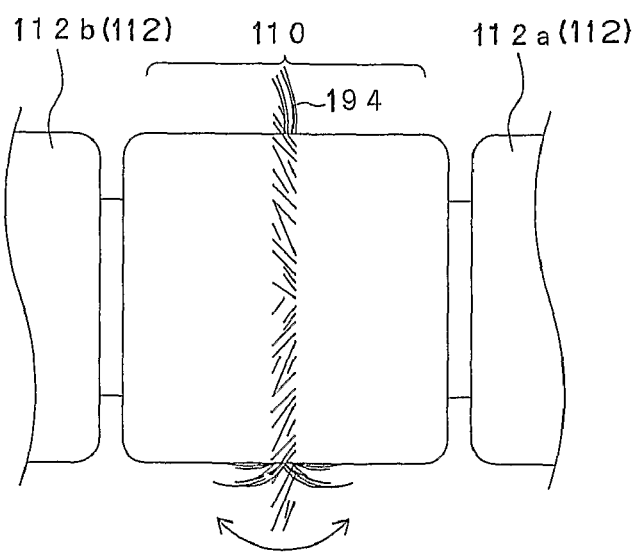
FIG. 54 is an explanatory diagram which shows the base including a brush serving as rotation preventing means.

FIG. 52 shows the base 110 including multiple roller tires 191 as the anti-rotation means. On the other hand, FIG. 53 shows the base 110 including multiple fin-shaped protrusions 193 as the anti-rotation means. On the other hand, FIG. 54 shows the base 110 including a brush 194 around the outer face as the anti-rotation means.

With the capsule 150, the anti-rotation means having such configurations as shown in FIGS. 51 through 54 prevent rotation of the base 110 with respect to the body cavity without affecting propelling of the helical rotation propelling units 112.

Embodiment 9

Description will be made regarding an embodiment 9 according to the present invention with reference to FIGS. 55 and 56.

Description has been made in the embodiments 7 and 8 regarding an arrangement in which the image pickup device 114 is provided to the helical rotation propelling unit 112, and accordingly, rotating capsule-captured images are obtained. The embodiment 9 has a configuration which allows capturing of images without rotation. The other components are generally the same as those of the aforementioned embodiments 7 and 8. Accordingly, the same components are denoted by the same reference numerals, and description thereof will be omitted.

Figure 55:
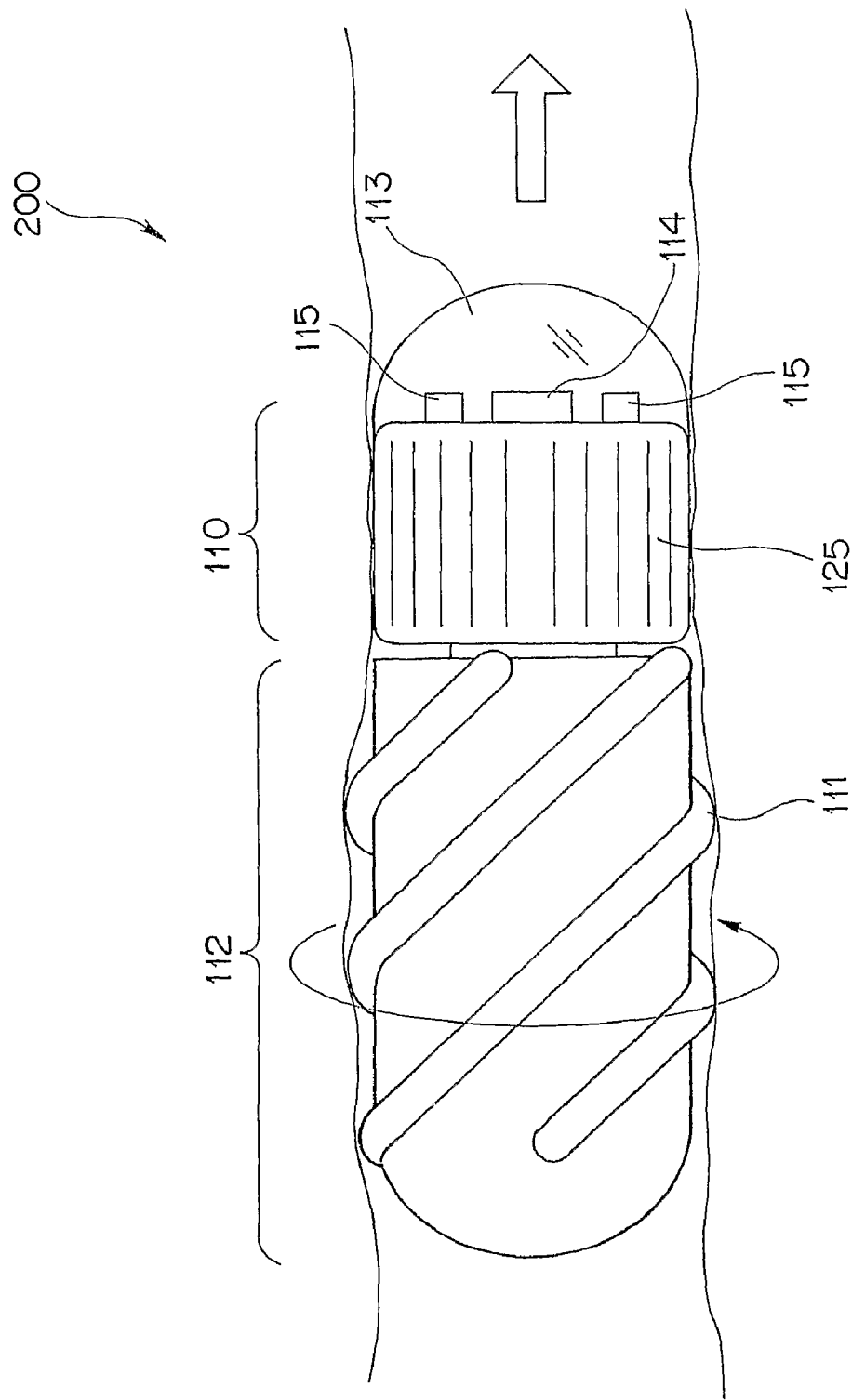
FIG. 55 is an external view of a capsule according to an embodiment 9.

FIG. 55 shows a capsule 200 according to the embodiment 9 having a configuration in which the image pickup device 114 is provided to the base 110, thereby obtaining capsule-captured images without rotation.

More specifically, with the capsule 200, a transparent member 113 is formed in the shape of a hemisphere on the end (which will be referred to as "front end") of the base 110. Furthermore, the image pickup device 114 is provided around the center of the front end of the base 110 so as to face the transparent member 113. Furthermore, the four illumination devices 115 such as LEDs or the like are provided around the image pickup device 114, for example.

Note that the helical rotation propelling unit 112 includes the first battery 116, the image transmission unit 117, and the control circuit 118 in the same way as with the aforementioned embodiment 7, which are not shown in the drawing. Furthermore, the image pickup device 114 and the illumination devices 115 are electrically connected to these components through an unshown slip ring, thereby allowing the image pickup device 114 and the illumination devices 115 to be driven. The other components are the same as those of the aforementioned embodiment 7, and accordingly, description thereof will be omitted.

The capsule 200 having such a simple configuration provides capsule-captured images without rotation, and accordingly, without the need for image processing.

Also, the capsule may include the helical rotation propelling unit 112 formed in the shape of a sheath with the image pickup device 114 provided to the base 110, thereby obtaining capsule-captured images without rotation.

Figure 56:
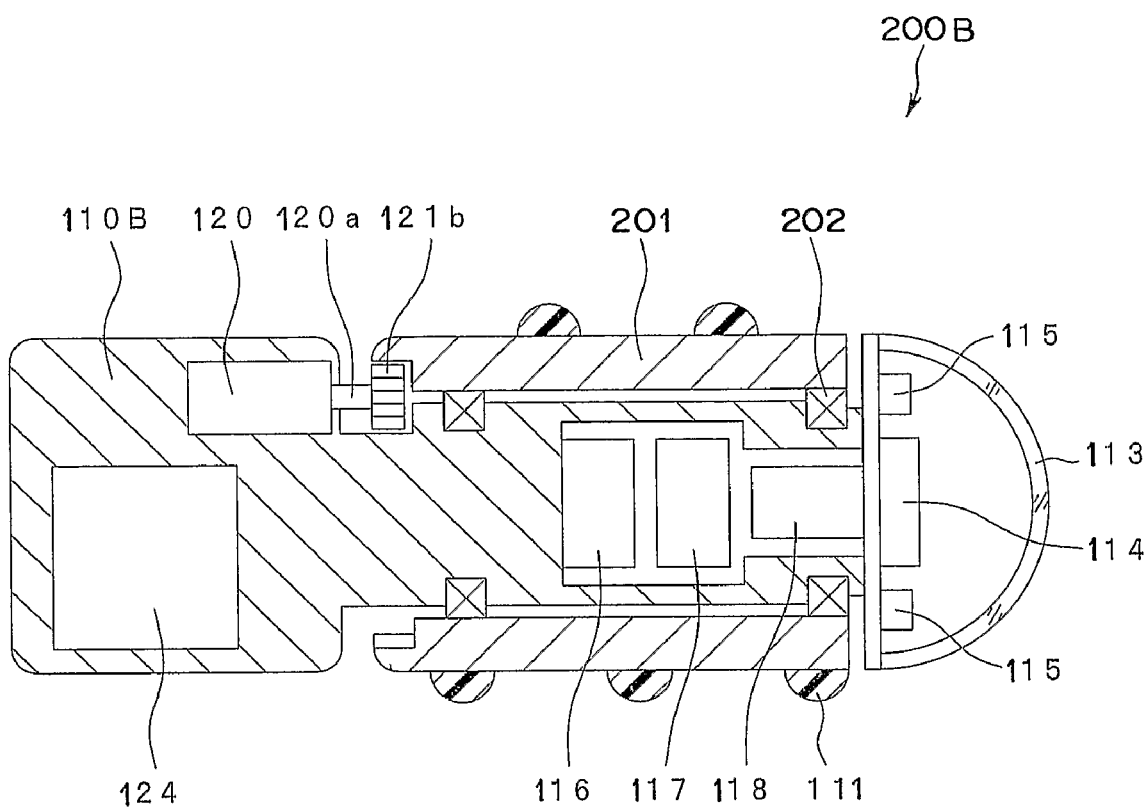
FIG. 56 is a sectional view which shows the internal configuration of a capsule having a configuration in which the helical rotation propelling unit formed in the shape of a sheath is fitted to the base including the image pickup device.

FIG. 56 shows a capsule 200B having a configuration in which a sheath-shaped helical rotation propelling 201 unit is provided so as to surround the base 110B.

The sheath-shaped helical rotation propelling unit 201 rotatably mounted to the base 110B through a bearing 202. Furthermore, the base 110B includes the first motor 120 with a pinion 121*b* provided to the motor shaft 120*a*, meshing with the sheath-shaped helical rotation propelling unit 201.

This allows the sheath-shaped helical rotation propelling unit 201, provided so as to surround the base 110B, to be rotated by driving the first motor 120. That is to say, the sheath-shaped helical rotation propelling unit 201 serves as a sheath-shaped rotor.

Furthermore, the transparent member 113 is formed in the shape of a hemisphere on the end (which will be referred to as "front end") of the base 110B. Furthermore, the image pickup device 114 is provided around the center of the front end of the base 110B so as to face the transparent member 113. Furthermore, the four illumination devices 115 such as LEDs or the like are provided around the image pickup device 114, for example. On the other hand, the first battery 116, the image transmission unit 117, and the control circuit 118 are provided on the rear side of the image pickup device 114 and the illumination devices 115.

The capsule 200B having such a configuration provides capsule-captured images without rotation, thereby providing the same advantages as with the capsule 200 described above.

Embodiment 10

Description will be made regarding en embodiment 10 according to the present invention with reference to FIGS. 57 through 59.

Description has been made in the aforementioned embodiments 7 through 9 regarding the anti-rotation means having a structure in which the multiple grooves 125 are formed on the outer face of the base in parallel with the longitudinal axis. On the other hand, the embodiment 10 includes the anti-rotation means having a structure in which the helical protrusion 111 is provided on the outer face of the base. The other components are generally the same as those of the aforementioned embodiments 7 and 8. Accordingly, the same components are denoted by the same reference numerals, and description thereof will be omitted.

Figure 57:
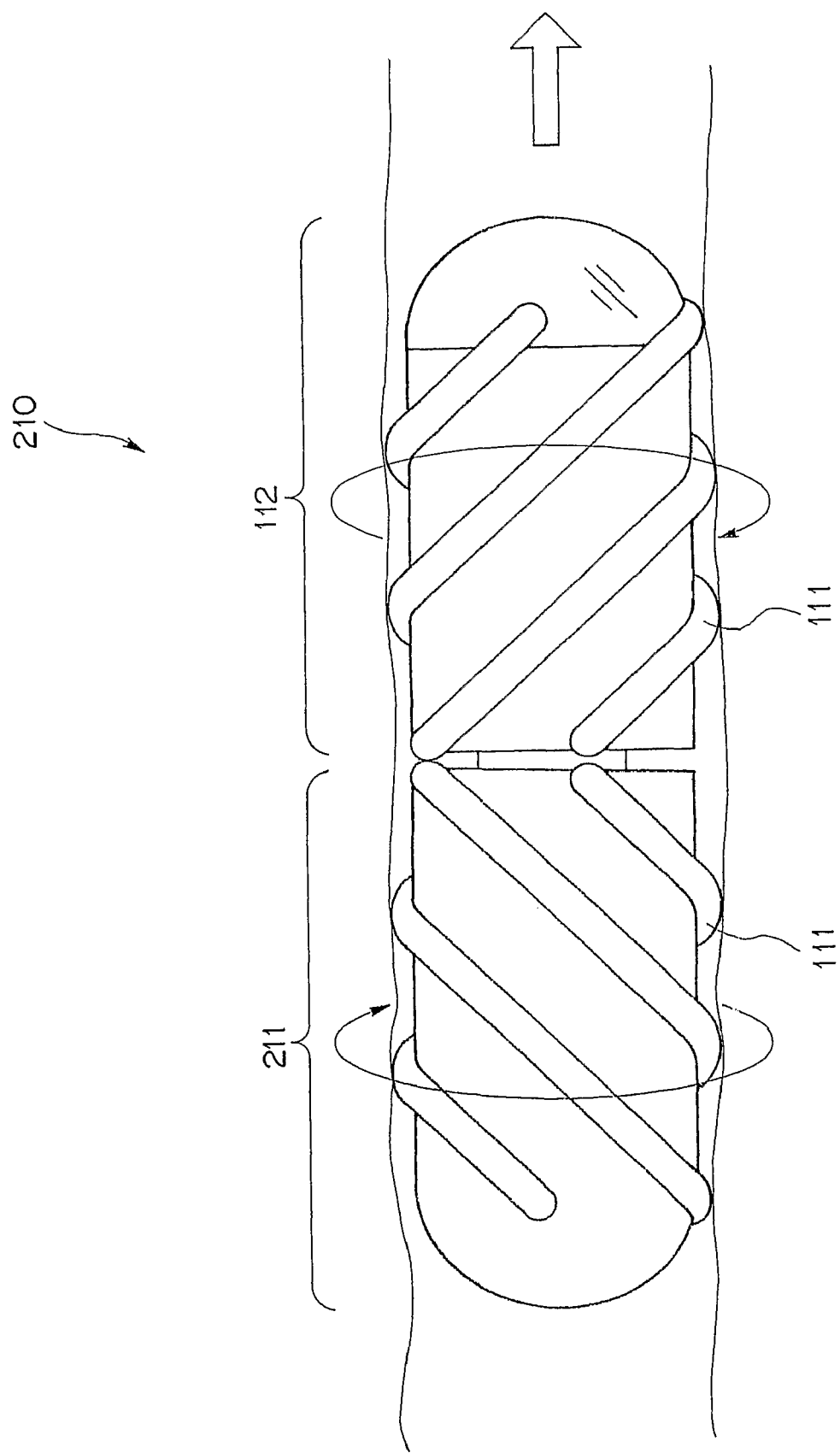
FIG. 57 is an external view of a capsule according to an embodiment 10.
Figure 58:
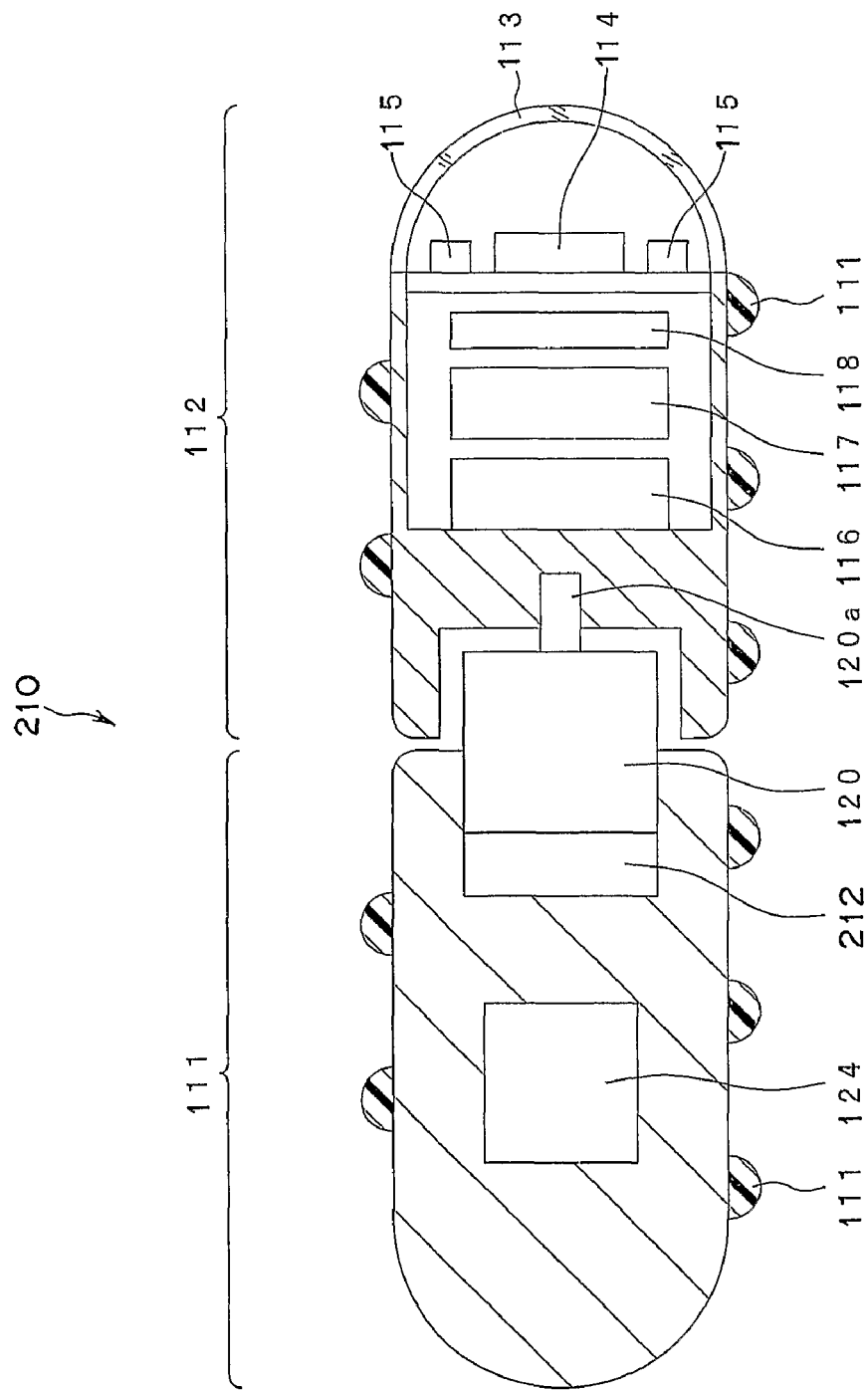
FIG. 58 is a sectional view which shows the internal configuration of the capsule shown in FIG. 57.

FIGS. 57 and 58 show a capsule 210 according to the embodiment 10 having a configuration in which the base 211 including the first motor 120 for rotating the helical rotation propelling unit 112 has the helical protrusion 111 formed on the outer face thereof.

The base 211 having such a structure rotates in the reverse rotating direction of that of the helical rotation propelling unit 112 due to the inertial force due to rotation of the helical rotation propelling unit 112 driven by the first motor 120.

With the capsule 210 having such a configuration, the base 211 rotates in the reverse rotating direction of the helical rotation propelling unit 112, thereby preventing all the parts of the capsule 210 from rotating with respect to the inner wall of the body cavity.

Furthermore, the capsule 210 includes an angular speed sensor 212 provided to the first motor 120. The angular speed sensor 212 has a function of detecting change in the rotating speed of the helical rotation propelling unit 112 due to rotation thereof without load. This enables adjustment of the rotational speed of the helical rotation propelling unit 112 to the optimum value, thereby realizing efficient propelling of the capsule 210.

Note that the capsule 210 includes: the vibration means (swinging means) including the second motor 122 having the eccentric rotor 123 in the same way as with the capsule 102 described in the embodiment 7, or including the SMA coil 128 in the same way as with the capsule 102C; or the helical-structure contact means such as the means for applying electric stimulus so as to contract the intestinal tract in the same way as with the capsule 150B, and so forth, which are not shown in the drawings. This restores the situation in which the helical rotation propelling unit 112 is in contact with the inner wall of the body cavity, thereby allowing capsule 210 to be propelled.

Also, the capsule may include the helical-structure contact means having a structure in which the base and the helical rotation propelling unit are provided with one longitudinal axis bending with respect to the other.

Figure 59:
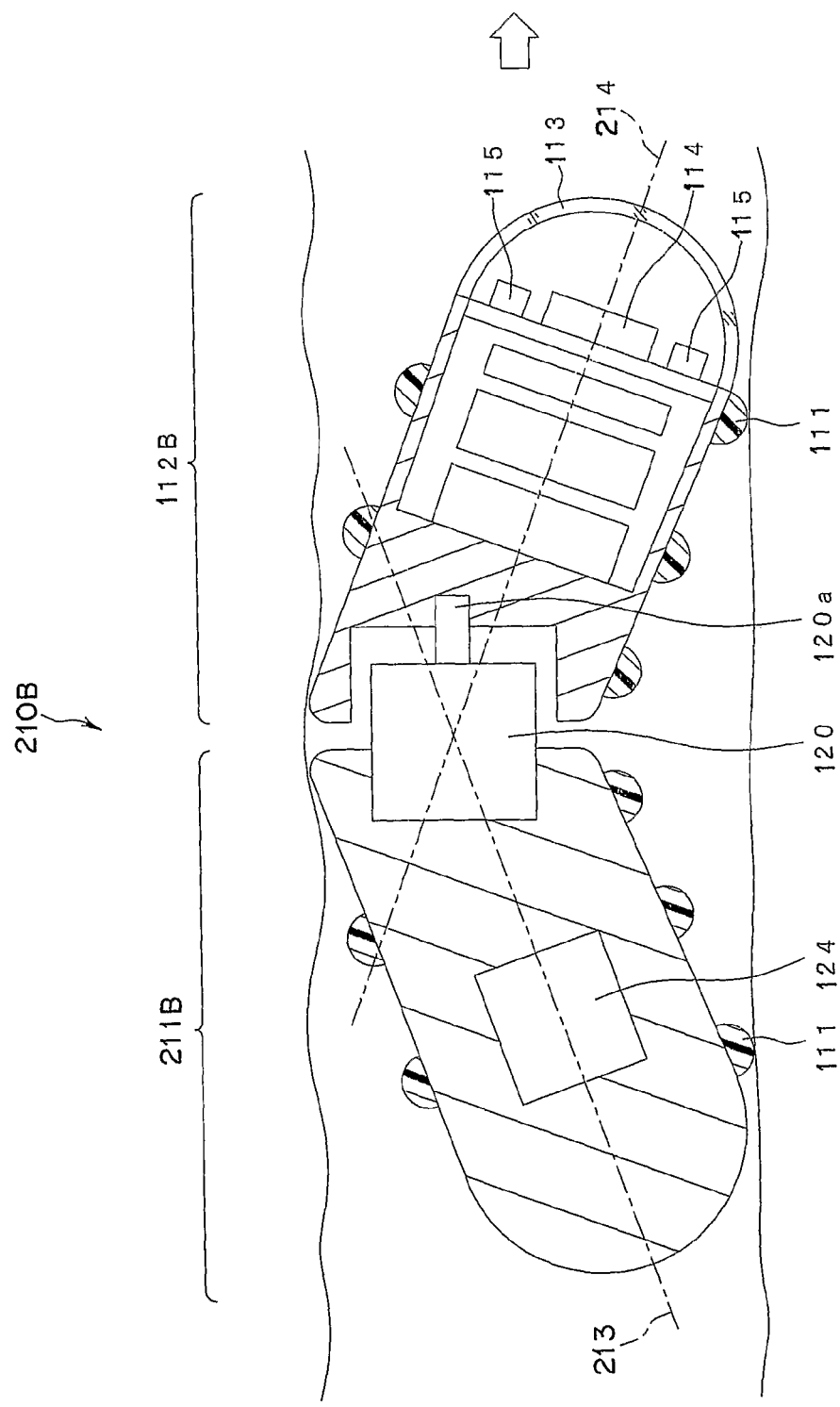
FIG. 59 is a sectional view which shows the internal configuration of a capsule having a structure in which the base and the helical rotation propelling unit are provided with one longitudinal axis bending with respect to the other.

FIG. 59 shows a capsule 210B having a configuration which maintains the state in which a base 211B having a longitudinal axis 213 and a helical rotation propelling unit 112B having a longitudinal axis 214 are positioned with one longitudinal axis bending with respect to the other.

More specifically, the capsule 210B includes the base 211B having the longitudinal axis 213 and the helical rotation propelling unit 112B having the longitudinal axis 214, which are connected by the first motor 120, with the axes 213 and 214 not being parallel with each other (with the axes 213 and 214 crossing each other).

The capsule 210B having such a configuration allows rotation thereof with the longitudinal axis 213 of the base 211B bending with respect to the longitudinal axis 214 of the helical rotation propelling unit 112B, thereby maintaining the suitable contact state with respect to the inner wall of the body cavity.

Embodiment 11

Description will be made regarding an embodiment 11 with reference to FIGS. 60 through 63.

While description has been made in the aforementioned embodiment 8 regarding an arrangement in which the base 110 maintains the shape thereof. With the embodiment 11, the base includes a joint which allows the base to be bent. The other components are generally the same as those of the aforementioned embodiment 8. Accordingly, the same components are denoted by the same reference numerals, and description thereof will be omitted.

Figure 60:
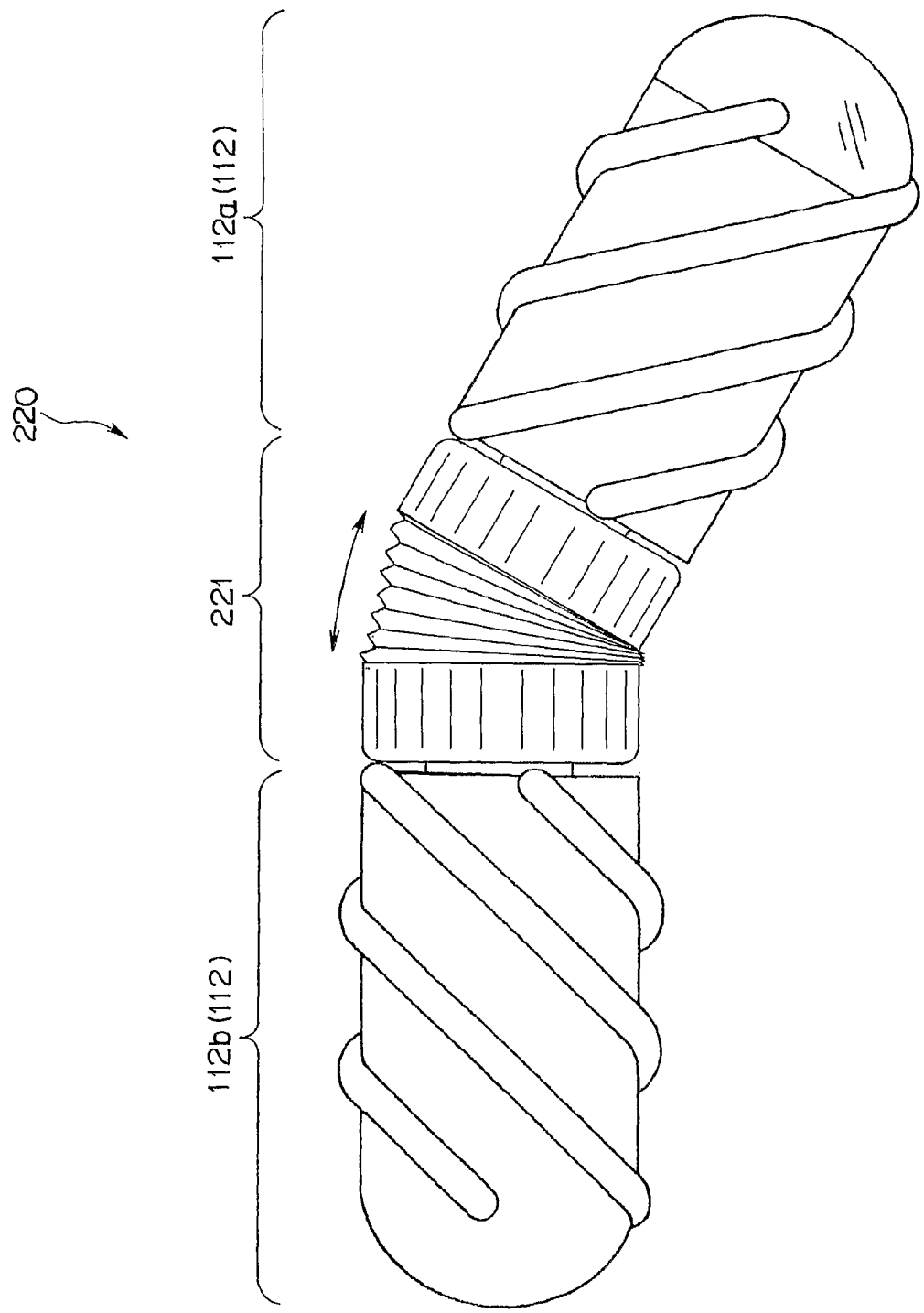
FIG. 60 is an external view of a capsule according to an embodiment 11.
Figure 61:
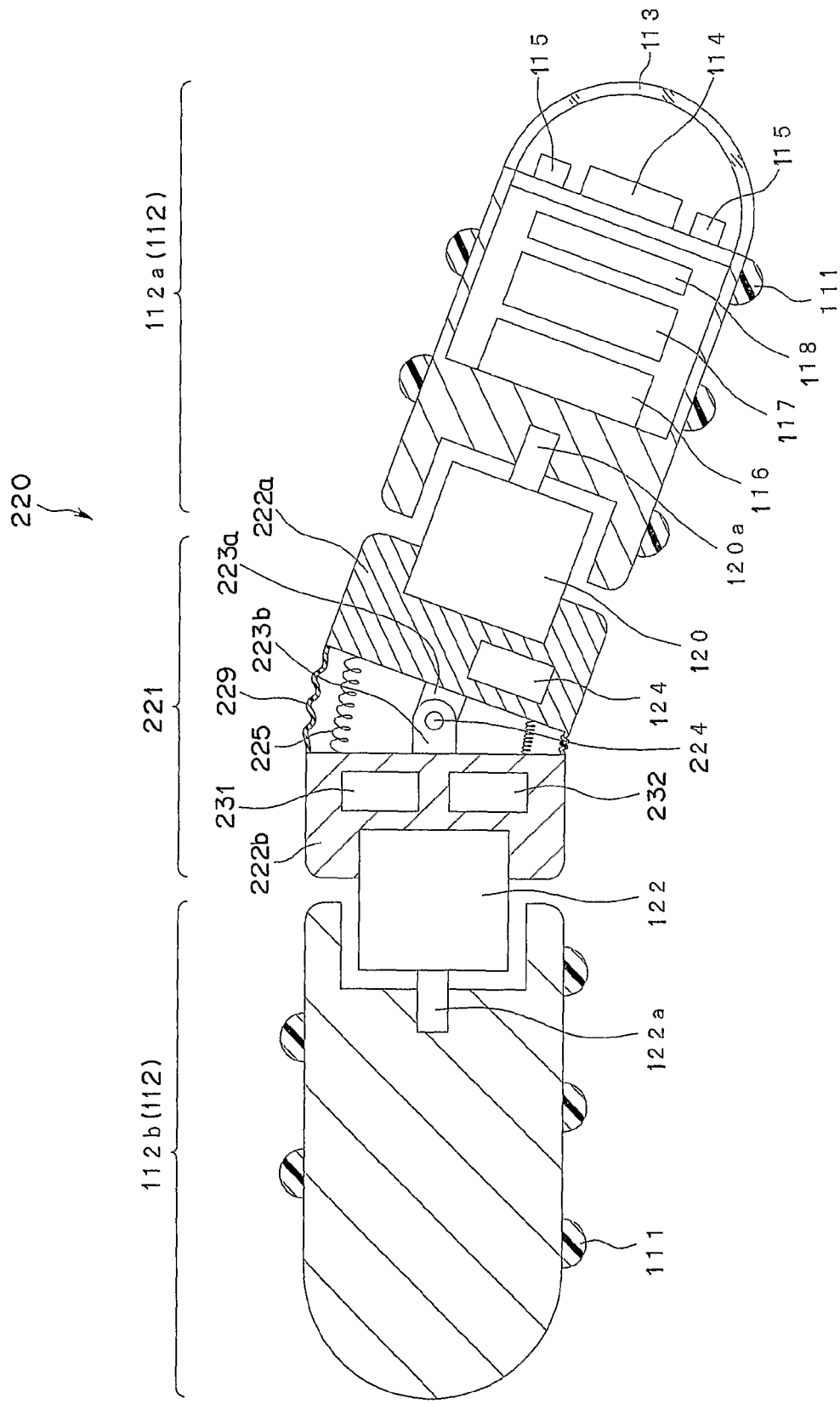
FIG. 61 is a sectional view which shows the internal configuration of the capsule shown in FIG. 60.

FIGS. 60 and 61 show a capsule 220 according to the embodiment 11 including a pair of the aforementioned helical rotation propelling units 112 with the base 221 introduced therebetween.

More specifically, the aforementioned capsule 220 comprises a base 221, and the front-side helical rotation propelling unit 112a and the rear-side helical rotation propelling unit 112b having a function of relative rotation thereof with respect to the base 221 by driving the first motor 120 and the second motor 122 mounted to the base 221. The front-side helical rotation propelling unit 112a and the rear-side helical rotation propelling unit 112b have the aforementioned helical protrusions 111 formed on the outer face thereof with the spiral directions different from each other.

The base 221 includes a front-side joint 222a and a rear-side joint 222b. These joints 222a and 222b are connected with each other by connecting the shaft 223a of the joint 222a and the shaft 223b of the joint 222b through a ball joint 224. Furthermore, these joints are connected with each other through four SMA coils 225 which are provided around the shafts 223a and 223b and which serve as joint-bending means, thereby allowing bending motion of these joints. Furthermore, with the base 221, the space between the front-side joint 222a and the rear-side joint 222b is covered with an accordion folded cover 229.

Also, an unshown flexible shaft may be employed in the base 221, instead of the aforementioned ball joint 224.

The first motor 120 is provided to the front-side joint 222a for rotating the front-side helical rotation propelling unit 112a. Furthermore, the second battery 124 is provided for supplying electric power for driving the first motor 120.

On the other hand, with the rear-side joint 222b, the second motor 122 is provided for rotating the rear-side helical rotation propelling unit 112b, as well as an SMA driving circuit 231 for applying electricity to the SMA coils 225. Furthermore, a third battery 232 is provided for supplying electric power for driving the second motor 122 and the SMA driving circuit 231.

The aforementioned capsule 220 having such a configuration has a function of extension/contraction of the four SMA coils 225 by applying electricity from the SMA driving circuit 231, thereby enabling the base 221 to be bent in a desired direction. Note that the drawing shows the capsule 220 in the state in which the base 221 is bent downward with the upper SMA coils being extended and with the lower SMA coils being contracted, thereby bending the front-side helical rotation propelling unit 112a downward.

That is to say, the joints 222a and 222b, and the SMA coils 225, which are joint-bending means, form propelling-direction changing means.

Figure 62:
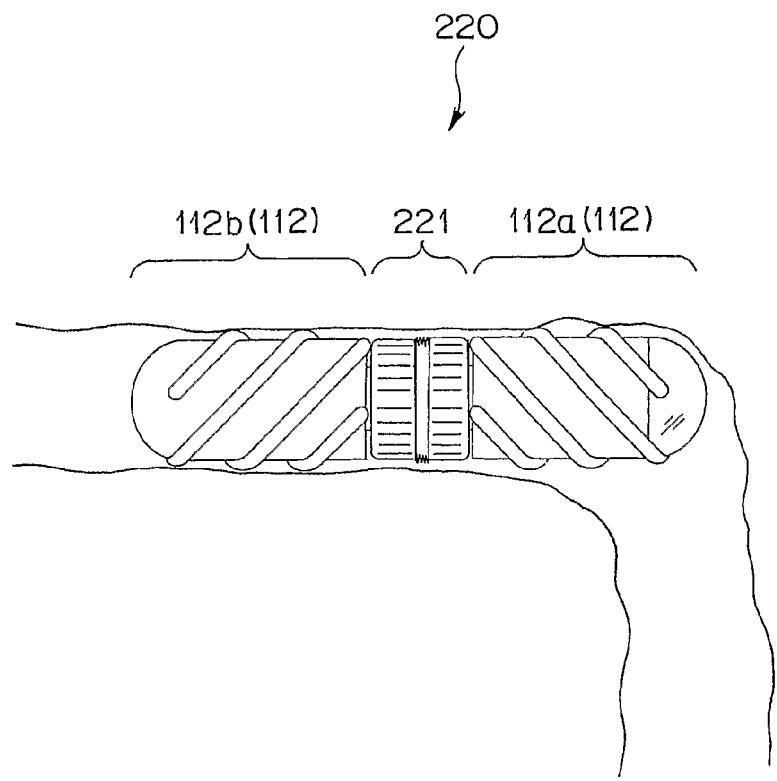
FIG. 62 is an explanatory diagram which shows the capsule shown in FIG. 60 immediately prior to passing through a curve of the lumen within the body cavity.
Figure 63:
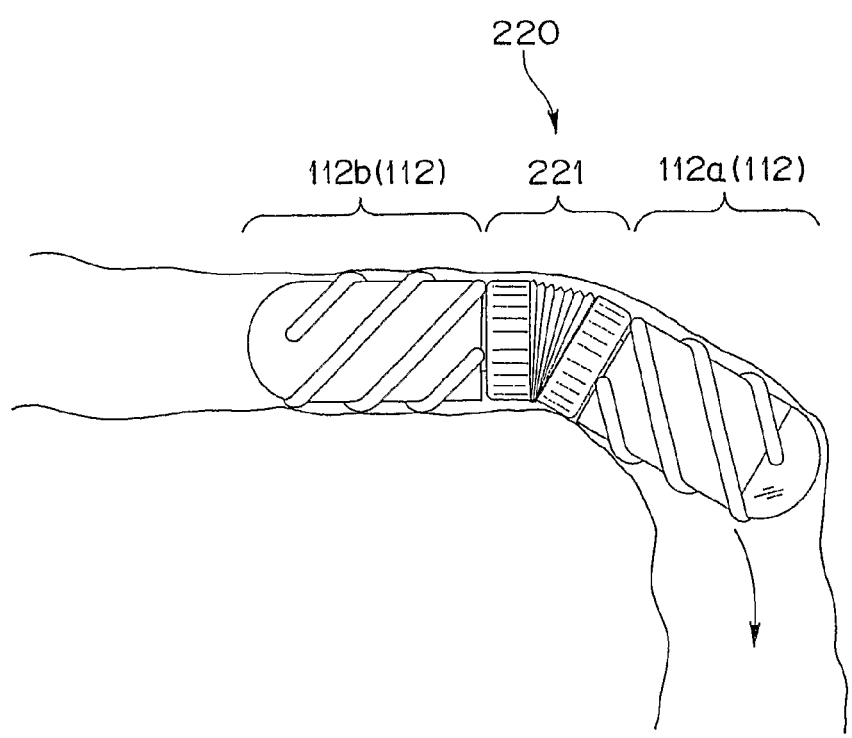
FIG. 63 is an explanatory diagram which shows the capsule passing through the curve of the lumen within the body cavity following the situation shown in FIG. 62.

Thus, the capsule 220 has a function for handling a situation as shown in FIG. 62, in which the capsule 220 has reached a curve within the body cavity. In this case, the base 221 is bent as shown in FIG. 63, thereby changing the propelling direction of the front-side helical rotation propelling unit 111a downward. This facilities the passage thereof through such a curve.

Embodiment 12

Next, description will be made regarding an embodiment 12 according to the present invention with reference to FIGS. 64 and 65.

The difference between the capsule medical system according to the present embodiment and the capsule medical system according to the embodiment 8 is that a capsule 150F according to the present embodiment includes multiple image pickup devices. Note that the same components as those of the embodiment 8 are denoted by the same reference numerals, and description thereof will be omitted.

Figure 64:
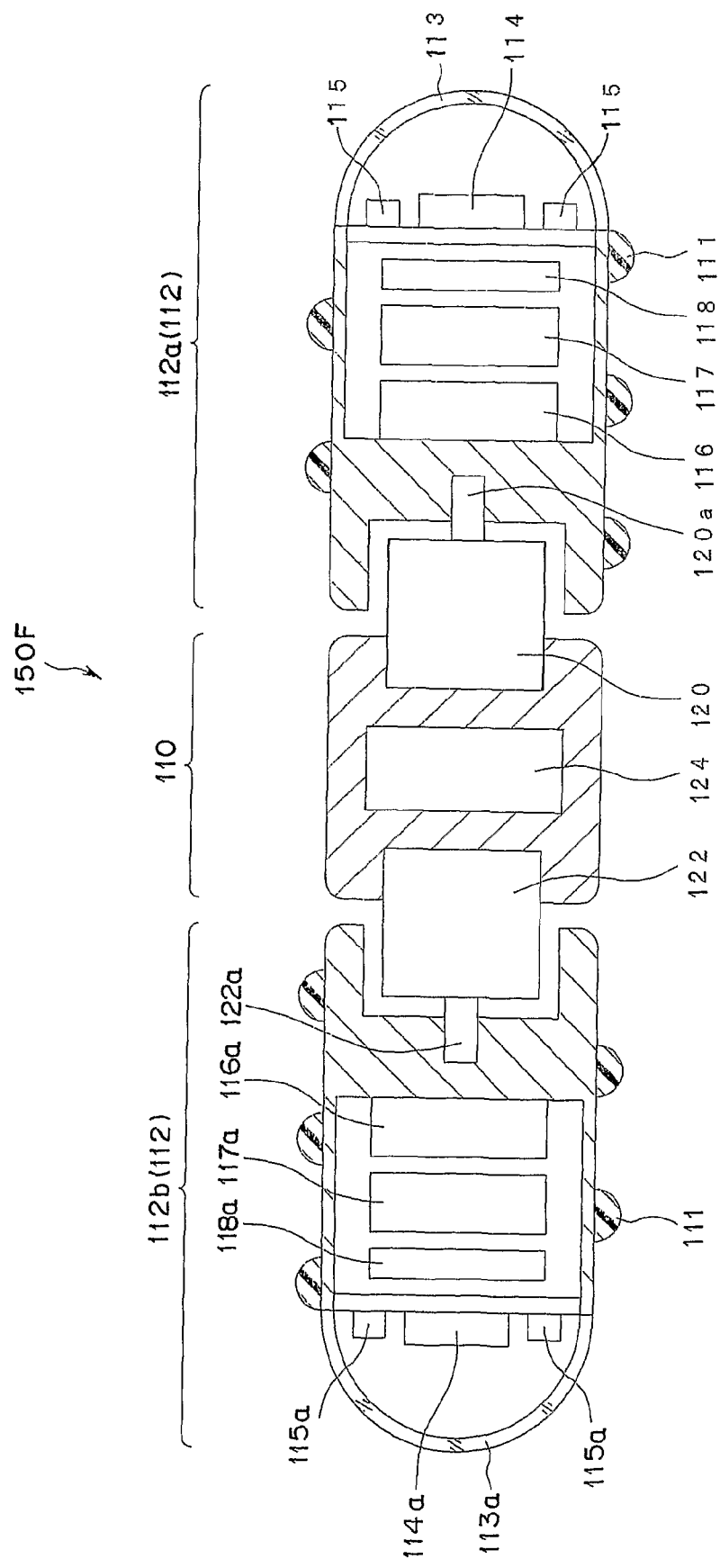
FIG. 64 is a sectional view which shows an internal configuration of a capsule according to an embodiment 12.

FIG. 64 shows the capsule 150F having generally the same configuration as that of the capsule 150 shown in FIG. 45, except for the rear-side helical rotation propelling unit 112b also having a configuration in which a transparent member 113a is formed in the shape of a hemisphere, an image pickup device 114a is provided around the center thereof so as to face the transparent member 113a, and illumination devices 115a such as LEDs are provided therearound.

That is to say, the capsule 150F includes the image pickup device 114a and the illumination devices 115a provided to the rear-side helical rotation propelling unit 112b, as well as the image pickup device 114 and the illumination devices 115 provided to the front-side helical rotation propelling unit 112a.

Furthermore, a battery 116a, an image transmission unit 117a, and a control circuit 118a are provided on the front side of the image pickup device 114a and the illumination devices 115a (on the right side in FIG. 64). This enables the capsule 150F to be propelled while capturing images both ahead and behind thereof.

Thus, the capsule 150F has the advantage of providing a field of view behind thereof as well as ahead thereof.

Furthermore, with the present embodiment, the image rotation processing is performed in the same way as with the embodiments 7 through 11 described above. This enables the images to be displayed without concern of the operator for rotation of the images due to the rotation of the front-side helical rotation propelling unit 112a and the rear-side helical rotation propelling unit 112b.

Description has been made in the embodiment 6 regarding an arrangement in which the image captured by the front-side image pickup device and the image captured by the rear-side image pickup device are rotated in opposite rotating directions. With the present embodiment, the images captured by the image pickup devices 114 and 114a are rotated based upon the rotating angles of the motors 120 and 122.

For example, let us say that the front-side helical rotation propelling unit 112a and the rear-side helical rotation propelling unit 112b are rotated with respect to the base 110 as shown in FIG. 65. In this case, the images captured by the image pickup devices 114 and 114a are rotated in the same direction so as to display the images without concern for rotation of the image. Furthermore, with the present embodiment, the rotating angle may be detected for each helical rotation propelling unit in order to perform proper rotation correction for displaying the images, thereby handling a situation in which the rotating angles of the front-side helical rotation propelling unit 112a and the rear-side helical rotation propelling unit 112b are different from each other.

It should be understood that the present invention is not intended to be limited to the embodiments described above; rather, various changes and modifications may be made without departing from the essence of the present invention.

INDUSTRIAL APPLICABILITY

A medical device such as a capsule endoscope including an image pickup device and so forth, which is to be inserted into the body cavity and which has a function of generating the propelling force by rotation thereof, provides desired images captured within the body cavity in a short period of time. Furthermore, the image captured by the image pickup device is subjected to rotation processing based upon a detected signal with respect to the point in time of image capturing performed by the image pickup device, thereby enabling high-precision rotation correction. This provides images displayed on a display device which correspond to predetermined rotating angle, thereby facilitating observation.

The invention claimed is:

1. A medical system comprising:
a medical device to be inserted into a body cavity;
a rotating device for the medical device for rotating the medical device around an insertion axis;
an image pickup device provided to the medical device;
an image capturing timing detection device for detecting an image capturing timing signal with respect to image capturing timing performed by the image pickup device;
a rotating angle acquisition device for acquiring rotating angle information of the rotating device for the medical device with respect to the image capturing timing in response to the output of the image capturing timing detection device; and
an image acquisition device for performing rotation processing so as to rotate an image captured by the image pickup device based upon the rotating angle information acquired by the rotating angle acquisition device, thereby obtaining the image subjected to the rotation processing, wherein
the rotating angle acquisition device acquires the rotating angle of the rotational magnetic field with respect to a point in time after a delay time has elapsed from reception of output of the image capturing timing detection device up to image capturing performed by the image pickup device.

2. A medical system according to claim 1, wherein the medical device includes a propelling force generating structure which is provided to the medical device, for generating propelling force with respect to the medical device by rotation of the medical device.

3. A medical system according to claim 1, wherein the image pickup device has an optical axis parallel to an axis direction of the insertion axis.

4. A medical system according to claim 1, wherein the rotating device for the medical device comprises:
a magnetic field generating device installed outside of a body for generating a rotational magnetic field;
a magnet, which is provided to the medical device and which is placed with magnetic poles of N-pole and S-pole being along a direction orthogonal to an axis direction of the insertion axis, for generating torque for rotating the medical device by interaction with the rotational magnetic field generated by the magnetic field generating device; and
a magnetic field control device installed outside of the body for controlling the rotational magnetic field generated by the magnetic field generating device.

5. A medical system according to claim 4, wherein the upper direction of the image pickup device matches direction of the magnetic poles of the magnet.

6. A medical system according to claim 4, wherein the upper direction of the image pickup device and direction of the magnetic poles of the magnet are arranged with a predetermined fixed angle.

7. A medical system according to claim 4, wherein the image acquisition device performs the rotation processing with the angle between the upper direction of the image pickup device and the magnetic direction of the magnet as a reference angle.

8. A medical system according to claim 4, further including an operation input device for inputting the angle between the upper direction of the image pickup device and the magnetic direction of the magnet, wherein the image acquisition device performs the rotation processing with the angle input from the operation input device as a reference angle.

9. A medical system according to claim 1, wherein the rotating device for the medical device comprises:
   a motor for driving so as to rotate the medical device; and
   an operation input device which allows change in the rotational speed of the motor.

10. A medical system according to claim 1, wherein the image acquisition device has a function for transmitting the image capturing timing signal to the image capturing timing detection device, as well as a function for transmitting an image capturing request signal to the image pickup device.

11. A medical system according to claim 1, wherein the medical device includes an image capturing timing controller for controlling the image capturing timing,
   and wherein the image pickup device transmits image data to the image acquisition device as well as performing image capturing in response to a signal received from the image capturing timing controller,
   and wherein the image capturing timing detection device detects the start of transmission of the image data by the image pickup device, as the image capturing timing.

12. A medical system according to claim 11, wherein the image capturing timing controller appends information regarding the image capturing timing to the image data to be transmitted.

13. A medical system according to claim 11, wherein the image capturing timing controller controls so as to maintain the constant interval between the time of image capturing and the time of the start of transmission of the image data.

14. A medical system according to claim 11, wherein the image capturing timing controller controls such that the time of image capturing matches the time of the start of image data transmission.

15. A medical system according to claim 1, further including a display device for displaying an image subjected to rotation processing by the image acquisition device, the rotation processing being for correcting the captured image by the rotating angle by which the medical device is rotated using the rotational magnetic field.

16. A medical system according to claim 1, wherein the medical device is a capsule endoscope including an internal wireless communication device for performing wireless communication from inside a body to outside the body,
   and wherein the medical system includes an external wireless communication device connected to the image acquisition device, for performing wireless communication from outside a body to inside the body, and performs wireless communication between the internal wireless communication device and the external wireless communication device.

17. A medical system according to claim 1, wherein the medical device includes a data compression device for performing compression processing for compressing data of the image into compressed data,
   and wherein the compressed data compressed by the data compression device is transmitted to the image acquisition device,
   and wherein the image acquisition device includes a data decompression device for performing decompression processing for the compressed data.

18. A medical system according to claim 1, wherein the rotating device for the medical device includes a storage device for storing past rotating angles acquired in past image capturing which is prior to a time of the image capturingperformed by the image pickup device,
   and wherein the rotating angle acquisition device refers to the past rotating angles when performing rotation processing on an image captured in the past.

19. A medical system according to claim 18, wherein the rotating angle acquisition device acquires the rotating angle in the past by the time corresponding to a period during which the image capturing timing detection device detected the signal.

20. A medical system according to claim 18 wherein the storage device stores the rotating angle information of the rotating device for the medical device in a form correlated with information regarding the point in time.

21. A medical system according to claim 1, wherein the image acquisition device acquires the amount of delay in rotation following of the medical device,
   and wherein the rotation processing is performed so as to correct for the amount of delay in rotation following.

22. A medical system according to claim 1, further including a plurality of image pickup devices,
   wherein the image acquisition device performs rotation processing for the image captured by each of the plurality of image pickup devices.

23. A medical system according to claim 22, wherein at least two of the image pickup devices have viewing directions different from each other.

24. A medical system according to claim 23, wherein at least two of the image pickup devices have viewing directions approximately parallel to the insertion axis.

25. A medical system according to claim 22, wherein the image acquisition device performs different rotation processing for images captured by different image pickup devices, corresponding to each image pickup device.

26. A medical system according to claim 22, further including a display device for displaying the images, captured by the image pickup devices, separately for each image pickup device.

27. A medical system according to claim 1, wherein:
   the image pickup device comprises first and second image pickup devices for picking up images in directions opposite to each other; and
   the image acquisition device performs processing to rotate, based on information regarding a rotating angle acquired by the rotating angle acquisition device, an image picked up by the first image pickup device in a first rotating angle corresponding to the acquired rotating angle, and performs processing to rotate an image picked up by the second image pickup device in a second rotating angle obtained by multiplying the first rotating angle by minus one.

28. A medical system according to claim 27, further comprising a display device for displaying only an image picked up by one of the first and second image pickup devices, the one of the devices picking up an image in a forward direction in the body cavity.

29. A medical system according to claim 27, further comprising a display device for displaying first and second images respectively picked up by the first and second image pickup devices, in sizes different from each other.

30. A medical system according to claim 17, wherein the medical device comprises an angular speed detecting device for detecting an angular speed, and the rotating angle acquisition device acquires the rotating angle on the basis of an integrated value of an output of the angular speed detecting device.

* * * * *